(12) United States Patent
Brandt et al.

(10) Patent No.: US 8,969,518 B2
(45) Date of Patent: Mar. 3, 2015

(54) B7 FAMILY MEMBER ZB7H6 AND RELATED COMPOSITIONS AND METHODS

(75) Inventors: Cameron S. Brandt, Seattle, WA (US); Jacob J. Kennedy, Seattle, WA (US); Wenfeng Xu, Seattle, WA (US); Eugene C. Yi, Mill Creek, WA (US); Brian A. Fox, Seattle, WA (US); Zeren Gao, Redmond, WA (US); Pallavur V. Sivakumar, Seattle, WA (US)

(73) Assignee: Zymogenetics, Inc., Princeton, NJ (US)

( * ) Notice: Subject to any disclaimer, the term of this patent is extended or adjusted under 35 U.S.C. 154(b) by 1077 days.

(21) Appl. No.: 12/943,256

(22) Filed: Nov. 10, 2010

(65) Prior Publication Data

US 2011/0081346 A1   Apr. 7, 2011

Related U.S. Application Data

(62) Division of application No. 12/246,214, filed on Oct. 6, 2008, now Pat. No. 7,858,759.

(60) Provisional application No. 60/977,584, filed on Oct. 4, 2007, provisional application No. 61/026,802, filed on Feb. 7, 2008, provisional application No. 61/095,875, filed on Sep. 10, 2008.

(51) Int. Cl.
| | | |
|---|---|---|
| *C07K 14/00* | (2006.01) | |
| *C07K 14/705* | (2006.01) | |
| *C07K 16/28* | (2006.01) | |
| *A61K 39/00* | (2006.01) | |

(52) U.S. Cl.
CPC ....... *C07K 16/2827* (2013.01); *C07K 14/70532* (2013.01); *A61K 2039/505* (2013.01); *C07K 2319/30* (2013.01)
USPC ........................................................ 530/350

(58) Field of Classification Search
CPC ...................... C07K 2319/30; C07K 14/70532
See application file for complete search history.

(56) References Cited

U.S. PATENT DOCUMENTS

| | | | | |
|---|---|---|---|---|
| 4,883,662 | A | 11/1989 | Stout ............................. | 424/101 |
| 5,082,833 | A | 1/1992 | Shamsuddin .................. | 514/143 |
| 2003/0022279 | A1* | 1/2003 | Fraser et al. .................. | 435/69.1 |
| 2007/0099251 | A1* | 5/2007 | Zhang et al. .................. | 435/7.23 |

FOREIGN PATENT DOCUMENTS

| | | |
|---|---|---|
| WO | 0151514 | 7/2001 |
| WO | 03054152 | 7/2003 |
| WO | 2004080148 | 9/2004 |
| WO | WO2004/073656 A2 | 9/2004 |
| WO | WO 2006/124668 A1 | 11/2006 |
| WO | 2008021290 * | 2/2008 |

OTHER PUBLICATIONS

Sequence alignment, 2014, 2 pages.*
Abbas et al., *Nat. Med.*, 5:1345-6,1999.
Coyle et al., *Nat. Immunol.*, 2: 203-9, 2001.
Carreno et al., *Annu. Rev. Immunol.*, 20: 29-53, 2002.
Liang et al., *Curr. Opin. Immunol.*, 14: 384-90, 2002.
Cudowicz and Bennett, *J. Exp. Med.* 134:83-102, 1971.
Cudowicz and Bennett, *J. Exp. Med.* 135:1513-1528, 1971.
Herberman and Ortaldo, *Science*, 214:24-30, 1981.
Ortaldo and Herberman, *Annu. Rev. Immunol.* 2:359-394, 1984.
Trinchieri, *Adv. Immunol.* 47:187-376, 1989.
Murphy et al., *J. Natl. Cancer Inst.* 85:1475-1482, 1993.
Murphy et al., *J. Exp. Med.* 165:1212-1217, 1987.
Yamazaki et al., *Oncology Reports* 9:359-363, 2002.
Rosenberg et al., *Cancer Research* 51:5074-5079 (suppl.), 1991.
Britteenden et al., *Cancer* 77:1226-1243, 1996.
Barao and Murphy, *BB&MT* 9:727-741, 2003.
Moretta et al., *Annu. Rev. Immunol.* 19:197-223, 2001.
Diefenbach and Raulet, *Immunol. Rev.*, 181:170-184, 2001.
International Preliminary Report on Patentability (Search Report) issued Apr. 21, 2011.
Database EMBL [Online] Aug. 19, 2004, Database accession No. CR749521.
Database UniProt [Online] Oct. 11, 2004, Database accession No. Q68D85.
Von Strandmann Elke Pogge et al., *Blood*, vol. 108, No. 11, Part 1, Nov. 2006, p. 194A.
Moretta Lorenzo et al., "Unraveling natural killer cell function: triggering and inhibitory human NK receptors," EMBO (European Molecular Biology Organization) Journal, vol. 23, No. 2, Jan. 24, pp. 255-259, (2004).
Pende D. et al., "Identification and Molecular Characterization of NKp30, a Novel Triggering Receptor Involved in Natural Cytotoxicity Mediated by Human Natural Killer Cells," The Journal of Experimental Medicine, Rockefeller University Press, US, vol. 190, No. 10, Nov. 1999, pp. 1505-1516.
Brandt Cameron S. et al., "The B7 family member B7-H6 is a tumor cell ligand for the activating natural killer cell receptor NKp30 in humans," The Journal of Experimental Medicine, Jul. 2009, vol. 206, No. 7, pp. 1495-1503 (PubMed: 19528259).

* cited by examiner

*Primary Examiner* — Ilia Ouspenski
(74) *Attorney, Agent, or Firm* — Gregory R. Bellomy; Nickki Parlet

(57) ABSTRACT

Disclosed is a newly identified B7 family member, zB7H6, which functions as a counter-receptor for the NK cell triggering receptor, NKp30. Methods and compositions for modulating NKp30-mediated NK cell activity based on the interaction of zB7H6 with NKp30, as well as related screening methods, are also disclosed. Further disclosed are anti-zB7H6 antibodies as well as antibody-drug conjugates comprising an anti-zB7H6 antibody conjugated to a therapeutic agent, including methods for using such antibodies and antibody-drug conjugates to exert therapeutic effects against zB7H6-expressing cells.

2 Claims, 20 Drawing Sheets

K562

BaF3

MTWRAAASTCAALLILLWALTTEGDLKVEMMAGGTQITPLN
DNVTIFCNIFYSQPLNITSMGITWFWKSLTFDKEVKVFEFFG
DHQEAFRPGAIVSPWRLKSGDASLRLPGIQLEEAGEYRCE
VVVTPLKAQGTVQLEVVASPASRLLLDQVGMKENEDKYMC
ESSGFYPEAINITWEKQTQKFPHPIEISEDVITGPTIKNMDG
TFNVTSCLKLNSSQEDPGTVYQCVVRHASLHTPLRSNFTL
TAARHSLSETEKTDNFSIHWWPISFIGVGLVLLIVLIPWKKIC
NKSSSAYTPLKCILKHWNSFDTQTLKKEHLIFFCTRAWPSY
QLQDGEAWPPEGSVNINTIQQLDVFCRQEGKWSEVPYVQ
AFFALRDNPDLCQCCRIDPALLTVTSGKSIDDNSTKSEKQT
PREHSDAVPDAPILPVSPIWEPPPATTSTTPVLSSQPPTLLL
PLQ

Figure 6

|       |     |     |     |     |     | LC  |     |     |     |     | HC  |     | HC  |     |
|-------|-----|-----|-----|-----|-----|-----|-----|-----|-----|-----|-----|-----|-----|-----|
|       | 218 |     |     |     | 222 |     |     |     |     |     |     |     | 230 |     |
| wt    | Glu | Pro | Lys | Ser | Cys | Asp | Lys | Thr | His | Thr | Cys | Pro | Pro | Cys | Pro |
| Fc-488|  .  |  .  | Arg |  .  | Ser |  .  |  .  |  .  |  .  |  .  |  .  |  .  |  .  |  .  |  .  |
| Fc4   |  .  |  .  | Arg |  .  | Ser |  .  |  .  |  .  |  .  |  .  |  .  |  .  |  .  |  .  |  .  |
| Fc5   |  .  |  .  |  .  |  .  | Ser |  .  |  .  |  .  |  .  |  .  |  .  |  .  |  .  |  .  |  .  |
| Fc6   |  .  |  .  |  .  |  .  | Ser |  .  |  .  |  .  |  .  |  .  |  .  |  .  |  .  |  .  |  .  |
| Fc7   |  .  |  .  |  .  |  .  |  .  |  .  |  .  |  .  |  .  |  .  |  .  |  .  |  .  |  .  |  .  |

<- hinge ->

|       |     |     |     | 234 | 235 |     | 237 |     |     |     |     |     |     | 245 |     |
|-------|-----|-----|-----|-----|-----|-----|-----|-----|-----|-----|-----|-----|-----|-----|-----|
| wt    | Ala | Pro | Glu | Leu | Leu | Gly | Gly | Pro | Ser | Val | Phe | Leu | Phe | Pro | Pro |
| Fc-488|  .  |  .  |  .  |  .  |  .  |  .  |  .  |  .  |  .  |  .  |  .  |  .  |  .  |  .  |  .  |
| Fc4   |  .  |  .  |  .  | Ala | Glu |  .  | Ala |  .  |  .  |  .  |  .  |  .  |  .  |  .  |  .  |
| Fc5   |  .  |  .  |  .  | Ala | Glu |  .  | Ala |  .  |  .  |  .  |  .  |  .  |  .  |  .  |  .  |
| Fc6   |  .  |  .  |  .  | Ala | Glu |  .  | Ala |  .  |  .  |  .  |  .  |  .  |  .  |  .  |  .  |
| Fc7   |  .  |  .  |  .  |  .  |  .  |  .  |  .  |  .  |  .  |  .  |  .  |  .  |  .  |  .  |  .  |

|CH2 ->

|       |     |     |     |     |     |     |     |     |     |     |     |     |     | 260 |
|-------|-----|-----|-----|-----|-----|-----|-----|-----|-----|-----|-----|-----|-----|-----|
| wt    | Lys | Pro | Lys | Asp | Thr | Leu | Met | Ile | Ser | Arg | Thr | Pro | Glu | Val | Thr |
| Fc-488|  .  |  .  |  .  |  .  |  .  |  .  |  .  |  .  |  .  |  .  |  .  |  .  |  .  |  .  |  .  |
| Fc4   |  .  |  .  |  .  |  .  |  .  |  .  |  .  |  .  |  .  |  .  |  .  |  .  |  .  |  .  |  .  |
| Fc5   |  .  |  .  |  .  |  .  |  .  |  .  |  .  |  .  |  .  |  .  |  .  |  .  |  .  |  .  |  .  |
| Fc6   |  .  |  .  |  .  |  .  |  .  |  .  |  .  |  .  |  .  |  .  |  .  |  .  |  .  |  .  |  .  |
| Fc7   |  .  |  .  |  .  |  .  |  .  |  .  |  .  |  .  |  .  |  .  |  .  |  .  |  .  |  .  |  .  |

|       |     |     |     |     |     |     |     |     |     |     |     |     |     |     | 275 |
|-------|-----|-----|-----|-----|-----|-----|-----|-----|-----|-----|-----|-----|-----|-----|-----|
| wt    | Cys | Val | Val | Val | Asp | Val | Ser | His | Glu | Asp | Pro | Glu | Val | Lys | Phe |
| Fc-488|  .  |  .  |  .  |  .  |  .  |  .  |  .  |  .  |  .  |  .  |  .  |  .  |  .  |  .  |  .  |
| Fc4   |  .  |  .  |  .  |  .  |  .  |  .  |  .  |  .  |  .  |  .  |  .  |  .  |  .  |  .  |  .  |
| Fc5   |  .  |  .  |  .  |  .  |  .  |  .  |  .  |  .  |  .  |  .  |  .  |  .  |  .  |  .  |  .  |
| Fc6   |  .  |  .  |  .  |  .  |  .  |  .  |  .  |  .  |  .  |  .  |  .  |  .  |  .  |  .  |  .  |
| Fc7   |  .  |  .  |  .  |  .  |  .  |  .  |  .  |  .  |  .  |  .  |  .  |  .  |  .  |  .  |  .  |

|       |     |     |     |     |     |     |     |     |     |     |     |     |     |     | 290 |
|-------|-----|-----|-----|-----|-----|-----|-----|-----|-----|-----|-----|-----|-----|-----|-----|
| wt    | Asn | Trp | Tyr | Val | Asp | Gly | Val | Glu | Val | His | Asn | Ala | Lys | Thr | Lys |
| Fc-488|  .  |  .  |  .  |  .  |  .  |  .  |  .  |  .  |  .  |  .  |  .  |  .  |  .  |  .  |  .  |
| Fc4   |  .  |  .  |  .  |  .  |  .  |  .  |  .  |  .  |  .  |  .  |  .  |  .  |  .  |  .  |  .  |
| Fc5   |  .  |  .  |  .  |  .  |  .  |  .  |  .  |  .  |  .  |  .  |  .  |  .  |  .  |  .  |  .  |
| Fc6   |  .  |  .  |  .  |  .  |  .  |  .  |  .  |  .  |  .  |  .  |  .  |  .  |  .  |  .  |  .  |
| Fc7   |  .  |  .  |  .  |  .  |  .  |  .  |  .  |  .  |  .  |  .  |  .  |  .  |  .  |  .  |  .  |

|       |     |     |     |     |     | 297 |     |     |     |     |     |     |     |     | 305 |
|-------|-----|-----|-----|-----|-----|-----|-----|-----|-----|-----|-----|-----|-----|-----|-----|
| wt    | Pro | Arg | Glu | Glu | Gln | Tyr | Asn | Ser | Thr | Tyr | Arg | Val | Val | Ser | Val |
| Fc-488|  .  |  .  |  .  |  .  |  .  |  .  |  .  |  .  |  .  |  .  |  .  |  .  |  .  |  .  |  .  |
| Fc4   |  .  |  .  |  .  |  .  |  .  |  .  |  .  |  .  |  .  |  .  |  .  |  .  |  .  |  .  |  .  |
| Fc5   |  .  |  .  |  .  |  .  |  .  |  .  |  .  |  .  |  .  |  .  |  .  |  .  |  .  |  .  |  .  |
| Fc6   |  .  |  .  |  .  |  .  |  .  |  .  |  .  |  .  |  .  |  .  |  .  |  .  |  .  |  .  |  .  |
| Fc7   |  .  |  .  |  .  |  .  |  .  |  .  | Gln |  .  |  .  |  .  |  .  |  .  |  .  |  .  |

Fig. 13A

```
                                                                    320
wt       Leu Thr Val Leu His Gln Asp Trp Leu Asn Gly Lys Glu Tyr Lys
Fc-488    .   .   .   .   .   .   .   .   .   .   .   .   .   .   .
Fc4       .   .   .   .   .   .   .   .   .   .   .   .   .   .   .
Fc5       .   .   .   .   .   .   .   .   .   .   .   .   .   .   .
Fc6       .   .   .   .   .   .   .   .   .   .   .   .   .   .   .
Fc7       .   .   .   .   .   .   .   .   .   .   .   .   .   .   .

330 331         335
wt       Cys Lys Val Ser Asn Lys Ala Leu Pro Ala Pro Ile Glu Lys Thr
Fc-488    .   .   .   .   .   .   .   .   .   .   .   .   .   .   .
Fc4       .   .   .   .   .   .   .   .   .  Ser Ser  .   .   .   .
Fc5       .   .   .   .   .   .   .   .   .  Ser Ser  .   .   .   .
Fc6       .   .   .   .   .   .   .   .   .  Ser Ser  .   .   .   .
Fc7       .   .   .   .   .   .   .   .   .   .   .   .   .   .   .

350
wt       Ile Ser Lys Ala Lys|Gly Gln Pro Arg Glu Pro Gln Val Tyr Thr
Fc-488    .   .   .   .   . |  .   .   .   .   .   .   .   .   .   .
Fc4       .   .   .   .   . |  .   .   .   .   .   .   .   .   .   .
Fc5       .   .   .   .   . |  .   .   .   .   .   .   .   .   .   .
Fc6       .   .   .   .   . |  .   .   .   .   .   .   .   .   .   .
Fc7       .   .   .   .   . |  .   .   .   .   .   .   .   .   .   .
                         <- CH2|CH3 ->

356     358                                     365
wt       Leu Pro Pro Ser Arg Asp Glu Leu Thr Lys Asn Gln Val Ser Leu
Fc-488    .   .   .   .   .   .   .   .   .   .   .   .   .   .   .
Fc4       .   .   .   .   .   .   .   .   .   .   .   .   .   .   .
Fc5       .   .   .   .   .   .   .   .   .   .   .   .   .   .   .
Fc6       .   .   .   .   .   .   .   .   .   .   .   .   .   .   .
Fc7       .   .   .   .   .   .   .   .   .   .   .   .   .   .   .

380
wt       Thr Cys Leu Val Lys Gly Phe Tyr Pro Ser Asp Ile Ala Val Glu
Fc-488    .   .   .   .   .   .   .   .   .   .   .   .   .   .   .
Fc4       .   .   .   .   .   .   .   .   .   .   .   .   .   .   .
Fc5       .   .   .   .   .   .   .   .   .   .   .   .   .   .   .
Fc6       .   .   .   .   .   .   .   .   .   .   .   .   .   .   .
Fc7       .   .   .   .   .   .   .   .   .   .   .   .   .   .   .

395
wt       Trp Glu Ser Asn Gly Gln Pro Glu Asn Asn Tyr Lys Thr Thr Pro
Fc-488    .   .   .   .   .   .   .   .   .   .   .   .   .   .   .
Fc4       .   .   .   .   .   .   .   .   .   .   .   .   .   .   .
Fc5       .   .   .   .   .   .   .   .   .   .   .   .   .   .   .
Fc6       .   .   .   .   .   .   .   .   .   .   .   .   .   .   .
Fc7       .   .   .   .   .   .   .   .   .   .   .   .   .   .   .
```

Fig. 13B

| 410 | | | | | | | | | | | | | | |
|---|---|---|---|---|---|---|---|---|---|---|---|---|---|---|
| wt | Pro | Val | Leu | Asp | Ser | Asp | Gly | Ser | Phe | Phe | Leu | Tyr | Ser | Lys |
| Leu | | | | | | | | | | | | | | |
| Fc-488 | . | . | . | . | . | . | . | . | . | . | . | . | . | . |
| Fc4 | . | . | . | . | . | . | . | . | . | . | . | . | . | . |
| Fc5 | . | . | . | . | . | . | . | . | . | . | . | . | . | . |
| Fc6 | . | . | . | . | . | . | . | . | . | . | . | . | . | . |
| Fc7 | . | . | . | . | . | . | . | . | . | . | . | . | . | . |

| 425 | | | | | | | | | | | | | | |
|---|---|---|---|---|---|---|---|---|---|---|---|---|---|---|
| wt | Thr | Val | Asp | Lys | Ser | Arg | Trp | Gln | Gln | Gly | Asn | Val | Phe | Ser |
| Cys | | | | | | | | | | | | | | |
| Fc-488 | . | . | . | . | . | . | . | . | . | . | . | . | . | . |
| Fc4 | . | . | . | . | . | . | . | . | . | . | . | . | . | . |
| Fc5 | . | . | . | . | . | . | . | . | . | . | . | . | . | . |
| Fc6 | . | . | . | . | . | . | . | . | . | . | . | . | . | . |
| Fc7 | . | . | . | . | . | . | . | . | . | . | . | . | . | . |

| 440 | | | | 431 | | | | | | | | | |
|---|---|---|---|---|---|---|---|---|---|---|---|---|---|
| wt | Ser | Val | Met | His | Glu | Ala | Leu | His | Asn | His | Tyr | Thr | Gln | Lys |
| Ser | | | | | | | | | | | | | | |
| Fc-488 | . | . | . | . | . | . | . | . | . | . | . | . | . | . |
| Fc4 | . | . | . | . | . | . | . | . | . | . | . | . | . | . |
| Fc5 | . | . | . | . | . | . | . | . | . | . | . | . | . | . |
| Fc6 | . | . | . | . | . | . | . | . | . | . | . | . | . | . |
| Fc7 | . | . | . | . | . | . | . | . | . | . | . | . | . | . |

| 446 | | | | | | | |
|---|---|---|---|---|---|---|---|
| wt | Leu | Ser | Leu | Ser | Pro | Gly | Lys | *** |
| Fc-488 | . | . | . | . | . | . | . | . |
| Fc4 | . | . | . | . | . | . | . | . |
| Fc5 | . | . | . | . | . | . | . | . |
| Fc6 | . | . | . | . | . | . | *** | |
| Fc7 | . | . | . | . | . | . | . | . |

Fig. 13C

SEQUENCE LISTING

```
<160> NUMBER OF SEQ ID NOS: 34

<210> SEQ ID NO 1
<211> LENGTH: 1365
<212> TYPE: DNA
<213> ORGANISM: Homo sapiens

<400> SEQUENCE: 1
atgacgtgga gggctgccgc ctccacgtgc gcggcgctcc tgattctgct gtgggcgctg        60
acgaccgaag gtgatctgaa agtagagatg atggcagggg ggactcagat cacacccctg       120
aatgacaatg tcaccatatt ctgcaatatc ttttattccc aacccctcaa catcacgtct       180
atgggtatca cctggttttg gaagagtctg acgtttgaca aagaagtcaa agtctttgaa       240
ttttttggag atcaccaaga ggcattccga cctggagcca ttgtgtctcc atggaggctg       300
aagagtgggg acgcctcact gcggctgcct ggaatccagc tggaggaagc aggagagtac       360
cgatgtgagg tggtggtcac ccctctgaag gcacagggaa cagtccagct tgaagttgtg       420
gcttccccag ccagcagatt gttgctggat caagtgggca tgaaagagaa tgaagacaaa       480
tatatgtgtg agtcaagtgg gttctaccca gaggctatta atataacatg ggagaagcag       540
acccagaagt ttccccatcc catagagatt tctgaggatg tcatcactgg tcccaccatc       600
aagaatatgg atggcacatt taatgtcact agctgcttga agctgaactc ctctcaggaa       660
gaccctggga ctgtctacca gtgtgtggta cggcatgcgt ccttgcatac cccttgagg       720 agcaacttta ccctgactgc tgctcggcac agtctttctg aaactgagaa gacagataat       780
ttttccattc attggtggcc tatttcattc attggtgttg gactggtttt attaattgtt       840
ttgattcctt ggaaaaagat atgtaacaaa tcatcttcag cctatactcc tctcaagtgc       900
attctgaaac actggaactc ctttgacact cagactctga agaaagagca cctcatattc       960 tttgcactc gggcatggcc gtcttaccag ctgcaggatg gggaggcttg gcctcctgag      1020
ggaagtgtta atattaatac tattcaacaa ctagatgttt tctgcagaca ggagggcaaa      1080
tggtccgagg ttccttatgt gcaagccttc tttgccttgc gagacaaccc agatctttgt      1140
cagtgttgta gaattgaccc tgctctccta acagttacat caggcaagtc catagatgat      1200
aattccacaa agtctgagaa acaaaccct agggaacact cggatgcagt tccggatgcc      1260
ccaatccttc ctgtctcccc tatctgggaa cctcctccag ccacaacatc aacaactcca      1320
gttctatcct cccaaccccc aactttactg ttaccctac agtaa                      1365
```

```
<210> SEQ ID NO 2
<211> LENGTH: 454
<212> TYPE: PRT
<213> ORGANISM: Homo sapiens

<400> SEQUENCE: 2

Met Thr Trp Arg Ala Ala Ser Thr Cys Ala Ala Leu Leu Ile Leu
 1               5                  10                  15

Leu Trp Ala Leu Thr Thr Glu Gly Asp Leu Lys Val Glu Met Met Ala
                20                  25                  30

Gly Gly Thr Gln Ile Thr Pro Leu Asn Asp Asn Val Thr Ile Phe Cys
            35                  40                  45

Asn Ile Phe Tyr Ser Gln Pro Leu Asn Ile Thr Ser Met Gly Ile Thr
    50                  55                  60

Trp Phe Trp Lys Ser Leu Thr Phe Asp Lys Glu Val Lys Val Phe Glu
65                  70                  75                  80

Phe Phe Gly Asp His Gln Glu Ala Phe Arg Pro Gly Ala Ile Val Ser
                85                  90                  95

Pro Trp Arg Leu Lys Ser Gly Asp Ala Ser Leu Arg Leu Pro Gly Ile
                100                 105                 110

Gln Leu Glu Glu Ala Gly Glu Tyr Arg Cys Glu Val Val Val Thr Pro
            115                 120                 125

Leu Lys Ala Gln Gly Thr Val Gln Leu Glu Val Val Ala Ser Pro Ala
    130                 135                 140

Ser Arg Leu Leu Leu Asp Gln Val Gly Met Lys Glu Asn Glu Asp Lys
145                 150                 155                 160

Tyr Met Cys Glu Ser Ser Gly Phe Tyr Pro Glu Ala Ile Asn Ile Thr
                165                 170                 175

Trp Glu Lys Gln Thr Gln Lys Phe Pro His Pro Ile Glu Ile Ser Glu
                180                 185                 190

Asp Val Ile Thr Gly Pro Thr Ile Lys Asn Met Asp Gly Thr Phe Asn
            195                 200                 205

Val Thr Ser Cys Leu Lys Leu Asn Ser Ser Gln Glu Asp Pro Gly Thr
    210                 215                 220

Val Tyr Gln Cys Val Val Arg His Ala Ser Leu His Thr Pro Leu Arg
225                 230                 235                 240

Ser Asn Phe Thr Leu Thr Ala Ala Arg His Ser Leu Ser Glu Thr Glu
                245                 250                 255

Lys Thr Asp Asn Phe Ser Ile His Trp Trp Pro Ile Ser Phe Ile Gly
                260                 265                 270

Val Gly Leu Val Leu Leu Ile Val Leu Ile Pro Trp Lys Lys Ile Cys
            275                 280                 285

Asn Lys Ser Ser Ser Ala Tyr Thr Pro Leu Lys Cys Ile Leu Lys His
    290                 295                 300

Trp Asn Ser Phe Asp Thr Gln Thr Leu Lys Lys Glu His Leu Ile Phe
305                 310                 315                 320

Phe Cys Thr Arg Ala Trp Pro Ser Tyr Gln Leu Gln Asp Gly Glu Ala
                325                 330                 335

Trp Pro Pro Glu Gly Ser Val Asn Ile Asn Thr Ile Gln Gln Leu Asp
                340                 345                 350

Val Phe Cys Arg Gln Glu Gly Lys Trp Ser Glu Val Pro Tyr Val Gln
            355                 360                 365

Ala Phe Phe Ala Leu Arg Asp Asn Pro Asp Leu Cys Gln Cys Cys Arg
    370                 375                 380
```

```
Ile Asp Pro Ala Leu Leu Thr Val Thr Ser Gly Lys Ser Ile Asp Asp
385                 390                 395                 400

Asn Ser Thr Lys Ser Glu Lys Gln Thr Pro Arg Glu His Ser Asp Ala
                405                 410                 415

Val Pro Asp Ala Pro Ile Leu Pro Val Ser Pro Ile Trp Glu Pro Pro
            420                 425                 430

Pro Ala Thr Thr Ser Thr Thr Pro Val Leu Ser Ser Gln Pro Pro Thr
        435                 440                 445

Leu Leu Leu Pro Leu Gln
    450

<210> SEQ ID NO 3
<211> LENGTH: 2207
<212> TYPE: DNA
<213> ORGANISM: Homo sapiens

<400> SEQUENCE: 3 cccctctcctg tggggttcat tggggcatcc cctttctgct gcaggaacct ctcatcagac    60
cgcctgaggg aagcggcgcc cggagacccg ccccggcccg gtccacattc tccccaggaa   120
gccggactct atggggcggg accctggggg agcctgagcc gagcccggag ccagccccga   180
accctgaac ctccagccag gggcgccccg ggagcagcca gccgtgggc gagccgcccg      240
cccgccgagc agccatgagc gagacggtca tctgttccag ccgggccact gtgatgcttt   300
atgatgatgg caacaagcga tggctccctg ctggcacggg tccccaggcc ttcagccgcg   360
tccagatcta ccacaacccc acggccaatt cctttcgcgt cgtgggccgg aagatgcagc   420
ccgaccagca ggtggtcatc aactgtgcca tcgtccgggg tgtcaagtat aaccaggcca   480
cccccaactt ccatcagtgg gcgcgacgctc gccaggtctg ggcctcaac ttcggcagca    540
aggaggatgc ggcccagttt gccgccggca tggccagtgc cctagaggcg ttggaaggag   600
gtgggcccc tccaccccca gcacttccca cctggtcggt cccgaacggc ccctccccgg    660
aggaggtgga gcagcagaaa aggcagcagc ccggcccgtc ggagcacata gagcgccggg   720
tctccaatgc aggaggccca cctgctcccc ccgctggggg tccaccccca ccaccaggac   780
ctccccctcc tccaggtccc ccccacccc caggtttgcc cccttcgggg gtcccagctg    840
cagcgcacgg agcaggggga ggaccacccc ctgcaccccc tctcccggca gcacagggcc   900
ctggtggtgg gggagctggg gccccaggcc tggccgcagc tattgctgga gccaaactca   960
ggaaagtcag caagcaggag gaggcctcag gggggcccac agcccccaaa gctgagagtg  1020
gtcgaagcgc aggtgggga ctcatggaag agatgaacgc catgctggcc cggagaagga   1080
aagccacgca agttggggag aaaaccccca aggatgaatc tgccaatcag gaggagccag  1140
aggccagagt cccggcccag agtgaatctg tgcggagacc ctgggagaag aacagcacaa  1200
ccttgccaag gatgaagtcg tcttcttcgg tgaccacttc cgagacccaa ccctgcacgc  1260
ccagctccag tgattactcg gacctacaga gggtgaaaca ggagcttctg aagaggtga   1320
agaaggaatt gcagaaagtg aaagaggaaa tcattgaagc cttcgtccag gagctgagga  1380
agcggggttc tccctgacca cagggaccca gaagacccgc ttctcctttc cgcacacccg  1440
gcctgtcacc ctgctttccc tgcctctact tgacttggaa ttggctgaag acacaggaat  1500
gcatcgttcc cactccccat cccacttgga aaactccaag ggggtgtggc ttccctgctc  1560
acacccacac tggctgctga ttggctgggg aggccccgc cttttctcc ctttggtcct   1620
tccctctgc catcccccttg gggccggtcc ctctgctggg gatgcaccaa tgaacccac    1680
```

```
aggaaggggg aaggaaggag ggaatttcac attcccttgt tctagattca ctttaacgct   1740
taatgccttc aaagttttgg ttttttttaag aaaaaaaaat atatatatat ttgggttttg   1800
ggggaaaagg gaaattttt tttctctttg gttttgataa aatgggatgt gggagttttt   1860
aaatgctata gccctgggct tgccccattt ggggcagcta tttaagggga ggggatgtct   1920
caccgggctg ggggtgagat atccccccac cccagggact cccttccct ctggctcctt   1980 cccctttttct atgaggaaat aagatgctgt aacttttttgg aacctcagtt tttttgatttt   2040 ttatttgggt aggttttggg gtccaggcca tttttttttac cccttggagg aaataagatg   2100
agggagaaag gagaagggga ggaaacttct cccctcccac cttcacctt agcttcttga   2160 aaatgggccc ctgcagaata atctgccag tttttataaa aaaaaaa              2207
```

<210> SEQ ID NO 4
<211> LENGTH: 380
<212> TYPE: PRT
<213> ORGANISM: Homo sapiens

<400> SEQUENCE: 4

```
Met Ser Glu Thr Val Ile Cys Ser Ser Arg Ala Thr Val Met Leu Tyr
1               5                   10                  15

Asp Asp Gly Asn Lys Arg Trp Leu Pro Ala Gly Thr Gly Pro Gln Ala
            20                  25                  30

Phe Ser Arg Val Gln Ile Tyr His Asn Pro Thr Ala Asn Ser Phe Arg
        35                  40                  45

Val Val Gly Arg Lys Met Gln Pro Asp Gln Gln Val Val Ile Asn Cys
    50                  55                  60

Ala Ile Val Arg Gly Val Lys Tyr Asn Gln Ala Thr Pro Asn Phe His
65                  70                  75                  80

Gln Trp Arg Asp Ala Arg Gln Val Trp Gly Leu Asn Phe Gly Ser Lys
                85                  90                  95

Glu Asp Ala Ala Gln Phe Ala Ala Gly Met Ala Ser Ala Leu Glu Ala
            100                 105                 110

Leu Glu Gly Gly Gly Pro Pro Pro Pro Ala Leu Pro Thr Trp Ser
        115                 120                 125

Val Pro Asn Gly Pro Ser Pro Glu Glu Val Glu Gln Gln Lys Arg Gln
    130                 135                 140

Gln Pro Gly Pro Ser Glu His Ile Glu Arg Arg Val Ser Asn Ala Gly
145                 150                 155                 160

Gly Pro Pro Ala Pro Ala Gly Gly Pro Pro Pro Gly Pro
                165                 170                 175

Pro Pro Pro Pro Gly Pro Pro Pro Pro Gly Leu Pro Ser Gly
            180                 185                 190

Val Pro Ala Ala Ala His Gly Ala Gly Gly Pro Pro Ala Pro
        195                 200                 205

Pro Leu Pro Ala Ala Gln Gly Pro Gly Gly Gly Ala Gly Ala Pro
    210                 215                 220

Gly Leu Ala Ala Ala Ile Ala Gly Ala Lys Leu Arg Lys Val Ser Lys
225                 230                 235                 240

Gln Glu Glu Ala Ser Gly Gly Pro Thr Ala Pro Lys Ala Glu Ser Gly
                245                 250                 255

Arg Ser Gly Gly Gly Gly Leu Met Glu Glu Met Asn Ala Met Leu Ala
            260                 265                 270

Arg Arg Arg Lys Ala Thr Gln Val Gly Glu Lys Thr Pro Lys Asp Glu
        275                 280                 285
```

```
Ser Ala Asn Gln Glu Glu Pro Glu Ala Arg Val Pro Ala Gln Ser Glu
    290                 295                 300

Ser Val Arg Arg Pro Trp Glu Lys Asn Ser Thr Thr Leu Pro Arg Met
305                 310                 315                 320

Lys Ser Ser Ser Val Thr Thr Ser Glu Thr Gln Pro Cys Thr Pro
                325                 330                 335

Ser Ser Ser Asp Tyr Ser Asp Leu Gln Arg Val Lys Gln Glu Leu Leu
            340                 345                 350

Glu Glu Val Lys Lys Glu Leu Gln Lys Val Lys Glu Glu Ile Ile Glu
        355                 360                 365

Ala Phe Val Gln Glu Leu Arg Lys Arg Gly Ser Pro
    370                 375                 380

<210> SEQ ID NO 5
<211> LENGTH: 4
<212> TYPE: PRT
<213> ORGANISM: Artificial Sequence
<220> FEATURE:
<223> OTHER INFORMATION: Polypeptide Linker

<400> SEQUENCE: 5

Gly Ser Gly Gly
 1

<210> SEQ ID NO 6
<211> LENGTH: 8
<212> TYPE: PRT
<213> ORGANISM: Artificial Sequence
<220> FEATURE:
<223> OTHER INFORMATION: FLAG tag

<400> SEQUENCE: 6

Asp Tyr Lys Asp Asp Asp Asp Lys
 1               5

<210> SEQ ID NO 7
<211> LENGTH: 6
<212> TYPE: PRT
<213> ORGANISM: Artificial Sequence
<220> FEATURE:
<223> OTHER INFORMATION: Six-His tag

<400> SEQUENCE: 7

His His His His His His
 1               5

<210> SEQ ID NO 8
<211> LENGTH: 365
<212> TYPE: PRT
<213> ORGANISM: Artificial Sequence
<220> FEATURE:
<223> OTHER INFORMATION: NKp30/mFc2

<400> SEQUENCE: 8

Met Ala Trp Met Leu Leu Leu Ile Leu Ile Met Val His Pro Gly Ser
 1               5                  10                  15

Cys Ala Leu Trp Val Ser Gln Pro Pro Glu Ile Arg Thr Leu Glu Gly
            20                  25                  30

Ser Ser Ala Phe Leu Pro Cys Ser Phe Asn Ala Ser Gln Gly Arg Leu
        35                  40                  45

Ala Ile Gly Ser Val Thr Trp Phe Arg Asp Glu Val Val Pro Gly Lys
    50                  55                  60
```

```
Glu Val Arg Asn Gly Thr Pro Glu Phe Arg Gly Arg Leu Ala Pro Leu
 65                  70                  75                  80

Ala Ser Ser Arg Phe Leu His Asp His Gln Ala Glu Leu His Ile Arg
                 85                  90                  95

Asp Val Arg Gly His Asp Ala Ser Ile Tyr Val Cys Arg Val Glu Val
            100                 105                 110

Leu Gly Leu Gly Val Gly Thr Gly Asn Gly Thr Arg Leu Val Val Glu
        115                 120                 125

Lys Glu His Pro Glu Pro Arg Ser Pro Thr Ile Lys Pro Cys Pro Pro
130                 135                 140

Cys Lys Cys Pro Ala Pro Asn Leu Glu Gly Gly Pro Ser Val Phe Ile
145                 150                 155                 160

Phe Pro Pro Lys Ile Lys Asp Val Leu Met Ile Ser Leu Ser Pro Ile
                165                 170                 175

Val Thr Cys Val Val Val Asp Val Ser Glu Asp Asp Pro Asp Val Gln
            180                 185                 190

Ile Ser Trp Phe Val Asn Asn Val Glu Val His Thr Ala Gln Thr Gln
        195                 200                 205

Thr His Arg Glu Asp Tyr Asn Ser Thr Leu Arg Val Val Ser Ala Leu
    210                 215                 220

Pro Ile Gln His Gln Asp Trp Met Ser Gly Lys Ala Phe Ala Cys Ala
225                 230                 235                 240

Val Asn Asn Lys Asp Leu Pro Ala Pro Ile Glu Arg Thr Ile Ser Lys
                245                 250                 255

Pro Lys Gly Ser Val Arg Ala Pro Gln Val Tyr Val Leu Pro Pro Pro
            260                 265                 270

Glu Glu Glu Met Thr Lys Lys Gln Val Thr Leu Thr Cys Met Val Thr
        275                 280                 285

Asp Phe Met Pro Glu Asp Ile Tyr Val Glu Trp Thr Asn Asn Gly Lys
    290                 295                 300

Thr Glu Leu Asn Tyr Lys Asn Thr Glu Pro Val Leu Asp Ser Asp Gly
305                 310                 315                 320

Ser Tyr Phe Met Tyr Ser Lys Leu Arg Val Lys Lys Asn Trp Val
                325                 330                 335

Glu Arg Asn Ser Tyr Ser Cys Ser Val Val His Glu Gly Leu His Asn
            340                 345                 350

His His Thr Thr Lys Ser Phe Ser Arg Thr Pro Gly Lys
        355                 360                 365

<210> SEQ ID NO 9
<211> LENGTH: 36
<212> TYPE: DNA
<213> ORGANISM: Artificial Sequence
<220> FEATURE:
<223> OTHER INFORMATION: Oligonucleotide Primer

<400> SEQUENCE: 9
tcaggaattc gcaagatgac gtggagggct gccgcc                           36

<210> SEQ ID NO 10
<211> LENGTH: 31
<212> TYPE: DNA
<213> ORGANISM: Artificial Sequence
<220> FEATURE:
<223> OTHER INFORMATION: Oligonucleotide Primer

<400> SEQUENCE: 10
```

-continued ctgactcgag ttactgtagg ggtaacagta a                                    31

<210> SEQ ID NO 11
<211> LENGTH: 187
<212> TYPE: PRT
<213> ORGANISM: Artificial Sequence
<220> FEATURE:
<223> OTHER INFORMATION: NKp30/VASP

<400> SEQUENCE: 11

Met Ala Trp Met Leu Leu Ile Leu Ile Met Val His Pro Gly Ser
1               5                   10                  15

Cys Ala Leu Trp Val Ser Gln Pro Pro Glu Ile Arg Thr Leu Glu Gly
            20                  25                  30

Ser Ser Ala Phe Leu Pro Cys Ser Phe Asn Ala Ser Gln Gly Arg Leu
        35                  40                  45

Ala Ile Gly Ser Val Thr Trp Phe Arg Asp Glu Val Val Pro Gly Lys
    50                  55                  60

Glu Val Arg Asn Gly Thr Pro Glu Phe Arg Gly Arg Leu Ala Pro Leu
65                  70                  75                  80

Ala Ser Ser Arg Phe Leu His Asp His Gln Ala Glu Leu His Ile Arg
                85                  90                  95

Asp Val Arg Gly His Asp Ala Ser Ile Tyr Val Cys Arg Val Glu Val
            100                 105                 110

Leu Gly Leu Gly Val Gly Thr Gly Asn Gly Thr Arg Leu Val Val Glu
        115                 120                 125

Lys Glu His Pro Glu Pro Arg Ser Gly Ser Gly Gly Ser Gly Gly Ser
    130                 135                 140

Asp Leu Gln Arg Val Lys Gln Glu Leu Leu Glu Glu Val Lys Lys Glu
145                 150                 155                 160

Leu Gln Lys Val Lys Glu Glu Ile Ile Glu Ala Phe Val Gln Glu Leu
                165                 170                 175

Arg Gly Ser Gly Gly His His His His His
            180                 185

<210> SEQ ID NO 12
<211> LENGTH: 195
<212> TYPE: PRT
<213> ORGANISM: Artificial Sequence
<220> FEATURE:
<223> OTHER INFORMATION: zB7R1/VASP

<400> SEQUENCE: 12

Met Arg Trp Cys Leu Leu Ile Trp Ala Gln Gly Leu Arg Gln Ala
1               5                   10                  15

Pro Leu Ala Ser Gly Met Met Thr Gly Thr Ile Glu Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

```
Tyr Pro Asp Gly Ala Tyr Thr Gly Arg Ile Phe Leu Glu Val Leu Glu
            115                 120                 125

Ser Ser Val Ala Glu His Gly Ala Arg Phe Gln Ile Glu Pro Arg Ser
        130                 135                 140

Gly Ser Gly Gly Ser Gly Gly Ser Asp Leu Gln Arg Val Lys Gln Glu
145                 150                 155                 160

Leu Leu Glu Glu Val Lys Lys Glu Leu Gln Lys Val Lys Glu Glu Ile
                165                 170                 175

Ile Glu Ala Phe Val Gln Glu Leu Arg Gly Ser Gly Gly His His
            180                 185                 190

His His His
        195

<210> SEQ ID NO 13
<211> LENGTH: 276
<212> TYPE: PRT
<213> ORGANISM: Artificial Sequence
<220> FEATURE:
<223> OTHER INFORMATION: B7DC/VASP

<400> SEQUENCE: 13

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
            115                 120                 125

His Ile Leu Lys Val Pro Glu Thr Asp Glu Val Glu Leu Thr Cys Gln
        130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
            195                 200                 205

Leu Gln Ser Gln Met Glu Pro Arg Thr His Pro Thr Trp Glu Pro Arg
        210                 215                 220

Ser Gly Ser Gly Gly Ser Gly Gly Ser Asp Leu Gln Arg Val Lys Gln
225                 230                 235                 240

Glu Leu Leu Glu Glu Val Lys Lys Glu Leu Gln Lys Val Lys Glu Glu
                245                 250                 255

Ile Ile Glu Ala Phe Val Gln Glu Leu Arg Gly Ser Gly Gly His His
            260                 265                 270
```

His His His His
        275

<210> SEQ ID NO 14
<211> LENGTH: 687
<212> TYPE: PRT
<213> ORGANISM: Homo sapiens

<400> SEQUENCE: 14

Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
                20                  25                  30

Phe Arg Arg Thr Pro Lys Pro Glu Leu Trp Ala Glu Thr Asn Phe Pro
            35                  40                  45

Leu Ala Pro Trp Lys Asn Leu Thr Leu Trp Cys Arg Ser Pro Ser Gly
        50                  55                  60

Ser Thr Lys Glu Phe Val Leu Lys Asp Gly Thr Gly Trp Ile Ala
 65                  70                  75                  80

Thr Arg Pro Ala Ser Glu Gln Val Arg Ala Ala Phe Pro Leu Gly Ala
                85                  90                  95

Leu Thr Gln Ser His Thr Gly Ser Tyr His Cys His Ser Trp Glu Glu
            100                 105                 110

Met Ala Val Ser Glu Pro Ser Glu Ala Leu Glu Leu Val Gly Thr Asp
        115                 120                 125

Ile Leu Pro Lys Pro Val Ile Ser Ala Ser Pro Thr Ile Arg Gly Gln
130                 135                 140

Glu Leu Gln Leu Arg Cys Lys Gly Trp Leu Ala Gly Met Gly Phe Ala
145                 150                 155                 160

Leu Tyr Lys Glu Gly Glu Gln Glu Pro Val Gln Gln Leu Gly Ala Val
                165                 170                 175

Gly Arg Glu Ala Phe Phe Thr Ile Gln Arg Met Glu Asp Lys Asp Glu
            180                 185                 190

Gly Asn Tyr Ser Cys Arg Thr His Thr Glu Lys Arg Pro Phe Lys Trp
        195                 200                 205

Ser Glu Pro Ser Glu Pro Leu Glu Leu Val Ile Lys Glu Met Tyr Pro
    210                 215                 220

Lys Pro Phe Phe Lys Thr Trp Ala Ser Pro Val Val Thr Pro Gly Ala
225                 230                 235                 240

Arg Val Thr Phe Asn Cys Ser Thr Pro His Gln His Met Ser Phe Ile
                245                 250                 255

Leu Tyr Lys Asp Gly Ser Glu Ile Ala Ser Ser Asp Arg Ser Trp Ala
            260                 265                 270

Ser Pro Gly Ala Ser Ala Ala His Phe Leu Ile Ile Ser Val Gly Ile
        275                 280                 285

Gly Asp Gly Gly Asn Tyr Ser Cys Arg Tyr Tyr Asp Phe Ser Ile Trp
    290                 295                 300

Ser Glu Pro Ser Asp Pro Val Glu Leu Val Val Thr Glu Phe Tyr Pro
305                 310                 315                 320

Lys Pro Thr Leu Leu Ala Gln Pro Gly Pro Val Phe Pro Gly Lys
                325                 330                 335

Ser Val Ile Leu Arg Cys Gln Gly Thr Phe Gln Gly Met Arg Phe Ala
            340                 345                 350

Leu Leu Gln Glu Gly Ala His Val Pro Leu Gln Phe Arg Ser Val Ser

```
            355                 360                 365
Gly Asn Ser Ala Asp Phe Leu Leu His Thr Val Gly Ala Glu Asp Ser
370                 375                 380

Gly Asn Tyr Ser Cys Ile Tyr Tyr Glu Thr Thr Met Ser Asn Arg Gly
385                 390                 395                 400

Ser Tyr Leu Ser Met Pro Leu Met Ile Trp Val Thr Gly Leu Leu Pro
                405                 410                 415

Lys Pro Ser Leu Leu Ala Gln Pro Gly Pro Met Val Ala Pro Gly Glu
            420                 425                 430

Asn Met Thr Leu Gln Cys Gln Gly Glu Leu Pro Asp Ser Thr Phe Val
            435                 440                 445

Leu Leu Lys Glu Gly Ala Gln Glu Pro Leu Glu Gln Gln Arg Pro Ser
450                 455                 460

Gly Tyr Arg Ala Asp Phe Trp Met Pro Ala Val Arg Gly Glu Asp Ser
465                 470                 475                 480

Gly Ile Tyr Ser Cys Val Tyr Tyr Leu Asp Ser Thr Pro Phe Ala Ala
                485                 490                 495

Ser Asn His Ser Asp Ser Leu Glu Ile Trp Val Thr Asp Lys Pro Pro
            500                 505                 510

Lys Pro Ser Leu Ser Ala Trp Pro Ser Thr Met Phe Lys Leu Gly Lys
            515                 520                 525

Asp Ile Thr Leu Gln Cys Arg Gly Pro Leu Pro Gly Val Glu Phe Val
530                 535                 540

Leu Glu His Asp Gly Glu Glu Ala Pro Gln Gln Phe Ser Glu Asp Gly
545                 550                 555                 560

Asp Phe Val Ile Asn Asn Val Glu Gly Lys Gly Ile Gly Asn Tyr Ser
                565                 570                 575

Cys Ser Tyr Arg Leu Gln Ala Tyr Pro Asp Ile Trp Ser Glu Pro Ser
            580                 585                 590

Asp Pro Leu Glu Leu Val Gly Ala Ala Gly Pro Val Ala Gln Glu Cys
            595                 600                 605

Thr Val Gly Asn Ile Val Arg Ser Ser Leu Ile Val Val Val Val Val
610                 615                 620

Ala Leu Gly Val Val Leu Ala Ile Glu Trp Lys Lys Trp Pro Arg Leu
625                 630                 635                 640

Arg Thr Arg Gly Ser Glu Thr Asp Gly Arg Asp Gln Thr Ile Ala Leu
                645                 650                 655

Glu Glu Cys Asn Gln Glu Gly Glu Pro Gly Thr Pro Ala Asn Ser Pro
            660                 665                 670

Ser Ser Thr Ser Gln Arg Ile Ser Val Glu Leu Pro Val Pro Ile
            675                 680                 685

<210> SEQ ID NO 15
<211> LENGTH: 290
<212> TYPE: PRT
<213> ORGANISM: Homo sapiens

<400> SEQUENCE: 15

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45
```

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
             100                 105                 110

Arg Cys Met Ile Ser Tyr Gly Gly Ala Asp Tyr Lys Arg Ile Thr Val
         115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
290

<210> SEQ ID NO 16
<211> LENGTH: 1500
<212> TYPE: DNA
<213> ORGANISM: Artificial Sequence
<220> FEATURE:
<223> OTHER INFORMATION: zB7H6/mFc2

<400> SEQUENCE: 16
atgacgtgga gggctgccgc ctccacgtgc gcggcgctcc tgattctgct gtgggcgctg      60
acgaccgaag gtgatctgaa agtagagatg atggcagggg ggactcagat cacacccctg     120
aatgacaatg tcaccatatt ctgcaatatc ttttattccc aaccccctcaa catcacgtct     180 atgggtatca cctggttttg gaagagtctg acgtttgaca agaagtcaa agtctttgaa      240 ttttttggag atcaccaaga ggcattccga cctggagcca ttgtgtctcc atggaggctg     300
aagagtgggg acgcctcact gcggctgcct ggaatccagc tggaggaagc aggagagtac     360
cgatgtgagt ggtggtcac ccctctgaag gcacagggaa cagtccagct tgaagttgtg     420
gcttccccag ccagcagatt gttgctggat caagtgggca tgaaagagaa tgaagacaaa     480
tatatgtgtg agtcaagtgg gttctaccca gaggctatta atataacatg ggagaagcag     540
acccagaagt ttcccatcc catagagatt tctgaggatg tcatcactgg tcccaccatc     600
aagaatatgg atgcacatt taatgtcact agctgcttga agctgaactc ctctcaggaa     660

-continued

```
gaccctggga ctgtctacca gtgtgtggta cggcatgcgt ccttgcatac ccccttgagg    720
agcaacttta ccctgactgc tgctcggcac agtctttctg aaactgagaa dacagataat    780
ttttccattc attggtggcc tgagcccaga tctcccacaa tcaagccctg tcctccatgc    840
aaatgcccag cacctaacct cgaggtgga ccatccgtct tcatcttccc tccaaagatc    900
aaggatgtac tcatgatctc cctgagcccc atagtcacat gtgtggtggt ggatgtgagc    960
gaggatgacc cagatgtcca gatcagctgg tttgtgaaca acgtggaagt acacacagct   1020
cagacacaaa cccatagaga ggattacaac agtactctcc gggtggtcag tgccctcccc   1080
atccagcacc aggactggat gagtggcaaa gctttcgcat cgcgggtcaa caacaaagac   1140
ctcccagcgc ccatcgagag aaccatctca aacccaaag ggtcagtaag agctccacag    1200
gtatatgtct tgcctccacc agaagaagag atgactaaga acaggtcac tctgacctgc     1260 atggtcacag acttcatgcc tgaagacatt tacgtggagt ggaccaacaa cgggaaaaca    1320
gagctaaact acaagaacac tgaaccagtc ctggactctg atggttctta cttcatgtac    1380
agcaagctga gagtggaaaa aagaactgg gtggaaagaa atagctactc ctgttcagtg     1440
gtccacgagg gtctgcacaa tcaccacacg actaagagct ctcccggac tccgggtaaa    1500
```

<210> SEQ ID NO 17
<211> LENGTH: 500
<212> TYPE: PRT
<213> ORGANISM: Artificial Sequence
<220> FEATURE:
<223> OTHER INFORMATION: zB7H6/mFc2

<400> SEQUENCE: 17

```
Met Thr Trp Arg Ala Ala Ser Thr Cys Ala Ala Leu Leu Ile Leu
 1               5                  10                  15

Leu Trp Ala Leu Thr Thr Glu Gly Asp Leu Lys Val Glu Met Met Ala
                20                  25                  30

Gly Gly Thr Gln Ile Thr Pro Leu Asn Asp Asn Val Thr Ile Phe Cys
            35                  40                  45

Asn Ile Phe Tyr Ser Gln Pro Leu Asn Ile Thr Ser Met Gly Ile Thr
        50                  55                  60

Trp Phe Trp Lys Ser Leu Thr Phe Asp Lys Glu Val Lys Val Phe Glu
65                  70                  75                  80

Phe Phe Gly Asp His Gln Glu Ala Phe Arg Pro Gly Ala Ile Val Ser
                85                  90                  95

Pro Trp Arg Leu Lys Ser Gly Asp Ala Ser Leu Arg Leu Pro Gly Ile
            100                 105                 110

Gln Leu Glu Glu Ala Gly Glu Tyr Arg Cys Glu Val Val Val Thr Pro
        115                 120                 125

Leu Lys Ala Gln Gly Thr Val Gln Leu Glu Val Val Ala Ser Pro Ala
    130                 135                 140

Ser Arg Leu Leu Leu Asp Gln Val Gly Met Lys Glu Asn Glu Asp Lys
145                 150                 155                 160

Tyr Met Cys Glu Ser Ser Gly Phe Tyr Pro Glu Ala Ile Asn Ile Thr
                165                 170                 175

Trp Glu Lys Gln Thr Gln Lys Phe Pro His Pro Ile Glu Ile Ser Glu
            180                 185                 190

Asp Val Ile Thr Gly Pro Thr Ile Lys Asn Met Asp Gly Thr Phe Asn
        195                 200                 205

Val Thr Ser Cys Leu Lys Leu Asn Ser Ser Gln Glu Asp Pro Gly Thr
```

| | | | | | | | | | | |
|---|---|---|---|---|---|---|---|---|---|---|
| | | | 210 | | | 215 | | | 220 | |
| Val | Tyr | Gln | Cys | Val | Val | Arg | His | Ala | Ser | Leu | His | Thr | Pro | Leu | Arg |
| 225 | | | | 230 | | | | 235 | | | | 240 | | | |

Ser Asn Phe Thr Leu Thr Ala Ala Arg His Ser Leu Ser Glu Thr Glu
　　　　　　245　　　　　　　　　250　　　　　　　　255

Lys Thr Asp Asn Phe Ser Ile His Trp Trp Pro Glu Pro Arg Ser Pro
　　　　　260　　　　　　　　　265　　　　　　　　270

Thr Ile Lys Pro Cys Pro Pro Cys Lys Cys Pro Ala Pro Asn Leu Glu
　　　　275　　　　　　　　　280　　　　　　　　285

Gly Gly Pro Ser Val Phe Ile Phe Pro Pro Lys Ile Lys Asp Val Leu
　　　290　　　　　　　　　295　　　　　　　　300

Met Ile Ser Leu Ser Pro Ile Val Thr Cys Val Val Asp Val Ser
305　　　　　　　　310　　　　　　　　　315　　　　　　　　320

Glu Asp Asp Pro Asp Val Gln Ile Ser Trp Phe Val Asn Asn Val Glu
　　　　　　　　325　　　　　　　　　330　　　　　　　　335

Val His Thr Ala Gln Thr Gln Thr His Arg Glu Asp Tyr Asn Ser Thr
　　　　　　　340　　　　　　　　　345　　　　　　　　350

Leu Arg Val Val Ser Ala Leu Pro Ile Gln His Gln Asp Trp Met Ser
　　　　　355　　　　　　　　　360　　　　　　　　365

Gly Lys Ala Phe Ala Cys Ala Val Asn Asn Lys Asp Leu Pro Ala Pro
　　　370　　　　　　　　　375　　　　　　　　380

Ile Glu Arg Thr Ile Ser Lys Pro Lys Gly Ser Val Arg Ala Pro Gln
385　　　　　　　　390　　　　　　　　　395　　　　　　　　400

Val Tyr Val Leu Pro Pro Glu Glu Glu Met Thr Lys Lys Gln Val
　　　　　　　　405　　　　　　　　　410　　　　　　　　415

Thr Leu Thr Cys Met Val Thr Asp Phe Met Pro Glu Asp Ile Tyr Val
　　　　　　　420　　　　　　　　　425　　　　　　　　430

Glu Trp Thr Asn Asn Gly Lys Thr Glu Leu Asn Tyr Lys Asn Thr Glu
　　　　　435　　　　　　　　　440　　　　　　　　445

Pro Val Leu Asp Ser Asp Gly Ser Tyr Phe Met Tyr Ser Lys Leu Arg
　　　450　　　　　　　　　455　　　　　　　　460

Val Glu Lys Lys Asn Trp Val Glu Arg Asn Ser Tyr Ser Cys Ser Val
465　　　　　　　　470　　　　　　　　　475　　　　　　　　480

Val His Glu Gly Leu His Asn His His Thr Thr Lys Ser Phe Ser Arg
　　　　　　　485　　　　　　　　　490　　　　　　　　495

Thr Pro Gly Lys
　　　　500

<210> SEQ ID NO 18
<211> LENGTH: 969
<212> TYPE: DNA
<213> ORGANISM: Artificial Sequence
<220> FEATURE:
<223> OTHER INFORMATION: zB7H6/VASP

<400> SEQUENCE: 18

| | |
|---|---|
| atgacgtgga gggctgccgc ctccacgtgc gcggcgctcc tgattctgct gtgggcgctg | 60 |
| acgaccgaag gtgatctgaa agtagagatg atggcagggg ggactcagat cacacccctg | 120 |
| aatgacaatg tcaccatatt ctgcaatatc ttttattccc aacccctcaa catcacgtct | 180 |
| atgggtatca cctggttttg gaagagtctg acgtttgaca agaagtcaa agtctttgaa | 240 |
| ttttttggag atcaccaaga ggcattccga cctggagcca tgtgtctcc atggaggctg | 300 |
| aagagtgggg acgcctcact gcggctgcct ggaatccagc tggaggaagc aggagagtac | 360 |
| cgatgtgagg tggtggtcac ccctctgaag gcacaggaa cagtccagct tgaagttgtg | 420 |

```
gcttccccag ccagcagatt gttgctggat caagtgggca tgaaagagaa tgaagacaaa    480
tatatgtgtg agtcaagtgg gttctaccca gaggctatta atataacatg ggagaagcag    540
acccagaagt ttccccatcc catagagatt tctgaggatg tcatcactgg tcccaccatc    600
aagaatatgg atggcacatt taatgtcact agctgcttga agctgaactc ctctcaggaa    660
gaccctggga ctgtctacca gtgtgtggta cggcatgcgt ccttgcatac ccccttgagg    720
agcaacttta ccctgactgc tgctcggcac agtctttctg aaactgagaa acagataat     780 ttttccattc attggtggcc tgagcccaga tctggttccg gaggctccgg tggctccgac    840
ctacagaggg tgaaacagga gcttctggaa gaggtgaaga aggaattgca gaaagtgaaa    900
gaggaaatca ttgaagcctt cgtccaggag ctgaggggtt ccggtggcca tcaccatcac    960
catcactga                                                           969
```

<210> SEQ ID NO 19
<211> LENGTH: 322
<212> TYPE: PRT
<213> ORGANISM: Artificial Sequence
<220> FEATURE:
<223> OTHER INFORMATION: zB7H6/VASP

<400> SEQUENCE: 19

```
Met Thr Trp Arg Ala Ala Ser Thr Cys Ala Ala Leu Leu Ile Leu
 1               5                  10                  15

Leu Trp Ala Leu Thr Thr Glu Gly Asp Leu Lys Val Glu Met Met Ala
                20                  25                  30

Gly Gly Thr Gln Ile Thr Pro Leu Asn Asp Asn Val Thr Ile Phe Cys
            35                  40                  45

Asn Ile Phe Tyr Ser Gln Pro Leu Asn Ile Thr Ser Met Gly Ile Thr
        50                  55                  60

Trp Phe Trp Lys Ser Leu Thr Phe Asp Lys Glu Val Lys Val Phe Glu
 65                  70                  75                  80

Phe Phe Gly Asp His Gln Glu Ala Phe Arg Pro Gly Ala Ile Val Ser
                85                  90                  95

Pro Trp Arg Leu Lys Ser Gly Asp Ala Ser Leu Arg Leu Pro Gly Ile
            100                 105                 110

Gln Leu Glu Glu Ala Gly Glu Tyr Arg Cys Glu Val Val Val Thr Pro
        115                 120                 125

Leu Lys Ala Gln Gly Thr Val Gln Leu Glu Val Val Ala Ser Pro Ala
    130                 135                 140

Ser Arg Leu Leu Leu Asp Gln Val Gly Met Lys Glu Asn Glu Asp Lys
145                 150                 155                 160

Tyr Met Cys Glu Ser Ser Gly Phe Tyr Pro Glu Ala Ile Asn Ile Thr
                165                 170                 175

Trp Glu Lys Gln Thr Gln Lys Phe Pro His Pro Ile Glu Ile Ser Glu
            180                 185                 190

Asp Val Ile Thr Gly Pro Thr Ile Lys Asn Met Asp Gly Thr Phe Asn
        195                 200                 205

Val Thr Ser Cys Leu Lys Leu Asn Ser Ser Gln Glu Asp Pro Gly Thr
    210                 215                 220

Val Tyr Gln Cys Val Val Arg His Ala Ser Leu His Thr Pro Leu Arg
225                 230                 235                 240

Ser Asn Phe Thr Leu Thr Ala Ala Arg His Ser Leu Ser Glu Thr Glu
                245                 250                 255
```

```
Lys Thr Asp Asn Phe Ser Ile His Trp Trp Pro Glu Pro Arg Ser Gly
                260                 265                 270

Ser Gly Gly Ser Gly Gly Ser Asp Leu Gln Arg Val Lys Gln Glu Leu
        275                 280                 285

Leu Glu Glu Val Lys Lys Glu Leu Gln Lys Val Lys Glu Glu Ile Ile
    290                 295                 300

Glu Ala Phe Val Gln Glu Leu Arg Gly Ser Gly Gly His His His His
305                 310                 315                 320

His His
```

```
<210> SEQ ID NO 20
<211> LENGTH: 43
<212> TYPE: DNA
<213> ORGANISM: Artificial Sequence
<220> FEATURE:
<223> OTHER INFORMATION: oligonucleotide primer

<400> SEQUENCE: 20
tccacaggtg tccagggaat tcaccatgca tggctggctg ctc                    43

<210> SEQ ID NO 21
<211> LENGTH: 46
<212> TYPE: DNA
<213> ORGANISM: Artificial Sequence
<220> FEATURE:
<223> OTHER INFORMATION: oligonucleotide primer

<400> SEQUENCE: 21
agggcttgat tgtgggagat ctgggctcgg cagtctggaa ctgagc                 46

<210> SEQ ID NO 22
<211> LENGTH: 104
<212> TYPE: DNA
<213> ORGANISM: Artificial Sequence
<220> FEATURE:
<223> OTHER INFORMATION: oligonucleotide primer

<400> SEQUENCE: 22
acgcttccgt agatctggtt ccggaggctc cggtggctcc gacctacaga gggtgaaaca   60
ggagcttctg aagaggtga agaaggaatt gcagaaagtg aaag                   104

<210> SEQ ID NO 23
<211> LENGTH: 104
<212> TYPE: DNA
<213> ORGANISM: Artificial Sequence
<220> FEATURE:
<223> OTHER INFORMATION: oligonucleotide primer

<400> SEQUENCE: 23
aaggcgcgcc tctagatcag tgatggtgat ggtgatggcc accggaaccc ctcagctcct   60
ggacgaaggc ttcaatgatt tcctctttca ctttctgcaa ttcc                  104

<210> SEQ ID NO 24
<211> LENGTH: 47
<212> TYPE: DNA
<213> ORGANISM: Artificial Sequence
<220> FEATURE:
<223> OTHER INFORMATION: oligonucleotide primer

<400> SEQUENCE: 24
ctcagccagg aaatccatgc cgagttgaga cgcttccgta gatctgg                47
```

<210> SEQ ID NO 25
<211> LENGTH: 46
<212> TYPE: DNA
<213> ORGANISM: Artificial Sequence
<220> FEATURE:
<223> OTHER INFORMATION: oligonucleotide primer

<400> SEQUENCE: 25
ggggtgggta acccccaga gctgttttaa ggcgcgcctc tagatc        46

<210> SEQ ID NO 26
<211> LENGTH: 70
<212> TYPE: DNA
<213> ORGANISM: Artificial Sequence
<220> FEATURE:
<223> OTHER INFORMATION: oligonucleotide primer

<400> SEQUENCE: 26
ttgacatcca ctttgccttt ctctccacag gtgtccaggg aattcgcaaa tgacgtggag        60
ggctgccgcc        70

<210> SEQ ID NO 27
<211> LENGTH: 72
<212> TYPE: DNA
<213> ORGANISM: Artificial Sequence
<220> FEATURE:
<223> OTHER INFORMATION: oligonucleotide primer

<400> SEQUENCE: 27
caccctctgt aggtcggagc caccggagcc tccggaacca gatctgggct caggccacca        60
atgaatggaa aa        72

<210> SEQ ID NO 28
<211> LENGTH: 514
<212> TYPE: PRT
<213> ORGANISM: Artificial Sequence
<220> FEATURE:
<223> OTHER INFORMATION: B7H3/VASP

<400> SEQUENCE: 28

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175
Phe Trp Gln Asp Gly Gln Gly Val Pro Leu Thr Gly Asn Val Thr Thr
            180                 185                 190
Ser Gln Met Ala Asn Glu Gln Gly Leu Phe Asp Val His Ser Ile Leu
        195                 200                 205
Arg Val Val Leu Gly Ala Asn Gly Thr Tyr Ser Cys Leu Val Arg Asn
    210                 215                 220
Pro Val Leu Gln Gln Asp Ala His Ser Ser Val Thr Ile Thr Pro Gln
225                 230                 235                 240
Arg Ser Pro Thr Gly Ala Val Glu Val Gln Val Pro Glu Asp Pro Val
                245                 250                 255
Val Ala Leu Val Gly Thr Asp Ala Thr Leu Arg Cys Ser Phe Ser Pro
            260                 265                 270
Glu Pro Gly Phe Ser Leu Ala Gln Leu Asn Leu Ile Trp Gln Leu Thr
        275                 280                 285
Asp Thr Lys Gln Leu Val His Ser Phe Thr Glu Gly Arg Asp Gln Gly
    290                 295                 300
Ser Ala Tyr Ala Asn Arg Thr Ala Leu Phe Pro Asp Leu Leu Ala Gln
305                 310                 315                 320
Gly Asn Ala Ser Leu Arg Leu Gln Arg Val Arg Val Ala Asp Glu Gly
                325                 330                 335
Ser Phe Thr Cys Phe Val Ser Ile Arg Asp Phe Gly Ser Ala Ala Val
            340                 345                 350
Ser Leu Gln Val Ala Ala Pro Tyr Ser Lys Pro Ser Met Thr Leu Glu
        355                 360                 365
Pro Asn Lys Asp Leu Arg Pro Gly Asp Thr Val Thr Ile Thr Cys Ser
    370                 375                 380
Ser Tyr Arg Gly Tyr Pro Glu Ala Glu Val Phe Trp Gln Asp Gly Gln
385                 390                 395                 400
Gly Val Pro Leu Thr Gly Asn Val Thr Thr Ser Gln Met Ala Asn Glu
                405                 410                 415
Gln Gly Leu Phe Asp Val His Ser Val Leu Arg Val Val Leu Gly Ala
            420                 425                 430
Asn Gly Thr Tyr Ser Cys Leu Val Arg Asn Pro Val Leu Gln Gln Asp
        435                 440                 445
Ala His Gly Ser Val Thr Ile Thr Gly Gln Pro Met Thr Phe Ser Gly
    450                 455                 460
Ser Gly Ser Gly Gly Ser Asp Leu Gln Arg Val Lys Gln Glu Leu
465                 470                 475                 480
Leu Glu Glu Val Lys Lys Glu Leu Gln Lys Val Lys Glu Glu Ile Ile
                485                 490                 495
Glu Ala Phe Val Gln Glu Leu Arg Gly Ser Gly Gly His His His His
            500                 505                 510
His His

<210> SEQ ID NO 29
<211> LENGTH: 232
<212> TYPE: PRT
<213> ORGANISM: Homo sapien

<400> SEQUENCE: 29

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 30
<211> LENGTH: 232
<212> TYPE: PRT
<213> ORGANISM: Artificial Sequence
<220> FEATURE:
<223> OTHER INFORMATION: Fc-488

<400> SEQUENCE: 30

Glu Pro Arg Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

```
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Lys
225                 230
```

<210> SEQ ID NO 31
<211> LENGTH: 232
<212> TYPE: PRT
<213> ORGANISM: Artificial Sequence
<220> FEATURE:
<223> OTHER INFORMATION: Fc-4

<400> SEQUENCE: 31

```
Glu Pro Arg Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Lys
225                 230
```

<210> SEQ ID NO 32
<211> LENGTH: 232
<212> TYPE: PRT
<213> ORGANISM: Artificial Sequence
<220> FEATURE:

<223> OTHER INFORMATION: Effector function minus Fc (Fc5)

<400> SEQUENCE: 32

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 33
<211> LENGTH: 231
<212> TYPE: PRT
<213> ORGANISM: Artificial Sequence
<220> FEATURE:
<223> OTHER INFORMATION: Fc6

<400> SEQUENCE: 33

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 34
<211> LENGTH: 232
<212> TYPE: PRT
<213> ORGANISM: Artificial Sequence
<220> FEATURE:
<223> OTHER INFORMATION: Fc7

<400> SEQUENCE: 34

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Glu Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

```
Ser Leu Ser Leu Ser Pro Gly Lys
225                 230
```

B7 FAMILY MEMBER ZB7H6 AND RELATED COMPOSITIONS AND METHODS

CROSS-REFERENCE TO RELATED APPLICATIONS

The present application is a divisional of U.S. patent application Ser. No. 12/246,214, filed Oct. 6, 2008, now U.S. Pat. No. 7,858,759 which claims the benefit of U.S. Patent Application Ser. No. 60/977,584, filed Oct. 4, 2007, U.S. Patent Application Ser. No. 61/026,802, filed Feb. 7, 2008, and U.S. Patent Application Ser. No. 61/095,875, filed Sep. 10, 2008, each of which is incorporated by reference herein in its entirety.

BACKGROUND OF THE INVENTION

B7 Family

Positive and negative costimulatory signals play critical roles in the modulation of lymphocyte activity, and the molecules that mediate these signals have proven to be effective targets for immunomodulatory agents. For example, upon interaction with B7-1 or B7-2 on the surface of antigen-presenting cells (APC), CD28, the prototypic T cell costimulatory molecule, emits signals that promote T cell proliferation and differentiation in response to T cell receptor (TcR) engagement, while the CD28 homologue cytotoxic T lymphocyte antigen-4 (CTLA-4) mediates inhibition of T cell proliferation and effector functions. (See Chambers et al., *Ann. Rev. Immunol.*, 19:565-594, 2001; Egen et al., *Nature Immunol.*, 3:611-618, 2002.)

Several new molecules with homology to the B7 family have been discovered (Abbas et al., *Nat. Med.*, 5:1345-6, 1999; Coyle et al., *Nat. Immunol.*, 2: 203-9, 2001; Carreno et al., *Annu. Rev. Immunol.*, 20: 29-53, 2002; Liang et al., *Curr. Opin. Immunol.*, 14: 384-90, 2002), and their role in lymphocyte activation is just beginning to be elucidated. These new costimulatory counter-receptors include B7h2, PD-L1, PD-L2, B7-H3 and B7-H4.

The expression of known B7 family members is largely restricted to antigen-presenting cells. Collectively, these studies have revealed that B7 family members are counter-receptors on lymphoid cells that interact with cognate receptors on lymphocytes to provide positive or negative costimulatory signals that play critical roles in the regulation of cell-mediated immune responses.

Accordingly, there is a need in the art for the identification of additional B7 family members, their counter-receptors, and molecules derived therefrom that have lymphocyte costimulatory activity. This need is based largely on their fundamental biological importance and the therapeutic potential of agents capable of affecting their activity. Such agents capable of modulating costimulatory signals would find significant use in the modulation of immune responses, and are highly desirable.

NK Cells and NKp30

Natural killer (NK) cells are a subset of lymphocytes active in the immune system and represent an average of about 15% of mononuclear cells in human peripheral blood. NK cells were initially described functionally in 1971 by the observation that lethally irradiated mice were capable of rejecting allogeneic or parental strain bone marrow cell (BMC) allografts. (See Cudowicz and Bennett, *J. Exp. Med.* 134:83-102, 1971; Cudowicz and Bennett, *J. Exp. Med.* 135:1513-1528, 1971.) Cudowicz and Bennett observed that irradiated F1 hybrid H-2-heterozygous mice (A×B) were capable of rejecting parental H-2-homozygous BMC (A or B). This observation conflicted with the classic laws of transplantation in which transplantation antigens were thought to inherit co-dominantly and offspring were obligately tolerant toward parental major histocompatability complex (MHC) determinants. (See Cudowicz and Bennett, *J. Exp. Med.* 134:83-102, 1971.) The cells responsible for this phenomenon were found to be radioresistant and identical to lymphoid cells, which were characterized later in 1975 by their ability to mediate spontaneous killing of tumors in vitro in an MHC-unrestricted manner. (See Herberman and Ortaldo, *Science*, 214: 24-30, 1981; Ortaldo and Herberman, *Annu. Rev. Immunol.* 2:359-394, 1984; Trinchieri, *Adv. Immunol.* 47:187-376, 1989; Murphy et al., *J. Natl. Cancer Inst.* 85:1475-1482, 1993.) Additional evidence that NK cells alone could mediate the specificity of marrow graft rejection emerged in 1987 when it was observed that mice with severe combined immune deficiency (SCID), which cannot develop T and B cells, have normal NK cell function. (See Murphy et al., *J. Exp. Med.* 165:1212-1217, 1987.)

NK cells are currently understood to represent an important arm of innate immunity and to play a primary role in immune surveillance against tumors and virally infected cells. Unless activated, however, NK cells are ineffective in performing their normal function, even when present in otherwise sufficient numbers. Indeed, decreased NK cell activity is associated with cancer and infectious diseases (see Yamazaki et al., *Oncology Reports* 9:359-363, 2002; Rosenberg et al., *Cancer Research* 51:5074-5079 (suppl.), 1991; Britteenden et al., *Cancer* 77:1226-1243, 1996; U.S. Pat. Nos. 5,082,833 and 4,883,662). Conversely, as noted above, NK cell activity mediates acute rejection of BMC allografts. Therefore, levels of NK cell activity appear to play an important role in immune-related disorders.

NK cell activity is typically regulated by the interaction between MHC class I molecules and inhibitory and activating receptors. (See, e.g., Barao and Murphy, *BB&MT* 9:727-741, 2003.) The "missing self" hypothesis is originally based on the observation that tumor cells that lack MHC class I molecules are susceptible to killing by NK cells. (See Ljunggren and Karre, *Immunol. Today* 11:237-244, 1990; Ohlen et al., *J. Immunol.* 145:52-58, 1990.) Investigators additionally observed that human NK cells lyse class-I-deficient Epstein-Barr-virus-transformed B-lymphoblastoid cell lines. (Storkus et al., *Proc. Natl. Acad. Sci. USA* 86:2361-2364, 1989.) Also, it was found that transfection of class I genes into class I-deficient target cells caused these cells to be partially or completely resistant to NK cell-mediated lysis. (See Storkus et al., supra; Shimizu and DeMars, *Eur. J. Immunol.*, 19:447-451, 1989.) MHC class I, however, is not always necessary for protection from NK-cell-mediated cytotoxicity, and recognition by MHC class I does not always prevent cytolysis by NK cells. (Barao and Murphy, supra.) During recent years, various MHC-class-I-specific inhibitory and activating receptors as well as non-MHC-class-I-specific activating receptors have been identified. These receptors are relevant with respect to therapeutic approaches such as, e.g., allogeneic BMT and cancer therapy. (See id.)

Non-MHC-class-I-specific activating receptors, which are capable of mediating NK cell cytotoxicity against MHC-class-I-deficient or negative targets, are represented in part by a heterogeneous family of NK cell-specific immunoglobulin-like molecules that are known as natural cytotoxicity receptors (NCRs). (See, e.g., Moretta et al., *Annu. Rev. Immunol.* 19:197-223, 2001; Diefenbach and Raulet, *Immunol. Rev.*, 181:170-184, 2001.) In the absence of MHC class I expression (such as, for example, on tumor cells or virus-infected cells), ligation of these activating receptors on NK cells triggers target-cell killing. One such activating receptor is NKp30, which is selectively and constitutively expressed on mature natural killer (NK) cells and signals through, inter alia, coupling with CD3ζ. (See Barao and Murphy, supra.) The target-cell ligand to which NKp30 binds has not been previously identified.

This system of innate recognition by NK cells represents a potentially powerful tool for clinical application in allogeneic bone marrow transplantation (BMT), cancer therapy, or treatment of other NK-cell-associated disorders. (See, e.g., Barao and Murphy, supra.) For example, stimulating or inhibiting activation of NKp30 would be useful for modulating NK cell activity and treating diseases or disorders associated with NK cell activity. In particular, enhancement of NK cell activity by triggering NKp30 would be useful for treatment of diseases or disorders characterized by insufficient NK cell activity, such as cancer and infectious disease, while inhibition of NK cell activity by blocking NKp30 would be useful for treating NK-cell-mediated disorders, such as, for example, BMC allograft rejection. The present invention provides compositions and methods for these and other uses that should be apparent to those skilled in the art from the teachings herein.

BRIEF SUMMARY OF THE INVENTION

In one aspect, the present invention provides isolated zB7H6 polypeptides, including polypeptide fusions, comprising the amino acid sequence of SEQ ID NO:2 or a functional variant or fragment thereof. For example, in some embodiments, a zB7H6 polypeptide of the invention is an isolated, soluble polypeptide comprising a polypeptide segment that has at least 90% or at least 95% sequence identity with the amino acid sequence set forth in residues 25-266 of SEQ ID NO:2, wherein the soluble zB7H6 polypeptide is capable of specifically binding to human NKp30. In specific variations, such a soluble zB7H6 polypeptide comprises a polypeptide segment having the amino acid sequence set forth in residues 25-266 or 1-266 of SEQ ID NO:2. Such soluble polypeptides can be, for example, soluble fusion proteins. Suitable soluble fusion proteins include polypeptides further comprising an immunoglobulin heavy chain constant region (e.g., an Fc fragment), such as an IgG (e.g., IgG1, IgG2, IgG3, or IgG4), IgM, IgE, IgA, or IgD immunoglobulin heavy chain constant region. Other suitable soluble fusion proteins include polypeptides further comprising a VASP domain.

In another aspect, the present invention provides isolated polynucleotides encoding a zB7H6 polypeptide as described herein. Accordingly, in certain embodiments, the present invention provides an isolated polynucleotide comprising a polynucleotide segment encoding a soluble zB7H6 polypeptide, the zB7H6 polypeptide comprising a polypeptide segment that has at least 90% sequence identity with the amino acid sequence set forth in residues 25-266 of SEQ ID NO:2, and wherein the zB7H6 polypeptide is capable of specifically binding to human NKp30. In a specific variation, the encoded soluble zB7H6 polypeptide comprises a polypeptide segment having the amino acid sequence set forth in residues 25-266 of SEQ ID NO:2. The encoded soluble polypeptide can be, for example, a soluble fusion protein, such as a soluble fusion protein comprising an immunoglobulin heavy chain constant region or a VASP domain. In certain variations, the polynucleotide segment encoding the zB7H6 polypeptide comprises nucleotides 73-798 or 1-798 of SEQ ID NO:1.

In yet other aspects, the present invention provides vectors, including expression vectors, comprising a polynucleotide as above. For example, in some embodiments, the present invention provides an expression vector comprising the following operably linked elements: a transcription initiation region; a DNA segment encoding a soluble zB7H6 polypeptide, the zB7H6 polypeptide comprising a polypeptide segment that has at least 90% sequence identity with the amino acid sequence set forth in residues 25-266 of SEQ ID NO:2, wherein the zB7H6 polypeptide is capable of specifically binding to human NKp30; and a transcription termination region. In other, related aspects, the present invention provides host cells comprising such vectors, as well as methods for producing a zB7H6 polypeptide. In some embodiments, a method of producing a soluble zB7H6 polypeptide includes culturing a host cell comprising an expression vector as above under conditions in which the polypeptide is expressed, and recovering the expressed polypeptide.

The present invention also provides isolated antibodies that specifically bind to a zB7H6 polypeptide as described herein. For example, in certain embodiments, the present invention provides an antibody that specifically binds to a polypeptide segment having the amino acid sequence set forth in residues 25-266 of SEQ ID NO:2. In some such variations, the antibody inhibits the interaction of zB7H6 with human NKp30. Particularly suitable antibodies are monoclonal antibodies, such as, e.g., human or humanized monoclonal antibodies. Anti-zB7H6 antibodies also include single chain antibodies.

In still another aspect, the present invention provides methods for modulating human natural killer (NK) cell activity. Some such methods include enhancing NK cell activity by contacting a human NK cell with a cell expressing a recombinant, membrane-bound zB7H6 polypeptide, the zB7H6 polypeptide comprising a polypeptide segment that has at least 90% sequence identity with the amino acid sequence set forth in residues 25-266 of SEQ ID NO:2, and wherein the zB7H6 polypeptide is capable of specifically binding to human NKp30. In a specific variation, the zB7H6 polypeptide segment has the amino acid sequence set forth in residues 25-266 of SEQ ID NO:2.

Other methods for modulating NK cell activity include, e.g., decreasing NK cell activity against a zB7H6-expressing cell. Such methods generally comprise contacting a cell expressing functional zB7H6, in the presence of a human NK cell, with an effective amount of an antibody that specifically binds to a polypeptide segment having the amino acid sequence set forth in residues 25-266 of SEQ ID NO:2, wherein the antibody inhibits the interaction of zB7H6 with human NKp30. Such methods for decreasing NK cell activity are useful, for example, in the treatment of bone marrow cell (BMC) allograft rejection. Accordingly, in certain variations, a method of the invention includes treating bone marrow cell (BMC) allograft rejection in a human subject by administering to the human subject, in an amount effective to inhibit NK cell activity and thereby treat the acute BMC allograft rejection, an antibody that (a) specifically binds to a polypeptide segment having the amino acid sequence set forth in residues 25-266 of SEQ ID NO:2 and (b) inhibits the interaction of zB7H6 with human NKp30. Particularly suitable antibodies include monoclonal antibodies (e.g., human or humanized monoclonal antibodies). Antibodies for treating BMC can also be single chain antibodies.

In another aspect, the present invention provides methods for inducing antibody dependent cellular cytotoxicity (ADCC) against a zB7H6-expressing cell. Such methods generally include contacting the zB7H6-expressing cell with an effective amount an antibody that specifically binds to a polypeptide segment having the amino acid sequence set forth in residues 25-266 of SEQ ID NO:2, wherein the contacting is in the presence of an NK cell or a CD8$^+$ T cell expressing an Fc receptor having ADCC activity, and wherein the antibody comprises an Fc region capable of binding the Fc receptor. Suitable anti-zB7H6 antibodies include monoclonal antibodies, including, for example, human or humanized monoclonal antibodies, as well as single chain antibodies. In certain variations, the Fc region is a single chain Fc (scFc). The zB7H6-expressing cell can be, for example, a zB7H6-expressing cancer cell. zB7H6 cancer cells particularly amenable to targeted killing using these methods include, e.g., colon cancer cells, liver cancer cells, cervical cancer cells, lung cancer cells, pancreatic cancer cells, prostate cancer cells, prohemocytic leukemia cells, B-cell lymphoma cells, monocytic lymphoma cells, erythroleukemia cells, Burkitt's lymphoma cells, and chronic myelogenous leukemia cells.

In yet another aspect, the present invention provides methods for inducing complement dependent cytotoxicity (CDC) against a zB7H6-expressing cell. Such methods generally include contacting the zB7H6-expressing cell with an effective amount an antibody that specifically binds to a polypeptide segment having the amino acid sequence set forth in residues 25-266 of SEQ ID NO:2, wherein the contacting is in the presence of complement, and wherein the anti-zB7H6 antibody comprises an Fc region having CDC activity. Suitable anti-zB7H6 antibodies include monoclonal antibodies, including, for example, human or humanized monoclonal antibodies, as well as single chain antibodies. In certain variations, the Fc region is a single chain Fc (scFc). The zB7H6-expressing cell can be, for example, a zB7H6-expressing cancer cell. zB7H6 cancer cells particularly amenable to targeted killing using these methods include, e.g., colon cancer cells, liver cancer cells, cervical cancer cells, lung cancer cells, pancreatic cancer cells, prostate cancer cells, prohemocytic leukemia cells, B-cell lymphoma cells, monocytic lymphoma cells, erythroleukemia cells, Burkitt's lymphoma cells, and chronic myelogenous leukemia cells.

In another, related aspect, the present invention provides methods for treating a zB7H6-expressing cancer in a subject. Such methods generally include administering to the subject an effective amount of an antibody that specifically binds to a polypeptide segment having the amino acid sequence set forth in residues 25-266 of SEQ ID NO:2, wherein the antibody comprises an Fc region having ADCC and/or CDC activity. Suitable anti-zB7H6 antibodies include monoclonal antibodies, including, for example, human or humanized monoclonal antibodies, as well as single chain antibodies. In certain variations, the Fc region is a single chain Fc (scFc). zB7H6-expressing cancers particularly amenable to treatment using such methods include, for example, cancers of the colon, liver, cervix, lung, pancreas, and prostate, as well as cancers of the blood such as, e.g., prohemocytic leukemia, B-cell lymphoma, monocytic lymphoma, erythroleukemia, Burkitt's lymphoma, or chronic myelogenous leukemia.

In another aspect, the present invention provides an antibody-drug conjugate comprising an antibody that specifically binds to a polypeptide segment having the amino acid sequence set forth in residues 25-266 of SEQ ID NO:2, wherein the antibody is conjugated to a cytotoxic agent. In certain embodiments, the antibody that binds the amino acid sequence of residues 25-266 of SEQ ID NO:2 is a monoclonal antibody such as, for example, a human or humanized monoclonal antibody. In other variations, the antibody is a single chain antibody. Suitable cytotoxic agents include, for example, anti-tubulin agents, DNA minor groove binding agents, DNA minor groove alkylating agents, duocarmycins, and puromycins. Particularly suitable anti-tubulin agents include, e.g., dolastatins, vinca alkaloids, podophyllatoxins, taxanes, baccatin derivatives, cryptophysins, maytansinoids, and combretastatins.

In typical embodiments of an antibody-drug conjugate as summarize above, the antibody is conjugated to the cytotoxic agent via a linker. Particularly suitable linkers are linker that are cleavable under intracellular conditions, such as, for example, a peptide linker cleavable by an intracellular protease (e.g., cleavable by a lysosomal protease or an endosomal protease). Linkers cleavable under intracellular conditions may include dipeptide linkers, such as, for example, a val-cit linker or a phe-lys linker. In other variations, the cleavable linker is hydrolyzable at a pH of less than 5.5 (e.g., a hydrazone linker). In yet other variations, the cleavable linker is a disulfide linker.

The present invention further includes pharmaceutical composition comprising an antibody-drug conjugate as above and at least one pharmaceutically acceptable carrier.

In yet another aspect, the present invention provides a method for depleting or inhibiting the growth of zB7H6-expressing cells within a cell population comprising said zB7H6-expressing cells. Generally, the method includes contacting said zB7H6-expressing cells with an effective amount of an antibody-drug conjugate as above. In certain embodiments, the method is used in vivo to treat a zB7H6-expressing cancer in a subject by administering to the subject an effective amount of the antibody-drug conjugate. In particular variations, the zB7H6-expressing cancer is a cancer of the colon, liver, cervix, lung, pancreas, or prostate. In yet other variations, the zB7H6-expressing cancer is a prohemocytic leukemia, a B-cell lymphoma, a monocytic lymphoma, a erythroleukemia, Burkitt's lymphoma, or a chronic myelogenous leukemia.

The present invention further provides methods of screening for an antagonist or an agonist of the interaction of zB7H6 with NKp30. For example, in certain embodiments, a method of screening for antagonist of the interaction of zB7H6 with NKp30 generally includes (a) contacting an agent with a zB7H6 polypeptide in the presence of an NKp30 polypeptide; (b) detecting a measure of the interaction of the zB7H6 polypeptide with the NKp30 polypeptide; and (c) determining whether the level of the zB7H6/NKp30 interaction measured in step (b) is significantly less relative to the level of interaction measured for control zB7H6 and NKp30 polypeptides in the absence of the agent, such that if the level of zB7H6/NKp30 interaction is less, then the agent is identified as an antagonist of the interaction of zB7H6 with NKp30. In other embodiments, a method of screening an agent for an agonist of the interaction of zB7H6 with NKp30 generally includes (a) contacting an agent with a zB7H6 polypeptide in the presence of an NKp30 polypeptide; (b) detecting a measure of the interaction of the zB7H6 polypeptide with the NKp30 polypeptide; and (c) determining whether the level of the zB7H6/NKp30 interaction measured in step (b) is significantly greater relative to the level of interaction measured for control zB7H6 and NKp30 polypeptides in the absence of the agent, such that if the level of zB7H6/NKp30 interaction is greater, then the agent is identified as an agonist of the interaction of zB7H6 with NKp30.

BRIEF DESCRIPTION OF THE DRAWINGS

FIGS. 5A and 5B show the coomassie-stained gel and corresponding Western blot juxtaposed.

FIG. 6 depicts the amino acid sequence of protein DKFZP686I21167 (subsequently designated zB7H6), with peptides identified by LC-MS/MS underlined in bold.

FIGS. 13A-13C illustrate the amino acid sequences of certain immunoglobulin Fc polypeptides. Amino acid sequence numbers are based on the EU index (Kabat et al., *Sequences of Proteins of Immunological Interest*, US Department of Health and Human Services, NIH, Bethesda, 1991). The illustrated sequences include a wild-type human sequence ("wt"; SEQ ID NO:29) and five variant sequences, designated Fc-488 (SEQ ID NO:30), Fc4 (SEQ ID NO:31), Fc5 (SEQ ID NO:32), Fc6 (SEQ ID NO:33), and Fc7 (SEQ ID NO:34). The Cys residues normally involved in disulfide bonding to the light chain constant region (LC) and heavy chain constant region (HC) are indicated. A "." indicates identity to wild-type at that position. *** indicates the stop codon; the C-terminal Lys residue has been removed from Fc6. Boundaries of the hinge, $C_H2$, and $C_H3$ domains are shown.

DETAILED DESCRIPTION OF THE INVENTION

I. Overview

The present invention is directed to the identification and characterization of zB7H6, a novel member of the B7 family of cellular receptors, and the discovery of its ability to bind to NKp30. The novel receptor of the present invention is denominated "zB7H6" and is distinct from previously known members of the B7 family such as B7-1, B7-2, B7h2, PD-L1, PD-L2, B7-H3 and B7-H4. Methods and compositions for modulating zB7H6-mediated signaling such as, e.g., modulating the natural interaction of zB7H6 and NKp30 are also provided, having multiple therapeutic applications for immunotherapy, including immunotherapy for, e.g., cancer and infectious disease.

Figure 7:
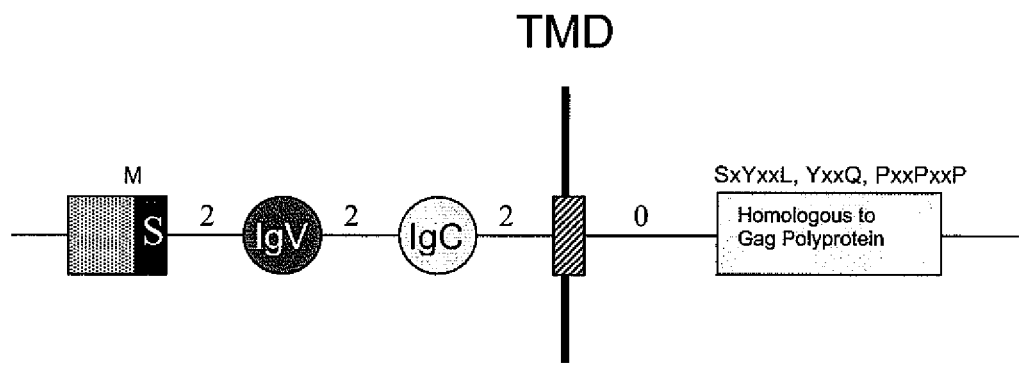
FIG. 7 depicts the gene structure profile of protein DKFZP686I21167 (subsequently designated zB7H6). The gene structure profile is Signal-2-IgV-2-IgC-2-TMD-0-LgEx, where the integers "2" and "0" denote the phasing between exons 1 through 5 coding for, respectively, a leader sequence ("S"), an IgV domain, an IgC domain, a transmembrane domain ("TMD"), and an intracellular domain with homology to Gag polyprotein. "SxYxxL," "YxxQ," and "PxxPxxP" denote potential signaling motifs within the intracellular domain of zB7H6 (respectively, an ITIM motif, an SH2 binding motif, and an SH3 binding motif).

An illustrative nucleotide sequence that encodes human zB7H6 is provided by SEQ ID NO:1; the encoded polypeptide is shown in SEQ ID NO:2. The zB7H6 polypeptide of SEQ ID NO:2 comprises an extracellular domain of approximately 242 amino acid residues (residues 25-266 of SEQ ID NO:2), a transmembrane domain of approximately 18 amino acid residues (residues 267-284 of SEQ ID NO:2), and an intracellular domain of approximately 158 amino acid residues (residues 285-454 of SEQ ID NO:2). zB7H6 also has an IgV domain of approximately 117 amino acid residues (residues 25-141 of SEQ ID NO:2) and an IgC domain of approximately 97 amino acid residues (residues 142-238 of SEQ ID NO:2). There are also several potential signaling motifs within the intracellular domain of zB7H6, including an ITIM motif (SaYtpL, amino acid residues 293-298 of SEQ ID NO:2); an SH2 binding motif (YqlQ, amino acid residues 229-332 of SEQ ID NO:2); and an SH3 binding motif (PdaPilPvsP, amino acid residues 418-427 of SEQ ID NO:2).

zB7H6 was identified as a member of the B7 family of cellular receptors based on B7 family gene profiling. The gene structure profile is Signal-2-IgV-2-IgC-2-TMD-0-LgEx. (See FIG. 7.) The extracellular region of this profile matches a B7 gene structure model, which includes characteristic exon patterns in which the first exon encodes a leader sequence, the second exon encodes an IgV domain and the third exon encodes an IgC domain. Another characteristic feature of the B7 family gene structure is the phasing of the exons: in the region corresponding to the extracellular domain, B7 family members show a conserved phasing of 2 between exons 1 to 4. (See id.)

zB7H6 was identified as a counter-receptor for NKp30, a receptor selectively expressed on mature natural killer (NK) cells and which is involved in human natural cytotoxicity as an activatory receptor. NK cells are typically prevented from attacking normal tissue by the interaction between MHC class I molecules and inhibitory receptors. In the absence, however, of MHC class I expression (such as, for example, on tumor cells or virus-infected cells), ligation of activating receptors on NK cells triggers target-cell killing. Such triggering NK-cell receptors include NKp30, NKp44, NKp46, NKG2D, and DNAM1. The activating target-cell ligand to which NKp30 binds had not been previously identified, and the identification of zB7H6 as the counter-receptor for NKp30 enables a variety of therapeutic agents capable of mimicking or interfering with the interaction of zB7H6 and NKp30 to modulate NK lymphocyte activity for the purpose of treating, among other conditions, cancer, infectious disease, or NK-cell mediated allograft rejection. For example, a reagent that mimics the zB7H6-NKp30 interaction, including a soluble form of zB7H6 comprising the extracellular domain, can be used to facilitate NK cell responses to a tumor or virus-infected cells by activating the NKp30 stimulatory signal. Conversely, an agent that blocks the zB7H6-NKp30 interaction, such as, for example, an anti-zB7H6 antibody that competes for binding with NKp30, can be used to inhibit NK cell-mediated responses such as, for example, in acute bone marrow cell (BMC) allograft rejection.

Accordingly, in one aspect, the present invention provides zB7H6 polypeptides that are useful in the modulation of NK cell activity and in the treatment of disorders such as cancer, infectious disease, or NK cell-mediated allograft rejection. Generally, such zB7H6 polypeptides comprise the zB7H6 extracellular domain (residues 25-266 of SEQ ID NO:2); a functional variant of the zB7H6 extracellular domain having at least 80% (e.g., at least 90% or at least 95%) identity with residues 25-266 of SEQ ID NO:2 and capable of binding to NKp30; or a functional fragment of the aforementioned zB7H6 extracellular domain or domain variant, which fragment is capable of binding to NKp30. In some variations, the zB7H6 polypeptide has the amino acid sequence of residues 25-454 of SEQ ID NO:2 (e.g., the polypeptide of SEQ ID NO:2), or a functional variant of zB7H6 having at least 80% (e.g., at least 90%, or at least 95%) identity with residues 25-454 of SEQ ID NO:2. In certain embodiments, the zB7H6 polypeptide is a soluble zB7H6 polypeptide lacking a functional transmembrane domain. Particularly suitable soluble zB7H6 polypeptides include fusion proteins comprising or consisting of the zB7H6 extracellular domain, or the functional variant or fragment thereof, and a heterologous polypeptide. In some such variations, the heterologus polypeptide is an immunoglobulin moiety; a particularly suitable immunoglobulin moiety is an immunoglobulin heavy chain constant region, such as a human $F_c$ fragment. In other variations, the heterologous polypeptide is a vasodialator-stimulated phosphoprotein (VASP) domain, which is particularly suitable for preparation of multimeric (e.g., tetrameric) forms of soluble zB7H6. In some embodiments, the soluble fusion protein further includes a polypeptide linker.

The present invention also provides polynucleotides, including vectors, encoding soluble zB7H6 polypeptides of the invention, as well as host cells comprising such polynucleotides. In some aspects of the invention, such polynucleotides, vectors, and host cells are used in methods for preparing a soluble zB7H6 protein. Such methods generally include culturing a host cell transformed or transfected with an expression vectors encoding the soluble zB7H6 protein under conditions in which the protein is expressed, and recovering the soluble zB7H6 protein from the host cell.

The present invention further provides antibodies that specifically bind to the extracellular domain of zB7H6. In various embodiments, such antibodies bind to monomeric and/or multimeric forms of zB7H6, including, for example, to monomeric or multimeric forms of soluble zB7H6. Such antibodies include agonist antibodies, neutralizing antibodies, polyclonal antibodies, murine monoclonal antibodies, humanized antibodies derived from murine monoclonal antibodies, human monoclonal antibodies, and antigen-binding fragments thereof. Illustrative antibody fragments include $F(ab')_2$, $F(ab)_2$, Fab', Fab, Fv, scFv, and minimal recognition units. Neutralizing antibodies bind zB7H6 such that its interaction with NKp30 is inhibited or blocked.

The present invention further includes pharmaceutical compositions comprising a pharmaceutically acceptable carrier and a soluble zB7H6 polypeptide or anti-zB7H6 antibody as described herein. Such compositions can be used in therapeutic methods according to the present invention.

In other aspects, the present invention provides methods for modulating NK cell activity using agents that either mimic or block zB7H6 activity. Suitable agents that mimic zB7H6 activity include soluble forms of zB7H6 comprising the extracellular zB7H6 domain, or functional variants or fragments thereof capable of binding to and stimulating NKp30 activity. Alternative agonists include gene therapy vectors capable of recombinantly producing functional zB7H6 molecules intracellularly, small molecule enhancers of zB7H6 expression and/or zB7H6-mediated signaling, and the like. Suitable zB7H6 blocking agents include anti-zB7H6 antibodies capable of binding to at least a portion of the extracellular domain of zB7H6 and interfering with the interaction of zB7H6 with NKp30, small molecule inhibitors of the zB7H6 interaction with NKp30, and the like. Alternative zB7H6 antagonists further include antisense oligonucleotides directed to the zB7H6 nucleic acid sequence, inhibitory RNA sequences, small molecule inhibitors of B7H6 expression and/or intracellular signaling, and the like.

For example, in some embodiments, the present invention provides a method for treating a disease or disorder characterized by insufficient natural killer (NK) cell activity (e.g., a cancer or an infectious disease) by administering to a subject an effective amount of a soluble zB7H6 polypeptide. In other aspects, the present invention provides a method for decreasing human natural killer (NK) cell activity against a zB7H6-expressing cell by contacting the zB7H6-expressing cell, in the presence of a human NK cell, with an effective amount of an antibody that specifically binds to the extracellular domain of zB7H6 and that inhibits the interaction of zB7H6 with human NKp30; such methods can be used, for example, in vivo for treating NK-cell-mediated allograft rejection, particularly acute BMC allograft rejection.

These and other aspects of the invention will become evident upon reference to the following detailed description. In addition, various references are identified below and are incorporated by reference in their entirety.

II. Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551, 1993), cyclic AMP response elements (CREs), serum response elements (SREs; Treisman, *Seminars in Cancer Biol.* 1:47, 1990), glucocorticoid response elements (GREs), and binding sites for other transcription factors, such as CRE/ATF (O'Reilly et al., *J. Biol. Chem.* 267:19938, 1992), AP2 (Ye et al., *J. Biol. Chem.* 269: 25728, 1994), SP1, cAMP response element binding protein (CREB; Loeken, *Gene Expr.* 3:253, 1993) and octamer factors (see generally Watson et al., eds., *Molecular Biology of the Gene*, 4th ed. (The Benjamin/Cummings Publishing Company, Inc. 1987), and Lemaigre and Rousseau, *Biochem. J.* 303:1, 1994). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

In the context of host cell expression of DNA, a "heterologous" peptide or polypeptide is a peptide or polypeptide encoded by a non-host DNA molecule, i.e., a peptide or polypeptide encoded by a heterologous DNA molecule.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces zB7H6 from an expression vector. In contrast, zB7H6 can be produced by a cell that is a "natural source" of zB7H6, and that lacks an expression vector.

"Integrative transformants" are recombinant host cells, in which heterologous DNA has become integrated into the genomic DNA of the cells.

A "fusion protein" is a hybrid protein comprising at least two polypeptide segments that are, relative to each other, derived from different proteins. In this context, "different proteins" means that each protein corresponds to a different gene locus. A protein corresponds to a gene locus if it is encoded by an allele corresponding to the gene locus, or if the protein has at least 80% sequence identity to a protein encoded by such an allele. Polypeptide segments derived from different proteins are also referred to herein as being "heterologous" with respect to each other. Thus, for example, in the context of a fusion protein comprising a zB7H6 polypeptide segment (e.g., the extracellular domain, or a functional variant or fragment thereof) and a second polypeptide segment from a protein different than zB7H6, the second polypeptide segment is also referred to herein as being a "heterologous polypeptide segment" or "heterologous polypeptide." Such heterologous polypeptides include, for example, immunoglobulin constant regions and VASP domains, as further described herein.

The term "receptor" denotes a cell-associated protein that binds to a bioactive molecule termed a "counter-receptor." This interaction mediates the effect of the counter-receptor on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular counter-receptor-binding domain and an intracellular effector domain that is typically involved in signal transduction. In certain membrane-bound receptors, the extracellular counter-receptor-binding domain and the intracellular effector domain are located in separate polypeptides that comprise the complete functional receptor.

In general, the binding of counter-receptor to receptor results in a conformational change in the receptor that causes an interaction between the effector domain and other molecule(s) in the cell, which in turn leads to an alteration in the metabolism of the cell. Metabolic events that are often linked to receptor-counter-receptor interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

A "soluble receptor" is a receptor polypeptide that is not bound to a cell membrane. Soluble receptors are most commonly counter-receptor-binding polypeptides that lack transmembrane and cytoplasmic domains, and other linkage to the cell membrane such as via glycophosphoinositol (GPI). Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Soluble receptors can be monomeric, homodimeric, heterodimeric, or multimeric, with multimeric receptors generally not comprising more than 9 subunits, preferably not comprising more than 6 subunits, and most preferably not comprising more than 3 subunits. Receptor polypeptides are said to be substantially free of transmembrane and intracellular polypeptide segments when they lack sufficient portions of these segments to provide membrane anchoring or signal transduction, respectively. For example, representative soluble receptors for zB7H6 include, for instance the soluble receptor as shown in SEQ ID NO:17 or 19.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, such as 96%, 97%, or 98% or more pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and the like, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/counter-receptor pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

The term "antibody," as used herein, refers to immunoglobulin polypeptides and immunologically active portions of immunoglobulin polypeptides, i.e., polypeptides of the immunoglobulin family, or fragments thereof, that contain an antigen binding site that immunospecifically binds to a specific antigen (e.g., the extracellular domain of zB7H6).

An "anti-idiotype antibody" is an antibody that binds with the variable region domain of an immunoglobulin. In the present context, an anti-idiotype antibody binds with the variable region of an anti-zB7H6 antibody, and thus, an anti-idiotype antibody mimics an epitope of zB7H6.

An "antibody fragment" is a portion of an antibody such as $F(ab')_2$, $F(ab)_2$, Fab', Fab, and the like. Regardless of structure, an antibody fragment binds with the same antigen that is recognized by the intact antibody. For example, an anti-zB7H6 monoclonal antibody fragment binds to an epitope of zB7H6.

The term "antibody" also encompasses genetically engineered intact antibodies or fragments such as, for example, chimeric antibodies, humanized antibodies, "Fv" fragments consisting of the variable regions of the heavy and light chains, polypeptides consisting of the light chain variable region, recombinant single chain antibodies in which light and heavy variable regions are connected by a peptide linker ("scFv proteins"), minimal recognition units consisting of the amino acid residues that mimic the hypervariable region, and the like, as well as synthetic antigen-binding peptides and polypeptides.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain. Construction of humanized antibodies for therapeutic use in humans that are derived from murine antibodies, such as those that bind to or neutralize a human protein, is within the skill of one in the art.

The terms "Fc fragment," "Fc region," or "Fc domain," as used herein, are synonymous and refer to the portion of an antibody that is responsible for binding to antibody receptors on cells and the C1q component of complement. Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc fragment consists of the disulfide-linked heavy chain hinge regions, $C_H2$, and $C_H3$ domains. However, more recently the term has been applied to a single chain consisting of $C_H3$, $C_H2$, and at least a portion of the hinge sufficient to form a disulfide-linked dimer with a second such chain. For a review of immunoglobulin structure and function, see Putnam, *The Plasma Proteins*, Vol. V (Academic Press, Inc., 1987), pp. 49-140; and Padlan, *Mol. Immunol.* 31:169-217, 1994. As used herein, the term Fc includes variants of naturally occurring sequences.

The terms "single chain Fc," "single chain Fc domain," and "scFc," as used herein, are synonymous and refer to a polypeptide fusion comprising two Fc domain monomers joined by a flexible linker, such that the two Fc monomers are capable of dimerization to form a functional, dimeric Fc domain capable of binding Fc receptors. Single chain Fc polypeptides are further described in International PCT Patent Application No. US08/060,852, entitled "Single Chain Fc, Methods of Making, and Methods of Treatment," filed Apr. 18, 2008, the disclosure of which is incorporated by reference herein in its entirety.

The term "Fc region having ADCC activity," as used herein, refers to an Fc domain capable of mediating antibody dependent cellular cytotoxicity (ADCC) through binding of a cytolytic Fc receptor (e.g., FcγRIIIα) on a cytolytic immune effector cell expressing the Fc receptor (e.g., an NK cell or $CD8^+$ T cell).

The term "complement" refers collectively to those components in normal serum that, together with antigen-bound antibodies, exhibit the ability to lyse cells. Complement consists of a group of serum proteins that act in concert and in an orderly sequence to exert their effect.

The terms "classical complement pathway" and "classical complement system," as used herein, are synonymous and refer to a particular pathway for the activation of complement. The classical pathway requires antigen-antibody complexes for initiation and involves the activation, in an orderly fashion, of nine major protein components designated C1 through C9. For several steps in the activation process, the product is an enzyme that catalyzes the subsequent step. This cascade provides amplification and activation of large amounts of complement by a relatively small initial signal.

The term "Fc region having CDC activity," as used herein, refers to an Fc domain capable of mediating complement dependent cytotoxicity (CDC) through binding of C1q complement protein and activation of the classical complement system.

The term "agent" as used herein means an element, compound, or other molecular entity, including, e.g., a pharmaceutical, therapeutic, or pharmacologic compound. Agents can be natural or synthetic or a combination thereof. A "therapeutic agent" is an agent that exerts a therapeutic (e.g., beneficial) effect on a cell or a tissue (e.g., on a cell or tissue expressing zB7H6, such as a zB7H6-expressing cancer cell), either alone or in combination with another agent (e.g., a prodrug converting enzyme in combination with a prodrug). In certain aspects of the present invention, a "therapeutic agent" is an agent conjugated to an antibody to produce a conjugate that is useful for therapy. Examples of therapeutic agents include drugs, toxins, immunomodulators, chelators, boron compounds, photoactive agents or dyes, and radioisotopes. In some variations, a therapeutic agent for conjugation to an antibody is an agent that exerts a cytotoxic or cytostatic effect.

"Cytotoxic effect," in reference to the effect of an agent on a cell, means killing of the cell. "Cytostatic effect" means an inhibition of cell proliferation. A "cytotoxic agent" means an agent that has a cytotoxic or cytostatic effect on a cell, thereby depleting or inhibiting the growth of, respectively, cells within a cell population.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952, 1985), substance P, FLAG peptide (Hopp et al., *Biotechnology* 6:1204, 1988), streptavidin binding peptide, or other antigenic epitope or binding domain. See generally Ford et al., *Protein Expression and Purification* 2:95, 1991. DNA molecules encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

The term "monoclonal antibody" refers to an antibody that is derived from a single cell clone, including any eukaryotic or prokaryotic cell clone, or a phage clone, and not the method by which it is produced. Thus, the term "monoclonal antibody" as used herein is not limited to antibodies produced through hybridoma technology.

As used herein, the term "antibody component" includes both an entire antibody and an antibody fragment.

An "immunoconjugate" is a conjugate of an antibody component with a therapeutic agent or a detectable label.

As used herein, the term "antibody fusion protein" refers to a recombinant molecule that comprises an antibody component and a zB7H6 polypeptide component. Examples of an antibody fusion protein include a protein that comprises a zB7H6 extracellular domain, and either an Fc domain or an antigen-binding region.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "inhibitory polynucleotide" is a DNA or RNA molecule that reduces or prevents expression (transcription or translation) of a second (target) polynucleotide. Inhibitory polynucleotides include antisense polynucleotides, ribozymes, and external guide sequences. The term "inhibitory polynucleotide" further includes DNA and RNA molecules that encode the actual inhibitory species, such as DNA molecules that encode ribozymes.

An "anti-sense oligonucleotide specific for zB7H6" or a "zB7H6 anti-sense oligonucleotide" is an oligonucleotide having a sequence (a) capable of forming a stable triplex with a portion of the zB7H6 gene, or (b) capable of forming a stable duplex with a portion of an mRNA transcript of the zB7H6 gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant zB7H6 gene" refers to nucleic acid molecules that encode a polypeptide having an amino acid sequence that is a modification of SEQ ID NO:2. Such variants include naturally-occurring polymorphisms of zB7H6 genes, as well as synthetic genes that contain conservative amino acid substitutions of the amino acid sequence of SEQ ID NO:2. Additional variant forms of zB7H6 genes are nucleic acid molecules that contain insertions or deletions of the nucleotide sequences described herein. A variant zB7H6 gene can be identified, for example, by determining whether the gene hybridizes with a nucleic acid molecule having the nucleotide sequence of SEQ ID NO:1, or its complement, under stringent conditions.

Alternatively, variant zB7H6 genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art. (See, e.g., Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in *Methods in Gene Biotechnology* 123-151 (CRC Press, Inc. 1997); Bishop (ed.), *Guide to Human Genome Computing* (2nd ed., Academic Press, Inc. 1998).) Two nucleotide or amino acid sequences are considered to have "substantially similar sequence identity" or "substantial sequence identity" if the two sequences have at least 80%, at least 90%, or at least 95% sequence identity relative to each other. Particular methods for determining sequence identity are described below.

Regardless of the particular method used to identify a variant zB7H6 gene or variant zB7H6 polypeptide, a variant gene or polypeptide encoded by a variant gene may be functionally characterized the ability to bind specifically to an anti-zB7H6 antibody. A variant zB7H6 gene or variant zB7H6 polypeptide may also be functionally characterized by the ability to bind to NKp30, using a biological or biochemical assay such as described herein.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

"NK cell activity" as used herein refers to NK cell cytolytic activity. There are numerous assays well-known to the skilled artisan for detecting and/or monitoring such activity, including but not limited to the assays described in the examples provided herein.

As used herein, the phrase "interaction of zB7H6 and NKp30" refers to direct physical interaction (e.g., binding) and/or other indirect interaction of a functional zB7H6 receptor with NKp30 on an NK cell, resulting in stimulation of the zB7H6 receptor and/or NKp30 and associated intracellular signaling.

As used herein, the term "blocking agent" includes those agents that interfere with the interaction of zB7H6 and NKp30, and/or that interfere with the ability of the zB7H6 to trigger NK cell activity, e.g., as measured by cytolytic activity. Exemplary agents include function-blocking antibodies, as well as peptides that block the binding zB7H6 with NKp30 but that fail to stimulate zB7H6-mediated signaling in an NK cell (e.g., zB7H6-derived peptides, peptidomimetics, small molecules, and the like).

As used herein, the term "mimicking agent" includes those agents that mimic the interaction of zB7H6 and NKp30, and/or augment, enhance or increase the ability of zB7H6 and/or NKp30 to trigger NK cell activity. Exemplary agents include zB7H6 soluble receptors, peptides that augment or enhance the ability of zB7H6 to bind to NKp30 or substitute for zB7H6 in stimulating NKp30-mediated signaling (e.g., B7H6-derived peptides, peptidomimetics, small molecules, and the like), and zB7H6 anti-idiotypic antibodies.

The present invention includes functional fragments of zB7H6 polypeptides. Within the context of this invention, a "functional fragment" of a zB7H6 refers to a portion of a zB7H6 polypeptide that at least specifically binds to NKp30. In some embodiments, a functional fragment of zB7H6 is capable of triggering or enhancing NKp30-mediated NK cell activation; in other embodiments, a functional fragment is capable of blocking or decreasing NKp30-mediated NK cell activation.

The term "zB7H6-related agent" or "zB7H6-related composition," as used herein, refers to an agent that demonstrates zB7H6 functional activity or inhibition of zB7H6 functional activity, or an agent that demonstrates zB7H6-specific binding. Such agents include, for example, soluble zB7H6 polypeptides, anti-zB7H6 antibodies, anti-zB7H6 antibody-drug conjugates, zB7H6 anti-idiotypic antibodies or other zB7H6 mimicking agents, zB7H6-encoding polynucleotides, inhibitory polynucleotides, and the like.

The phrase "demonstrates zB7H6 functional activity" or "demonstrates zB7H6 activity," in reference to an agent or composition, refers generally to zB7H6 mimicking agents (including, e.g., soluble zB7H6 polypeptides and zB7H6 anti-idiotypic antibodies) as well as polynucleotides encoding polypeptides that have zB7H6 functional activity.

The phrase "demonstrates inhibition of zB7H6 functional activity," in reference to an agent or composition, refers generally to zB7H6 blocking agents (including, e.g., function-blocking anti-zB7H6 antibodies and peptides that block the binding zB7H6 with NKp30 but that fail to stimulate zB7H6-mediated signaling) as well as nucleic acids that reduce or prevent expression of a zB7H6 gene (i.e., zB7H6 inhibitory polynucleotides).

The term "NK cell-associated disease or disorder," as used herein, refers to generally to NK-cell-mediated diseases or disorders as well as diseases or disorders characterized by insufficient NK cell activity.

The phrase "disease or disorder characterized by insufficient NK cell activity," as used herein, refers to any disease or disorder that involves, at least in part, pathogenic cells that can serve as targets for NK cell cytolytic activity, but which are prominent in the disease or disorder at least partly as a result of having evaded NK cell-mediated cytotoxicity. Such pathogenic cells are typically those lacking MHC class I expression, such as, for example, certain tumor cells or virus-infected cells. Accordingly, typical diseases or disorders characterized by insufficient NK cell activity are cancers and many infectious diseases. Such diseases and disorders are particularly amenable to certain treatment methods for enhancing NK cell activity, as described further herein.

The term "NK cell-mediated disease or disorder," as used herein, refers to any disease or disorder having a pathology that is mediated, at least in part, by NK cell cytolytic activity. An example of such a disease or disorder is acute rejection of bone marrow cell (BMC) allografts. Such diseases or disorder are particularly amenable to certain treatment methods for inhibition NK cell activity, as described further herein.

The term "effective amount," in the context of treatment of a NK cell-associated disease or disorder by administration of a soluble zB7H6 polypeptide or an antibody to a subject as described herein, refers to an amount of such molecule that is sufficient to modulate an NK cell-mediated response in the subject so as to inhibit the occurrence or ameliorate one or more symptoms of the NK cell-associated disease or disorder. An effective amount of an agent is administered according to the methods of the present invention in an "effective regime." The term "effective regime" refers to a combination of amount of the agent being administered and dosage frequency adequate to accomplish treatment or prevention of the disease or disorder.

Due to the imprecision of standard analytical methods, molecular weights and lengths of polymers are understood to be approximate values. When such a value is expressed as "about" X or "approximately" X, the stated value of X will be understood to be accurate to ±10%.

III. zB7H6 Polypeptides, Nucleic Acids, Vectors, Host Cells, and Related Methods for Production The zB7H6 polypeptides of the present invention generally comprise the zB7H6 extracellular domain (residues 25-266 of SEQ ID NO:2), or a functional variant or fragment thereof. Such zB7H6 polypeptides are useful, for example, in the modulation of NK cell activity and in the treatment of disorders such as cancer or infectious disease, as well as in methods of screening agents for activity against the functional interaction of zB7H6 with NKp30. Generally, zB7H6 polypeptides of the invention comprise a polypeptide region selected from the following:

(i) the extracellular domain of the zB7H6 polypeptide of SEQ ID NO:2 (i.e., residues 25-266 of SEQ ID NO:2);
(ii) a functional variant of the zB7H6 extracellular domain of (i), the variant having at least 80% identity with residues 25-266 of SEQ ID NO:2; and
(iii) a functional fragment of the zB7H6 extracellular domain of (i) or of the domain variant of (ii).

In certain embodiments, a zB7H6 polypeptide is a soluble receptor polypeptide. Such soluble forms of zB7H6 lack a functional transmembrane domain and typically are also substantially free of intracellular polypeptide segments. In some alternative embodiments, a zB7H6 polypeptide is a cell membrane-bound form of zB7H6, such as, e.g., a zB7H6 polypeptide comprising a functional transmembrane domain or a GPI linkage. Cell-membrane bound forms of zB7H6 include, for example, full length and substantially full-length forms of zB7H6 protein, such as a polypeptide comprising or consisting of residues 25-454 of SEQ ID NO:2, or a variant thereof.

In some embodiments of a zB7H6 polypeptide comprising a functional extracellular domain variant, the variant has at least 85%, at least 90%, at least 95%, at least 96%, at least 97%, at least 98%, or at least 99% sequence identity with residues 25-266 of SEQ ID NO:2. Similarly, in other embodiments comprising a functional fragment of an extracellular domain variant, the fragment is derived from a variant having at least 85%, at least 90%, at least 95%, at least 96%, at least 97%, at least 98%, or at least 99% sequence identity with residues 25-266 of SEQ ID NO:2. As previously indicated, in certain embodiments, a zB7H6 polypeptide can further comprise transmembrane and intracellular domain components; in some such embodiments, a polypeptide of the invention has at least 85%, at least 90%, at least 95%, at least 96%, at least 97%, at least 98%, or at least 99% sequence identity with residues 25-454 of SEQ ID NO:2.

Percent sequence identity is determined by conventional methods. See, e.g., Altschul et al., *Bull. Math. Bio.* 48:603, 1986, and Henikoff and Henikoff, *Proc. Natl. Acad. Sci. USA* 89:10915, 1992. For example, two amino acid sequences can be aligned to optimize the alignment scores using a gap opening penalty of 10, a gap extension penalty of 1, and the "BLOSUM62" scoring matrix of Henikoff and Henikoff, supra, as shown in Table 1 (amino acids are indicated by the standard one-letter codes). The percent identity is then calculated as: ([Total number of identical matches]/[length of the longer sequence plus the number of gaps introduced into the longer sequence in order to align the two sequences]) (100).

TABLE 1

BLOSUM62 Scoring Matrix

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |

TABLE 1-continued

BLOSUM62 Scoring Matrix

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative zB7H6 variant. The FASTA algorithm is described by Pearson and Lipman, *Proc. Nat'l Acad. Sci. USA* 85:2444, 1988, and by Pearson, *Meth. Enzymol.* 183:63, 1990. Briefly, FASTA first characterizes sequence similarity by identifying regions shared by the query sequence (e.g., residues 25-266 of SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63, 1990.

FASTA can also be used to determine the sequence identity of nucleic acid molecules using a ratio as disclosed above. For nucleotide sequence comparisons, the ktup value can range between one to six, preferably from three to six, most preferably three, with other parameters set as described above.

The present invention includes soluble zB7H6 polypeptides having a conservative amino acid change compared with the amino acid sequence of SEQ ID NO:2 residues 25-266. For example, zB7H6 variants can be obtained that contain one or more amino acid substitutions of SEQ ID NO:2 residues 25-266 in which an alkyl amino acid is substituted for an alkyl amino acid in a zB7H6 amino acid sequence, an aromatic amino acid is substituted for an aromatic amino acid in a zB7H6 amino acid sequence, a sulfur-containing amino acid is substituted for a sulfur-containing amino acid in a zB7H6 amino acid sequence, a hydroxy-containing amino acid is substituted for a hydroxy-containing amino acid in a zB7H6 amino acid sequence, an acidic amino acid is substituted for an acidic amino acid in a zB7H6 amino acid sequence, a basic amino acid is substituted for a basic amino acid in a zB7H6 amino acid sequence, or a dibasic monocarboxylic amino acid is substituted for a dibasic monocarboxylic amino acid in a zB7H6 amino acid sequence. Among the common amino acids, a "conservative amino acid substitution" is illustrated by, for example, a substitution among amino acids within each of the following groups:
(1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. Exemplary groups of conservative amino acid changes are further shown in Table 2 below.

TABLE 2

Conservative amino acid substitutions

| Basic | Acidic | Polar | Hydrophobic | Aromatic | Small |
|---|---|---|---|---|---|
| arginine | glutamate | glutamine | leucine | phenylalanine | glycine |
| lysine | aspartate | asparagine | isoleucine | tryptophan | alanine |
| histidine | | | valine | tyrosine | serine |
| | | | methionine | | threionine |
| | | | | | methionine |

The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915, 1992). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3). Particular variants of zB7H6 are characterized by having at least 80%, at least 90%, at least 95%, at least 96%, at least 97%, at least 98%, or at least 99% sequence identity to the corresponding amino acid sequence (e.g., residues 25-266 of SEQ ID NO:2), wherein the variation in amino acid sequence is due to one or more conservative amino acid substitutions.

A functional zB7H6 variant or fragment polypeptide can be readily identified using routine assays for assessing the ability of the variant or fragment to specifically bind to NKp30 (e.g., human NKp30), and/or assays to assess the ability of the variant or fragment to trigger NKp30-mediated NK cell activation. For example, cells expressing NKp30 can be probed by FACS using soluble zB7H6 polypeptide, which may be directly labeled or detected using a secondary reagent specific for a moiety of the soluble zB7H6 polypeptide (e.g., a fluorophore-conjugated streptavidin to detect biotinylated zB7H6 polypeptide, or a fluorophore-conjugated anti-IgG antibody to detect a zB7H6 fusion protein comprising an Fc fragment). In other variations, functional zB7H6 polypeptides may be identified by their ability to trigger NK cell cytolytic activity against target cells. Exemplary assays for assessing zB7H6-related function of zB7H6 variants and fragments are further described herein.

In certain variations, a soluble zB7H6 polypeptide is a fusion protein comprising the zB7H6 extracellular domain, or the functional variant or fragment thereof, and a heterologous polypeptide. Suitable heterologous polypeptides include immunoglobulin heavy chain constant regions. For example, in some embodiments the immunoglobulin heavy chain constant region is an $F_c$ fragment (e.g., a human $F_c$ fragment), which contains two or three constant region domains and a hinge region but lacks the variable region. (See, e.g., U.S. Pat. Nos. 6,018,026 and 5,750,375 to Sledziewski et al.) Such fusions comprising $F_c$ fragments are typically secreted as multimeric, typically dimeric, molecules wherein the $F_c$ portions are disulfide bonded to each other and two receptor polypeptides are arrayed in closed proximity to each other. As an illustration, U.S. Pat. No. 5,723,125 (Chang et al.) describes a fusion protein comprising a human interferon and a human immunoglobulin $F_c$ fragment. The C-terminus of the interferon is linked to the N-terminus of the $F_c$ fragment by a peptide linker moiety. An example of a peptide linker is a peptide comprising primarily a T cell inert sequence, which is immunologically inert. An illustrative $F_c$ moiety is a human γ4 chain, which is stable in solution and has little or no complement activating activity. Other suitable $F_c$ moieties include variants of the human γ1 chain that lack or have substantially reduced effector function, such as, for example, Fc4 (SEQ ID NO:31), Fc5 (SEQ ID NO:32), Fc6 (SEQ ID NO:33), and Fc7 (SEQ ID NO:34), which are depicted in FIGS. 13A-13C. Accordingly, in some embodiments, the present invention provides a zB7H6 fusion protein that comprises the zB7H6 extracellular domain, or the functional variant or fragment thereof, and an $F_c$ fragment (e.g., a human $F_c$ fragment or variant thereof), wherein the C-terminus of the zB7H6 extracellular domain, or the functional variant or fragment thereof, is attached to the N-terminus of the $F_c$ fragment via a peptide linker.

Other particularly suitable heterologous polypeptides for production of soluble B7H6 fusion proteins include VASP domains. The use of VASP domains in soluble receptor fusion proteins is described in more detail in U.S. Patent Application Publication No. 2007/0254339, which is incorporated by reference herein in its entirety. VASP domains are derived from the VASP gene present in many species. Sequences are selected for their anticipated ability to form coiled-coil protein structure, as this structure is important for the ability to form multimeric protein forms. Particularly desired for the present invention is the ability of coiled-coil proteins to produce tetrameric protein structures. A particularly preferred embodiment utilizes amino acids 342 to 375 of the human VASP sequence, the full-length polypeptide sequence of which is set forth in SEQ ID NO:4. The full length DNA sequence encoding the human VASP protein is set forth in SEQ ID NO:3.

Work with other types of multimerizing sequences, for examples, the leucine zipper, has shown that a limited number of conservative amino acid substitutions (even at the d residue) can be often be tolerated in zipper sequences without the loss of the ability of the molecules to multimerize (Landschulz et al., Science 243:1681-1688, 1989). Thus, conservative changes from the native sequence for the VASP domain are contemplated within the scope of the invention. For example, Table 2, supra, shows exemplary conservative changes that are predicted to be tolerated by the coiled-coil structure.

If more than one fusion protein is being used to produce a hetero-multimeric protein, for example, heterotetramers, the VASP domain that is used can be the same domain for both fusion proteins or different VASP domains, as long as the domains have the ability to associate with each other and form multimeric proteins.

In certain embodiments, the VASP domain is linked at the C terminus of the zB7H6 extracellular domain as shown in residues 25-266 of SEQ ID NO:2 (or to a functional variant or fragment thereof). Additionally, the VASP domain can be located in the middle of the protein, effectively creating a double fusion protein with a VASP domain flanked by two non-VASP polypeptide segments, where at least one of the polypeptide segments flanking the VASP domain is the zB7H6 extracellular domain as shown in residues 25-266 of SEQ ID NO:2 (or to a functional variant or fragment thereof). In some variations, the second polypeptide segment flanking the VASP domain is a polypeptide segment designed to target the soluble receptor to specific cells or tissues for the benefit of zB7H6 binding activity.

One result of the use of multimerizing heterologous polypeptide sequences in soluble zB7H6 fusion constructs is the ability to increase the affinity or avidity of zB7H6 for a ligand or counter-receptor (e.g., NKp30) through the formation of a multimeric form. By avidity, it is meant the strength of binding of multiple molecules to a larger molecule, a situation exemplified but not limited to the binding of a complex antigen by an antibody. By affinity, it is meant the strength of binding of a simple receptor-ligand system. Such a characteristic would be improved, for example, by forming a binding site with better binding characteristics for zB7H6 through multimerization of the receptor. Avidity and affinity can be measured using standard assays well known to one of ordinary skill. An improvement in affinity or avidity occurs when the affinity or avidity value (for example, affinity constant or $K_a$) for the multimeric soluble zB7H6 fusion protein and a ligand or counter-receptor is higher than for a monomeric zB7H6 polypeptide and the ligand or counter-receptor. An alternative means of measuring these characteristics is the equilibrium constant ($K_d$) where a decrease would be observed with the improvement in affinity or avidity using a multimerizing heterologous polypeptide (e.g., a VASP tetramerization domain).

Polypeptide segments of a soluble zB7H6 fusion protein (e.g., a zB7H6 extracellular domain, or functional variant or fragment thereof, and a segment heterologous to zB7H6) may be linked directly to another protein to form the fusion protein; alternatively, the polypeptide segments may be separated by a distance sufficient to ensure that the proteins form proper secondary and tertiary structure needed for biological activity. Suitable linker sequences will adopt a flexible extended confirmation and will not exhibit a propensity for developing an ordered secondary structure which could interact with the functional domains of the fusions proteins, and will have minimal hydrophobic or charged character which could also interfere with the function of fusion domains. Linker sequences should be constructed with the 15 residue repeat in mind, as it may not be in the best interest of producing a biologically active protein to tightly constrict the N or C terminus of the heterologous sequence. Beyond these considerations, the length of the linker sequence may vary without significantly affecting the biological activity of the fusion protein. Linker sequences can be used between any and all components of the fusion protein (or expression construct) including affinity tags and signal peptides. An example linker is the GSGG sequence (SEQ ID NO:5).

A soluble zB7H6 fusion protein can further include an affinity tag. Such tags do not alter the biological activity of fusion proteins, are highly antigenic, and provide an epitope that can be reversibly bound by a specific binding molecule, such as a monoclonal antibody, facilitating rapid detection and purification of an expressed fusion protein. Affinity tags can also convey resistance to intracellular degradation if proteins are produced in bacteria, such as E. coli. An exemplary affinity tag is the FLAG Tag (SEQ ID NO:6) or the HIS$_6$ Tag (SEQ ID NO:7). Methods of producing fusion proteins utilizing this affinity tag for purification are described in U.S. Pat. No. 5,011,912.

In some variations, a soluble zB7H6 receptor comprises a "targeting domain," a heterologous polypeptide segment designed to target the soluble receptor to specific cells or tissues for the benefit of zB7H6 binding activity. For example, in some embodiments, the soluble fusion protein comprises a polypeptide segment that specifically targets the fusion protein to tumor cells. Particularly suitable heterologous polypeptide segments for targeting fusion proteins to particular cells or tissues include antibodies or antigen-binding fragments thereof that recognize cell surface markers associated with the target cells or tissues. The use of targeting domains can provide a high local concentration of a soluble zB7H6 receptor in the vicinity of a target tissue (e.g., a tumor), thereby reducing the amount of soluble receptor that must be administered to effect a desired response as well as minimizing undesired side effects that may be caused by exposure of non-target tissues to the soluble receptor. In addition, the binding of a targeting domain portion of a zB7H6 fusion protein to the surface of a target cell may enhance cross-linking of zB7H6-bound NKp30 on the surface of NK cells, thereby further enhancing NKp30-mediated stimulation of NK cell activity against the target cell.

For example, in the case of a tumor target tissue, targeting domains can include tumor-specific or tumor-associated antigens (i.e., antigens that are expressed by tumor cells but not normal cells, or antigens that are expressed at high levels in tumor cells relative to normal cells). Examples of such antigens include epidermal growth factor receptor family members (e.g., EGFR and Her2), carcinoembryonic antigen (CEA), members of the mucin family (MUC1), mesothelin, follate receptor, and others. Antigens that are specific to or associated with hematopoietic tumors could also be targeted, including, for example, CD30, CD33, CD40, CD72, and others. Antibodies against all these antigens are either approved or in clinical trials for the treatment of multiple cancers. A zB7H6 fusion protein comprising an antibody against at least one of these surface receptors would enable local targeting of the molecule, and could further facilitate cross-linking of zB7H6-bound NKp30 on the surface of NK cells, thereby further enhancing NKp30-mediated stimulation of NK cell activity against tumor cells.

The present invention further provides a variety of other polypeptide fusions. For example, in some embodiments, a zB7H6 polypeptide can be fused to two or more moieties or domains, such as an affinity tag for purification and a targeting domain. Polypeptide fusions can also comprise one or more cleavage sites, particularly between domains. See, e.g., Tuan et al., *Connective Tissue Research* 34:1 (1996).

In some variations, a zB7H6 polypeptide further comprises a signal sequence or leader sequence. These sequences are generally utilized to allow for secretion of the fusion protein from the host cell during expression and are also known as a leader sequence, prepro sequence or pre sequence. While the secretory signal sequence may be derived from zB7H6, a suitable signal sequence may also be derived from another secreted protein (e.g., the tissue-type plasminogen activator (t-PA) signal sequence, as described, for example, in U.S. Pat. No. 5,641,655) or synthesized de novo. The secretory signal sequence is operably linked to a zB7H6-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., U.S. Pat. No. 5,037,743 to Welch et al.; U.S. Pat. No. 5,143,830 to Holland et al.)

Although the secretory signal sequence of zB7H6 or another protein produced by mammalian cells (e.g., tissue-type plasminogen activator signal sequence, as described, for example, in U.S. Pat. No. 5,641,655) is useful for expression of zB7H6 in recombinant mammalian hosts, a yeast signal sequence is preferred for expression in yeast cells. Examples of suitable yeast signal sequences are those derived from yeast mating phermone α-factor (encoded by the MFα1 gene), invertase (encoded by the SUC2 gene), or acid phosphatase (encoded by the PHO5 gene). See, e.g., Romanos et al., "Expression of Cloned Genes in Yeast," in *DNA Cloning 2: A Practical Approach*, 2$^{nd}$ Edition, Glover and Hames (eds.), pages 123-167 (Oxford University Press 1995).

In some variations, zB7H6 polypeptides are chemically modified via linkage to a polymer. Typically, the polymer is water soluble so that the zB7H6 polypeptide conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. The polymer may be branched or unbranched. A zB7H6 polypeptide conjugate can also comprise a mixture of such water-soluble polymers. General methods for producing conjugates comprising a polypeptide and water-soluble polymer moieties are known in the art. (See, e.g., U.S. Pat. No. 5,382,657 to Karasiewicz et al.; U.S. Pat. No. 5,738,846 to Greenwald et al.; Nieforth et al., *Clin. Pharmacol. Ther.* 59:636, 1996; Monkarsh et al., *Anal. Biochem.* 247:434, 1997.) Such methods can be employed for making zB7H6-comprising homodimeric, heterodimeric or multimeric soluble receptor conjugates.

One example of a zB7H6 polypeptide conjugate comprises a polyalkyl oxide moiety attached to the N-terminus of the zB7H6 polypeptide. PEG is one suitable polyalkyl oxide. As an illustration, zB7H6 can be modified with PEG, a process known as "PEGylation." PEGylation of zB7H6 can be carried out by any of the PEGylation reactions known in the art. (See, e.g., EP 0 154 316; Delgado et al., *Critical Reviews in Therapeutic Drug Carrier Systems* 9:249, 1992; Duncan and Spreafico, *Clin. Pharmacokinet.* 27:290, 1994; Francis et al., *Int J Hematol* 68:1, 1998.) For example, PEGylation can be performed by an acylation reaction or by an alkylation reaction with a reactive polyethylene glycol molecule. In an alternative approach, zB7H6 conjugates are formed by condensing activated PEG, in which a terminal hydroxy or amino group of PEG has been replaced by an activated linker. (See, e.g., U.S. Pat. No. 5,382,657 to Karasiewicz et al.) For PEGylation reactions, the typical molecular weight of a polymer molecule is about 2 kDa to about 100 kDa, about 5 kDa to about 50 kDa, or about 12 kDa to about 25 kDa. The molar ratio of water-soluble polymer to zB7H6 will generally be in the range of 1:1 to 100:1. Typically, the molar ratio of water-soluble polymer to zB7H6 will be 1:1 to 20:1 for polyPEGylation, and 1:1 to 5:1 for monoPEGylation.

zB7H6 polypeptides can be used, for example, to affinity purify a cognate counter-receptor (e.g., NKp30) from solution, or as an in vitro assay tool. For example, the presence of a zB7H6 counter-receptor in a biological sample can be detected using a zB7H6-immunoglobulin fusion protein, in which the zB7H6 moiety is used to bind the counter-receptor, and a macromolecule, such as Protein A or anti-Fc antibody, is used to bind the fusion protein to a solid support. Such systems can be used to identify agonists and antagonists that interfere with the binding of zB7H6 to its counter-receptor (e.g., NKp30).

zB7H6 polypeptides can also be used to trigger or enhance signals in vitro by specifically binding NKp30 on cells, and as agonists in vivo by administering them parenterally (e.g., by intramuscular, subcutaneous or intravenous injection) to bind NKp30 on cells and trigger or enhance NKp30-mediated activation of NK cells. For example, a soluble zB7H6 fusion protein can be used for triggering or enhancing NK cell cytolytic activity in vitro, or for triggering or enhancing such activity ex vivo or in vivo for treatment of cancer or infectious disease. These and other uses are described further herein.

Using methods as discussed herein, one of ordinary skill in the art can prepare a variety of zB7H6 polypeptides as described herein, including polypeptides that comprise the zB7H6 extracellular domain of SEQ ID NO:2 residues 25-266, or a zB7H6 extracellular domain substantially identical thereto and retaining the NKp30-binding or other functional properties of SEQ ID NO:2 residues 25-266. The zB7H6 polypeptides of the invention are typically recombinantly produced, although such polypeptides can also be produced by other methods generally available in the art (e.g., synthetic production of polypeptides, or by isolation of zB7H6 polypeptides from natural sources). Recombinant zB7H6 receptor polypeptides can generally be prepared by expressing a polynucleotide comprising a DNA segment encoding the zB7H6 polypeptide. For example, recombinant zB7H6 soluble receptor polypeptides can generally be prepared by expressing a polynucleotide comprising a truncated DNA encoding the extracellular domain of the zB7H6 polypeptide of SEQ ID NO:2 (contiguous amino acid residues 25-266 of SEQ ID NO:2), or a functional variant or fragment thereof. As it is preferred that the soluble extracellular domain polypeptides be prepared in a form substantially free of transmembrane and intracellular polypeptide segments, polynucleotides encoding such a soluble polypeptide will typically lack regions encoding such transmembrane and intracellular segments. Methods for recombinant production of protein are generally well-known in the art.

As discussed above, soluble zB7H6 polypeptides may also include additional polypeptide segments as generally disclosed herein. In the case of soluble zB7H6 fusion proteins, such embodiments can also be prepared by methods generally known to those skilled in the art. For example, fusion proteins can be prepared by preparing each component of the fusion protein and chemically conjugating them. General methods for enzymatic and chemical cleavage of fusion proteins are described, for example, by Ausubel (1995) at pages 16-19 to 16-25. Alternatively, a polynucleotide encoding both components of the fusion protein in the proper reading frame can be generated using known techniques and recombinantly expressed using methods such as further described further herein.

As indicated above, zB7H6 receptor polypeptides can generally be prepared by expressing a polynucleotide comprising a DNA segment encoding the zB7H6 polypeptide. For soluble protein forms, it is preferred that the extracellular domain polypeptide be prepared in a form substantially free of transmembrane and intracellular polypeptide segments. To direct the export of the receptor domain from the host cell, the receptor DNA is linked to a second DNA segment encoding a secretory peptide, such as a t-PA secretory peptide. In some embodiments, to facilitate purification of the secreted receptor domain, a C-terminal extension, such as a poly-histidine tag, substance P, FLAG™ peptide (Hopp et al., *Biotechnology* 6:1204-1210, 1988; available from Eastman Kodak Co., New Haven, Conn.) or another polypeptide or protein for which an antibody or other specific binding agent is available, can be fused to the receptor polypeptide.

Accordingly, in another aspect, the present invention further provides polynucleotides encoding any of the zB7H6 polypeptides as described herein. Generally, polynucleotides encoding a soluble zB7H6 polypeptide comprises a polynucleotide region encoding the extracellular zB7H6 domain of residues 25-266 of SEQ ID NO:2, or a functional variant or fragment thereof. In certain other variations, a polynucleotide of the invention encodes a cell-membrane bound form of zB7H6, such as a polypeptide comprising residues 25-454 or 1-454 of SEQ ID NO:2, or a functional variant thereof. In a specific embodiment, a polynucleotide encoding a soluble zB7H6 polypeptide comprises nucleotide residues 73-798 or 1-798 of SEQ ID NO:1; examples of polynucleotides encoding residues 25-454 or 1-454 of SEQ ID NO:2 include polynucleotides comprising 73-1362 or 1-1362 of SEQ ID NO:1. In certain variations, polynucleotides of the invention further include one or more polynucleotide regions encoding additional component(s) of a zB7H6 polypeptide, such as, for example, a heterologous polypeptide component of a zB7H6 fusion protein, a signal secretory sequence, and/or an affinity tag.

As will be appreciated by those in the art, due to the degeneracy of the genetic code, an extremely large number of nucleic acids may be made, all of which encode the zB7H6 polypeptides of the present invention. Thus, given a particular amino acid sequence of a zB7H6 polypeptide, any number of different nucleic acids encoding the polypeptide can be made using known techniques to modify the sequence of one or more codons in a way which does not change the amino acid sequence of a zB7H6 polypeptide.

A zB7H6-encoding cDNA can be isolated by a variety of methods, such as by probing with a complete or partial human cDNA or with one or more sets of degenerate probes based on the disclosed sequences. A cDNA can also be cloned using the polymerase chain reaction with primers designed from the representative human zB7H6 sequences disclosed herein. In addition, a cDNA library can be used to transform or transfect host cells, and expression of the cDNA of interest can be detected with an antibody to zB7H6 polypeptide.

For example, nucleic acid molecules encoding a human zB7H6 gene can be obtained by screening a human cDNA or genomic library using polynucleotide probes based upon SEQ ID NO:1. These techniques are standard and well-established, and may be accomplished using cloning kits available by commercial suppliers. See, e.g., Ausubel et al. (eds.), *Short Protocols in Molecular Biology* (3rd ed., John Wiley & Sons 1995); Wu et al., *Methods in Gene Biotechnology*, CRC Press, Inc. 1997; Aviv and Leder, *Proc. Nat'l Acad. Sci. USA* 69:1408, 1972; Huynh et al., "Constructing and Screening cDNA Libraries in λgt10 and λgt11," in *DNA Cloning: A Practical Approach Vol. 1*, Glover (ed.), page 49 (IRL Press, 1985).

Nucleic acid molecules that encode a human zB7H6 gene can also be obtained using the polymerase chain reaction (PCR) with oligonucleotide primers having nucleotide sequences that are based upon the nucleotide sequences of the zB7H6 gene or cDNA. General methods for screening libraries with PCR are provided by, for example, Yu et al., "Use of the Polymerase Chain Reaction to Screen Phage Libraries," in *Methods in Molecular Biology*, Vol. 15: *PCR Protocols: Current Methods and Applications* (White, ed., Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology*, Vol. 15: *PCR Protocols: Current Methods and Applications* (White, ed., Humana Press, Inc. 1993). As an alternative, a zB7H6 gene can be obtained by synthesizing nucleic acid molecules using mutually priming long oligonucleotides and the nucleotide sequences described herein (see, e.g., Ausubel, supra). Established techniques using the polymerase chain reaction provide the ability to synthesize DNA molecules at least two kilobases in length. (See, e.g., Adang et al., *Plant Molec. Biol.* 21:1131, 1993; Bambot et al., *PCR Methods and Applications* 2:266, 1993; Dillon et al., "Use of the Polymerase Chain Reaction for the Rapid Construction of Synthetic Genes," in *Methods in Molecular Biology*, Vol. 15: *PCR Protocols: Current Methods and Applications* 263-268 (White, ed., Humana Press, Inc. 1993); and Holowachuk et al., *PCR Methods Appl.* 4:299, 1995.) For reviews on polynucleotide synthesis, see, for example, Glick and Pasternak, *Molecular Biotechnology, Principles and Applications of Recombinant DNA* (ASM Press 1994); Itakura et al., *Annu. Rev. Biochem.* 53:323, 1984; and Climie et al., *Proc. Nat'l Acad. Sci. USA* 87:633, 1990.

As previously discussed, those skilled in the art will readily recognize that, in view of the degeneracy of the genetic code, considerable sequence variation is possible among these polynucleotide molecules. Thus, the present invention contemplates zB7H6 polypeptide-encoding nucleic acid molecules comprising degenerate nucleotides of SEQ ID NO:1, and their RNA equivalents. The degenerate codons, encompassing all possible codons for a given amino acid, are set forth in Table 3.

TABLE 3

Amino Acids and Corresponding Degenerate Codons

| Amino Acid | One Letter Code | Codons | Degenerate Codon |
|---|---|---|---|
| Cys | C | TGC TGT | TGY |
| Ser | S | AGC AGT TCA TCC TCG TCT | WSN |

TABLE 3-continued

Amino Acids and Corresponding Degenerate Codons

| Amino Acid | One Letter Code | Codons | Degenerate Codon |
|---|---|---|---|
| Thr | T | ACA ACC ACG ACT | CAN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

With regard to expression in particular host cells, different species can exhibit "preferential codon usage." See generally Grantham et al., *Nucl. Acids Res.* 8:1893, 1980; Haas et al. *Curr. Biol.* 6:315, 1996; Wain-Hobson et al., *Gene* 13:355, 1981; Grosjean and Fiers, *Gene* 18:199, 1982; Holm, *Nuc. Acids Res.* 14:3075, 1986; Ikemura, *J. Mol. Biol.* 158:573, 1982; Sharp and Matassi, *Curr. Opin. Genet. Dev.* 4:851, 1994; Kane, *Curr. Opin. Biotechnol.* 6:494, 1995; and Makrides, *Microbiol. Rev.* 60:512, 1996. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species.

Therefore, the degenerate codon sequences disclosed herein serve as a template for optimizing expression of polynucleotides in various cell types and species commonly used in the art and disclosed herein. Sequences containing preferential codons can be tested and optimized for expression in various species, and tested for functionality as disclosed herein.

Those skilled in the art will recognize that the sequence disclosed in SEQ ID NO:1 represents a single allele of human zB7H6, and that allelic variation and alternative splicing are expected to occur. Allelic variants of this sequence can be cloned by probing cDNA or genomic libraries from different individuals according to standard procedures. Allelic variants of the nucleotide sequences disclosed herein, including those containing silent mutations and those in which mutations result in amino acid sequence changes, are within the scope of the present invention, as are proteins which are allelic variants of the amino acid sequences disclosed herein. cDNA molecules generated from alternatively spliced mRNAs, encoding zB7H6 polypeptides that retain the properties of the zB7H6 polypeptide of SEQ ID NO:2 (e.g., variants of the extracellular domain of SEQ ID NO:2 residues 25-266 that retain NKp30-binding capability), are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Variant zB7H6 nucleic acid molecules can be identified using techniques generally known in the art. Suitable criteria for identification of such variants include (a) a determination of the sequence identity or similarity between the encoded polypeptide with the amino acid sequence of SEQ ID NO:2, or a region thereof corresponding to the B7H6 extracellular domain of SEQ ID NO:2 residues 25-266; and (b) a hybridization assay. Such zB7H6 nucleic acid variants include nucleic acid molecules that (1) remain hybridized with a nucleic acid molecule having the nucleotide sequence of SEQ ID NO:1 (or its complement, or a fragment comprising SEQ ID NO:1 residues 73-798) under stringent washing conditions, in which the wash stringency is equivalent to 0.5×-2× SSC with 0.1% SDS at 55-65° C.; and (2) encode a polypeptide having at least 80%, at least 85%, at least 90%, at least 95%, at least 96%, at least 97%, at least 98%, or at least 99% sequence identity to the amino acid sequence of SEQ ID NO:2, or to residues 25-266 of SEQ ID NO:2. Alternatively, zB7H6 variants can be characterized as nucleic acid molecules that (1) remain hybridized with a nucleic acid molecule having the nucleotide sequence of SEQ ID NO: 1 (or its complement, or a fragment comprising SEQ ID NO:1 residues 73-798) under highly stringent washing conditions, in which the wash stringency is equivalent to 0.1×-0.2×SSC with 0.1% SDS at 50-65° C., and (2) encode a polypeptide having at least 80%, at least 85%, at least 90%, at least 95%, at least 96%, at least 97%, at least 98%, or at least 99% sequence identity to the amino acid sequence of SEQ ID NO:2, or to residues 25-266 of SEQ ID NO:2.

In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Following hybridization, the nucleic acid molecules can be washed to remove non-hybridized nucleic acid molecules under stringent conditions, or under highly stringent conditions. See, e.g., Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227, 1990). Sequence analysis software such as OLIGO 6.0 (LSR; Long Lake, Minn.) and Primer Premier 4.0 (Premier Biosoft International; Palo Alto, Calif.), as well as sites on the Internet, are available tools for analyzing a given sequence and calculating $T_m$ based on user-defined criteria. It is well within the abilities of one skilled in the art to adapt hybridization and wash conditions for use with a particular polynucleotide hybrid.

Percent sequence identity can be readily determined by conventional methods such as described supra.

In some embodiments, variants of zB7H6 are characterized by having at least 80%, at least 90%, at least 95%, at least 96%, at least 97%, at least 98%, or at least 99% sequence identity to the corresponding amino acid sequence (e.g., residues 25-266 of SEQ ID NO:2), wherein the variation in amino acid sequence is due to one or more conservative amino acid substitutions. Conservative amino acid changes in a zB7H6-encoding polynucleotide can be introduced, for example, by substituting nucleotides for the nucleotides recited in SEQ ID NO:1. Such "conservative amino acid" variants can be obtained by oligonucleotide-directed mutagenesis, linker-scanning mutagenesis, mutagenesis using the polymerase chain reaction, and the like (see Ausubel (1995); and McPherson (ed.), *Directed Mutagenesis: A Practical Approach* (IRL Press 1991)). As noted supra, a functional zB7H6 variant polypeptide can be identified by the ability to specifically bind to NKp30 (e.g., human NKp30), and/or assays to assess the ability of the variant or fragment to trigger NKp30-mediated NK cell activation.

The zB7H6 polypeptides of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. (See, e.g., Robertson et al., *J. Am. Chem. Soc.* 113:2722, 1991; Ellman et al., *Methods Enzymol.* 202:301, 1991; Chung et al., *Science* 259:806, 1993; and Chung et al., *Proc. Nat'l Acad. Sci. USA* 90:10145, 1993.) In a second method, translation is carried out in *Xenopus* oocytes by microinjection of mutated mRNA and chemically aminoacylated suppressor tRNAs. (See Turcatti et al., *J. Biol. Chem.* 271:19991, 1996.) Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (See Koide et al., *Biochem.*

33:7470, 1994.) Also, naturally occurring amino acid residues can be converted to non-naturally occurring species by in vitro chemical modification. Chemical modification can be combined with site-directed mutagenesis to further expand the range of substitutions. (See Wynn and Richards, *Protein Sci.* 2:395, 1993.)

A limited number of non-conservative amino acids, amino acids that are not encoded by the genetic code, non-naturally occurring amino acids, and unnatural amino acids may be substituted for zB7H6 amino acid residues.

Essential amino acids in the polypeptides of the present invention can be identified according to procedures known in the art, such as site-directed mutagenesis or alanine-scanning mutagenesis. (See, e.g., Cunningham and Wells, *Science* 244: 1081, 1989; Bass et al., *Proc. Nat'l Acad. Sci. USA* 88:4498, 1991; Coombs and Corey, "Site-Directed Mutagenesis and Protein Engineering," in *Proteins: Analysis and Design* 259-311 (Angeletti, ed., Academic Press, Inc. 1998.) In the latter technique, single alanine mutations are introduced at every residue in the molecule, and the resultant mutant molecules are tested for biological activity (e.g., NKp30-binding and/or the ability of the variant or fragment to trigger NKp30-mediated NK cell activation) to identify amino acid residues that are critical to the activity of the molecule. (See, e.g., Hilton et al., *J. Biol. Chem.* 271:4699, 1996.)

Although sequence analysis can be used to further define the zB7H6 NKp30-binding region, amino acids that play a role in zB7H6 binding to NKp30 can also be determined by physical analysis of structure, as determined by such techniques as nuclear magnetic resonance, crystallography, electron diffraction or photoaffinity labeling, in conjunction with mutation of putative contact site amino acids. (See, e.g., de Vos et al., *Science* 255:306, 1992; Smith et al., *J. Mol. Biol.* 224:899, 1992; and Wlodaver et al., *FEBS Lett.* 309:59, 1992.)

Multiple amino acid substitutions can be made and tested using known methods of mutagenesis and screening, such as those disclosed by Reidhaar-Olson and Sauer (*Science* 241: 53, 1988) or Bowie and Sauer (*Proc. Nat'l Acad. Sci. USA* 86:2152, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (see, e.g., Lowman et al., *Biochem.* 30:10832, 1991; U.S. Pat. No. 5,223,409 to Ladner et al.; International Publication No. WO 92/06204 (Huse)) and region-directed mutagenesis (see, e.g., Derbyshire et al., *Gene* 46:145, 1986; Ner et al., *DNA* 7:127, 1988).

Variants zB7H6 nucleotide and polypeptide sequences can also be generated through DNA shuffling. (See, e.g., Stemmer, *Nature* 370:389, 1994; Stemmer, *Proc. Nat'l Acad. Sci. USA* 91:10747, 1994; International Publication No. WO 97/20078.) Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides (e.g., polypeptides that specifically bind NKp30) can be recovered from the host cells and rapidly sequenced using modern equipment. These methods allow the rapid determination of the importance of individual amino acid residues in a polypeptide of interest, and can be applied to polypeptides of unknown structure.

As previously discussed, the present invention also includes "functional fragments" of the zB7H6 extracellular domain and nucleic acid molecules encoding such functional fragments. Routine deletion analyses of nucleic acid molecules can be performed to obtain functional fragments of a nucleic acid molecule encoding a zB7H6 extracellular domain. As an illustration, DNA molecules having the nucleotide sequence of residues 73-798 of SEQ ID NO:1 can be digested with Bal31 nuclease to obtain a series of nested deletions. The fragments are then inserted into expression vectors in proper reading frame, and the expressed polypeptides are isolated and tested for the ability to bind NKp30. One alternative to exonuclease digestion is to use oligonucleotide-directed mutagenesis to introduce deletions or stop codons to specify production of a desired fragment. Alternatively, particular fragments of a zB7H6 gene can be synthesized using the polymerase chain reaction.

This general approach is exemplified by studies on the truncation at either or both termini of interferons. (See Horisberger and Di Marco, *Pharmac. Ther.* 66:507, 1995.) Moreover, standard techniques for functional analysis of proteins are described by, for example, Treuter et al., *Molec. Gen. Genet.* 240:113, 1993; Content et al., "Expression and preliminary deletion analysis of the 42 kDa 2-5A synthetase induced by human interferon," in *Biological Interferon Systems, Proceedings of ISIR-TNO Meeting on Interferon Systems* 65-72 (Cantell, ed., Nijhoff 1987); Herschman, "The EGF Receptor," in *Control of Animal Cell Proliferation, Vol.* 1 169-199 (Boynton et al., eds., Academic Press 1985); Coumailleau et al., *J. Biol. Chem.* 270:29270, 1995; Fukunaga et al., *J. Biol. Chem.* 270:25291, 1995; Yamaguchi et al., *Biochem. Pharmacol.* 50:1295, 1995; and Meisel et al., *Plant Molec. Biol.* 30:1, 1996.

The present invention also includes functional fragments of a zB7H6 polynucleotide encoding a polypeptide that has amino acid changes relative to the amino acid sequence of SEQ ID NO:2 (e.g., changes relative to residues 25-266 of SEQ ID NO:2). A variant zB7H6 gene can be identified on the basis of structure by determining the level of identity with disclosed nucleotide and amino acid sequences, as discussed above. An alternative approach to identifying a variant gene on the basis of structure is to determine whether a nucleic acid molecule encoding a potential variant zB7H6 gene can hybridize to a nucleic acid molecule comprising a nucleotide sequence, such as SEQ ID NO:1.

Polynucleotide molecules comprising a polynucleotide sequence provided herein are propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. To express a zB7H6 gene, a nucleic acid molecule encoding the polypeptide, operably linked to regulatory sequences that control transcriptional expression in an expression vector, is introduced into a host cell. In addition to transcriptional regulatory sequences, such as promoters and enhancers, expression vectors can include translational regulatory sequences and a marker gene which is suitable for selection of cells that carry the expression vector. The gene product encoded by a polynucleotide of the invention is expressed in any convenient expression system, including, for example, bacterial, yeast, insect, amphibian and mammalian systems. Suitable vectors and host cells are described, e.g., in U.S. Pat. No. 5,654,173. In the expression vector, the zB7H6 polypeptide-encoding polynucleotide is linked to a regulatory sequence as appropriate to obtain the desired expression properties. These can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. Accordingly, the expression vector will generally provide a transcriptional and translational initiation region, which may be inducible or constitutive, where the coding region is operably linked under the transcriptional control of the transcriptional initiation region, and a transcriptional and translational termination region. These control regions may be native to the DNA encoding the zB7H6 polypeptide or may be derived from exogenous sources.

The expression cassettes may be introduced into a variety of vectors, e.g., plasmid, BAC, YAC, bacteriophage such as lambda, P1, M13, etc., plant or animal viral vectors (e.g., retroviral-based vectors, adenovirus vectors), and the like, where the vectors are normally characterized by the ability to provide selection of cells comprising the expression vectors. The vectors may provide for extrachromosomal maintenance, particularly as plasmids or viruses, or for integration into the host chromosome. Where extrachromosomal maintenance is desired, an origin sequence is provided for the replication of the plasmid, which may be low- or high copy-number. A wide variety of markers are available for selection, particularly those which protect against toxins, more particularly against antibiotics. The particular marker that is chosen is selected in accordance with the nature of the host, where in some cases, complementation may be employed with auxotrophic hosts. Introduction of the DNA construct may use any convenient method, including, e.g., conjugation, bacterial transformation, calcium-precipitated DNA, electroporation, fusion, transfection, infection with viral vectors, biolistics, and the like.

zB7H6 polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals (e.g., COS 7 cells, HEK 293, CHO, *Xenopus* Oocytes), may be used as the expression host cells. Accordingly, specific expression systems of interest include bacterial, yeast, insect cell and mammalian cell derived expression systems. Representative expression systems in bacteria include, e.g., those described in Chang et al., *Nature* 275:615, 1978; Goeddel et al., *Nature* (1979) 281:544, 1979; Goeddel et al., *Nucleic Acids Res.* 8:4057, 1980; EP 0 036,776; U.S. Pat. No. 4,551,433; DeBoer et al., *Proc. Natl. Acad. Sci. USA* 80:21-25, 1983; and Siebenlist et al., *Cell* 20:269, 1980. Representative expression systems in yeast include, e.g., those described in Hinnen et al., *Proc. Natl. Acad. Sci. USA* 75:1929, 1978; Ito et al., *J. Bacteriol.* 153:163, 1983; Kurtz et al., *Mol. Cell. Biol.* 6:142, 1986; Kunze et al., *J. Basic Microbiol.* 25:141, 1985; Gleeson et al., *J. Gen. Microbiol.* 132:3459, 1986; Roggenkamp et al., *Mol. Gen. Genet.* 202:302, 1986; Das et al., *J. Bacteriol.* 158:1165, 1984; De Louvencourt et al., *J. Bacteriol.* 154:737, 1983; Van den Berg et al., *Bio/Technology* 8:135, 1990; Kunze et al., *J. Basic Microbiol.* 25:141, 1985; Cregg et al., *Mol. Cell. Biol.* 5:3376, 1985; U.S. Pat. Nos. 4,837,148 and 4,929,555; Beach and Nurse, *Nature* 300:706, 1981; Davidow et al., *Curr. Genet.* 10:380, 1985; Gaillardin et al., *Curr. Genet.* 10:49, 1985; Ballance et al., *Biochem. Biophys. Res. Commun.* 112:284-289, 1983; Tilburn et al., *Gene* 26:205-221, 1983; Yelton et al., *Proc. Natl. Acad. Sci. USA* 81:1470-1474, 1984; Kelly and Hynes, *EMBO J.* 4:475479, 1985; EP 0 244,234; and WO 91/00357. Representative expression systems in insect cells include, e.g., those described in U.S. Pat. No. 4,745,051; Friesen et al., "The Regulation of Baculovirus Gene Expression", in: *The Molecular Biology Of Baculoviruses* (W. Doerfler, ed., 1986); EP 0 127,839; EP 0 155,476; and Vlak et al., *J. Gen. Virol.* 69:765-776, 1988; Miller et al., *Ann. Rev. Microbiol.* 42:177, 1988; Carbonell et al., *Gene* 73:409, 1988; Maeda et al., *Nature* 315:592-594, 1985; Lebacq-Verheyden et al., *Mol. Cell. Biol.* 8:3129, 1988; Smith et al., *Proc. Natl. Acad. Sci. USA* 82:8844, 1985; Miyajima et al., *Gene* 58:273, 1987; and Martin et al., *DNA* 7:99, 1988. Numerous baculoviral strains and variants and corresponding permissive insect host cells from hosts are described in Luckow et al., *Bio/Technology* 6:47-55, 1988; Miller et al., *Generic Engineering* 8:277-279, 1986; and Maeda et al., *Nature* 15:592-594, 1985. Representative expression systems in mammalian cells include, e.g., those described in Dijkema et al., *EMBO J.* 4:761, 1985, Gorman et al., *Proc. Natl. Acad. Sci. USA* 79:6777, 1982; Boshart et al., *Cell* 41:521, 1985; and U.S. Pat. No. 4,399,216. Other features of mammalian expression are facilitated, for example, as described in Ham and Wallace, *Meth. Enz.* 58:44, 1979; Barnes and Sato, *Anal. Biochem.* 102:255, 1980; U.S. Pat. Nos. 4,767,704, 4,657,866, 4,927,762, 4,560,655, WO 90/103430, WO 87/00195, and U.S. Pat. No. RE 30,985.

The subject nucleic acids can be used to generate genetically modified non-human animals or site specific gene modifications in cell lines. The term "transgenic" is intended to encompass genetically modified animals having the addition of DNA encoding the zB7H6 polypeptide or having an exogenous DNA encoding the zB7H6 polypeptide that is stably transmitted in the host cells. Transgenic animals may be made through homologous recombination. Alternatively, a nucleic acid construct is randomly integrated into the genome. Vectors for stable integration include plasmids, retroviruses and other animal viruses, YACs, and the like. Of interest are transgenic mammals, particularly rodents (e.g., rats, mice).

DNA constructs for homologous recombination will comprise at least a portion of the DNA encoding the soluble zB7H6 polypeptide and will include regions of homology to the target locus. Conveniently, markers for positive and negative selection are included. Methods for generating cells having targeted gene modifications through homologous recombination are known in the-art. For various techniques for transfecting mammalian cells, see, for example, Known et al. *Methods in Enzymology* 185:527-537, 1990.

For embryonic stem (ES) cells, an ES cell line may be employed, or ES cells may be obtained freshly from a host (e.g., mouse, rat, guinea pig). Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination. Those colonies that show homologous recombination may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected. The chimeric animals are screened for the presence of the DNA encoding the zB7H6 polypeptide and males and females having the modification are mated to produce homozygous progeny. The transgenic animals may be any non-human mammal, such as, e.g., laboratory animals or domestic animals. The transgenic animals may be used to determine the effect of a candidate drug in an in vivo environment.

The present invention further includes the recombinant vectors and host cells comprising the vectors as described herein. In general, recombinant vectors and host cells of the invention are isolated; however, a host cell comprising a polynucleotide of the invention may be part of a genetically modified animal.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art. zB7H6 polypeptides can be produced as monomers or multimer (e.g., homodimers, heterodimers, tetramers)

Accordingly, in yet another aspect, the present invention provides a method of preparing a soluble zB7H6 polypeptide, including monomeric and multimeric (e.g., homodimeric, heterodimeric, tetrameric) forms thereof, using recombinant host cells as described herein. Such methods generally include culturing a host cell transformed or transfected with an expression vectors encoding the soluble zB7H6 protein under conditions in which the protein in expressed, and recovering the soluble zB7H6 protein from the host cell. Techniques for recovering recombinant proteins for prokaryotic and eukaryotic host cells are generally well-known in the art.

For example, general methods for expressing and recovering foreign protein produced by a mammalian cell system are provided by, for example, Etcheverry, "Expression of Engineered Proteins in Mammalian Cell Culture," in *Protein Engineering: Principles and Practice* 163 (Cleland et al., eds., Wiley-Liss, Inc. 1996). Standard techniques for recovering protein produced by a bacterial system are provided by, for example, Grisshammer et al., "Purification of over-produced proteins from *E. coli* cells," in *DNA Cloning* 2: *Expression Systems, 2nd Edition* 59-92 (Glover et al., eds., Oxford University Press 1995). Established methods for isolating recombinant proteins from a baculovirus system are described by, e.g., Richardson (ed.), *Baculovirus Expression Protocols* (The Humana Press, Inc. 1995).

When expressing a soluble zB7H6 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Alternatively, zB7H6 polypeptides of the present invention can be synthesized by exclusive solid phase synthesis, partial solid phase methods, fragment condensation or classical solution synthesis. These synthesis methods are well-known to those of skill in the art. (See, e.g., Merrifield, *J. Am. Chem. Soc.* 85:2149, 1963; Stewart et al., "Solid Phase Peptide Synthesis" (2nd ed., Pierce Chemical Co. 1984); Bayer and Rapp, *Chem. Pept. Prot.* 3:3, 1986; Atherton et al., *Solid Phase Peptide Synthesis: A Practical Approach* (IRL Press 1989); Fields and Colowick, "Solid-Phase Peptide Synthesis," *Methods in Enzymology* Volume 289 (Academic Press 1997); and Lloyd-Williams et al., *Chemical Approaches to the Synthesis of Peptides and Proteins* (CRC Press, Inc. 1997).) Variations in total chemical synthesis strategies, such as "native chemical ligation" and "expressed protein ligation" are also standard. (See, e.g., Dawson et al., *Science* 266:776, 1994; Hackeng et al., *Proc. Nat'l Acad. Sci. USA* 94:7845, 1997; Dawson, *Methods Enzymol.* 287:34, 1997; Muir et al, *Proc. Nat'l Acad. Sci. USA* 95:6705, 1998; and Severinov and Muir, *J. Biol. Chem.* 273:16205, 1998.)

As previously discussed, soluble zB7H6 polypeptides can be produced either as monomers or in any of various multimeric forms (e.g., homodimers, heterodimers, or tetramers). In the case of recombinantly produced heteromultimers, comprising at least one polypeptide chain that is a soluble zB7H6 polypeptide as described herein and at least one other polypeptide chain that is a soluble non-zB7H6 polypeptide, host cells are transformed or transfected with different expression vectors encoding the different polypeptide chains. In some embodiments, the same host cell is transfected or transformed with different expression vectors encoding the different chains of a heteromultimer and heteromultimeric protein is then isolated from the medium; alternatively, each vector encoding a different polypeptide chain can be separately produced in different host cell populations and subsequently used to form multimeric complexes following isolation of recombinant protein. For example, different polypeptide chain components can be combined in deliberate ratios to result in the heteromultimeric molecules desired.

Different polypeptide chains of a heteromultimer can be differentially labeled with various tag sequences (e.g., His tag, FLAG tag, and Glu-Glu tag) to allow analysis of the composition or purification of the resulting molecules. In particular embodiments, the heteromultimer is a heterodimer (such as, e.g., a dimer in which one polypeptide chain is a soluble zB7H6 fusion protein comprising, for example, an immunoglobulin heavy chain region) or a heterotetramer (such as, e.g., a tetramer in which at least one polypeptide chain is a soluble zB7H6 fusion protein comprising, e.g., a VASP domain).

The polypeptides of the present invention are typically purified to at least about 80% purity, more typically to at least about 90% purity and preferably to at least about 95%, at least about 96%, at least about 97%, at least about 98%, or at least about 99% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, purified polypeptide is substantially free of other polypeptides, particularly other polypeptides of animal origin.

Fractionation and/or conventional purification methods can be used to obtain zB7H6 polypeptide preparations purified from natural sources (e.g., human tissue sources), synthetic zB7H6 polypeptides, and recombinant zB7H6 polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are suitable. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, e.g., *Affinity Chromatography: Principles &Methods* (Pharmacia LKB Biotechnology 1988); and Doonan, *Protein Purification Protocols* (The Humana Press 1996).

Additional variations in zB7H6 polypeptide isolation and purification can be devised by those of skill in the art. For example, anti-zB7H6 antibodies, obtained as described below, can be used to isolate large quantities of protein by immunoaffinity purification.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (see, e.g., M. Deutscher, (ed.), *Meth. Enzymol.* 182:529, 1990). Within additional embodiments of the invention, a fusion of the polypeptide of interest and an affinity tag (e.g., maltose-binding protein, an immunoglobulin domain) may be constructed to facilitate purification. Moreover, the counter-receptor-binding properties of zB7H6 extracellular domain can be exploited for purification of zB7H6 polypeptides; for example, by using affinity chromatography wherein NKp30 is bound to a column and the zB7H6 polypeptide is bound and subsequently eluted using standard chromatography methods.

zB7H6 polypeptides or fragments thereof may also be prepared through chemical synthesis, as described above. zB7H6 polypeptides may be monomers or multimers; glycosylated or non-glycosylated; PEGylated or non-PEGylated; and may or may not include an initial methionine amino acid residue.

Once produced, function of a zB7H6 polypeptide can be readily assessed using routine assays. Binding of a zB7H6 polypeptide to NKp30 is one measure of functional activity. Such binding activity may be determined, for example, by competition for binding to the binding domain of NKp30 (i.e., competitive binding assays). For example, one configuration of a competitive binding assay uses a labeled, soluble NKp30 receptor (e.g., a fusion protein comprising the extracellular domain of NKp30 and an Fc fragment conjugated to biotin) and intact cells expressing a native form of zB7H6 (e.g., a polypeptide having the amino acid sequence of SEQ ID NO:2). Such an assay is described in Example 7. Also, binding of soluble zB7H6 polypeptides to NKp30-expressing cells may be measured. Alternatively, instead of using soluble zB7H6 or intact cells expressing a native form of zB7H6, one could substitute purified zB7H6 bound to a solid phase. Competitive binding assays can be performed using standard methodology. Qualitative or semi-quantitative results can be obtained by competitive autoradiographic plate binding assays, or fluorescence activated cell sorting, or Scatchard plots may be utilized to generate quantitative results.

Function of a zB7H6 polypeptide may also be measured using bioassays that measure, e.g., biological activity associated with NKp30 function, including, for example, NK cell cytolytic assays. For example, as shown herein, certain cell lines, such as P815, do not serve as good cytolytic targets for NK-92 cells, which express NKp30. (See, e.g., Example 7.) Expression of hzB7H6 (SEQ ID NO:2) in these cells, however, such as by transfection with a zB7H6 expression vector, renders the cells vulnerable to attack by NK-92 cells. (See id.) Accordingly, zB7H6 polypeptides, zB7H6 polypeptides having one or more amino acid substitutions, addition, or deletions in the extracellular domain, can be readily screened for functional activity by expressing such polypeptides in P815 cells and determining, using NK-92 cells in well-known cytolytic assays, whether such cells are vulnerable to NK cell attack. An exemplary NK-92 cell assay that can be used to evaluate zB7H6 polypeptide function is described in Example 7, infra.

Other assays for evaluating function of zB7H6 polypeptides include, for example, addition of a soluble zB7H6 polypeptide to NKp30-expressing NK cells to test for activation of NK cell function against target cells (e.g., P815). NK cell assays for evaluation of antibodies against NK cell-surface receptors have been described, e.g., by Pende et. al. (*J. Exp. Med.* 190:1505-1516, 1999), and such assays are readily amenable to adaptation for evaluating activity of soluble zB7H6 polypeptides as described herein.

IV. Antibodies to zB7H6 Proteins

In another aspect, the present invention provides antibodies that specifically bind to zB7H6. In preferred embodiments, an anti-zB7H6 antibody of the invention is an isolated antibody that specifically binds to an extracellular domain of zB7H6 (e.g., to a polypeptide segment having the amino acid sequence set forth in residues 25-266 of SEQ ID NO:2). In some embodiments, an anti-zB7H6 antibody of the invention is capable of inhibiting the interaction of zB7H6 with human NKp30; such antibodies are useful, for example, for inhibiting cellular or other physiological events associated with the interaction of zB7H6 with NKp30, including, for example, zB7H6- and/or NKp30-mediated intracellular signaling and associated effector function (e.g., NKp30-mediated cytolytic activity).

Antibodies to zB7H6 can be obtained, for example, using the product of a zB7H6 expression vector or zB7H6 isolated from a natural source as an antigen. Particularly useful anti-zB7H6 antibodies "bind specifically" to zB7H6. Antibodies are considered to be specifically binding if the antibodies exhibit at least one of the following two properties: (1) antibodies bind to zB7H6 with a threshold level of binding activity, and (2) antibodies do not significantly cross-react with polypeptides related to zB7H6.

With regard to the first characteristic, antibodies specifically bind if they bind to a zB7H6 polypeptide, peptide, or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51:660, 1949). With regard to the second characteristic, antibodies do not significantly cross-react with related polypeptide molecules, for example, if they detect zB7H6, but not presently known polypeptides using a standard Western blot analysis. Examples of known related polypeptides include known B7 family members.

Anti-zB7H6 antibodies can be produced using antigenic zB7H6 epitope-bearing peptides and polypeptides. Antigenic epitope-bearing peptides and polypeptides typically contain a sequence of at least nine, or between 15 to about 30 amino acids contained within the amino acid sequence of SEQ ID NO:2. However, peptides or polypeptides comprising a larger portion of an amino acid sequence of the invention, containing from 30 to 50 amino acids, or any length up to and including the entire amino acid sequence of a zB7H6 polypeptide, also are useful for inducing antibodies that bind with zB7H6. It is desirable that the amino acid sequence of the epitope-bearing peptide is selected to provide substantial solubility in aqueous solvents (i.e., the sequence includes relatively hydrophilic residues, while hydrophobic residues are typically avoided). In addition, amino acid sequences containing proline residues may be also be desirable for antibody production.

Potential antigenic sites in zB7H6 can be identified using the Jameson-Wolf method, Jameson and Wolf (*CABIOS* 4:181, 1988), as implemented by the PROTEAN program (version 3.14) of LASERGENE (DNASTAR; Madison, Wis.). Default parameters may be used in this analysis.

The Jameson-Wolf method predicts potential antigenic determinants by combining six major subroutines for protein structural prediction. For example, the Hopp-Woods method (see Hopp et al., *Proc. Nat'l Acad. Sci. USA* 78:3824, 1981) may first be used to identify amino acid sequences representing areas of greatest local hydrophilicity (parameter: seven residues averaged). In the second step, Emini's method (see Emini et al., *J. Virology* 55:836, 1985) may be used to calculate surface probabilities (parameter: surface decision threshold (0.6)=1). Third, the Karplus-Schultz method, Karplus and Schultz (*Naturwissenschaften* 72:212, 1985) may be used to predict backbone chain flexibility (parameter: flexibility threshold (0.2)=1). In fourth and fifth steps of analysis, secondary structure predictions may be applied to the data using the methods of Chou-Fasman (see Chou, "Prediction of Protein Structural Classes from Amino Acid Composition," in *Prediction of Protein Structure and the Principles of Protein Conformation* 549-586 (Fasman, ed., Plenum Press 1990) and Garnier-Robson (see Garnier et al., *J. Mol. Biol.* 120:97, 1978) (Chou-Fasman parameters: conformation table=64 proteins; α region threshold=103; β region threshold=105; Garnier-Robson parameters: α and β decision constants=0). In a sixth subroutine, flexibility parameters and hydropathy/solvent accessibility factors may be combined to determine a surface contour value, designated as the "antigenic index." Finally, a peak broadening function may be applied to the antigenic index, which broadens major surface peaks by adding, e.g., 20, 40, 60, or 80% of the respective peak value to account for additional free energy derived from the mobility of surface regions relative to interior regions. This calculation, however, is typically not applied to any major peak that resides in a helical region, since helical regions tend to be less flexible.

Polyclonal antibodies to recombinant zB7H6 protein or to zB7H6 isolated from natural sources can be prepared using methods well-known to those of skill in the art. (See, e.g., Green et al., "Production of Polyclonal Antisera," in *Immunochemical Protocols* 1-5 (Manson, ed., Humana Press 1992); Williams et al., "Expression of foreign proteins in *E. coli* using plasmid vectors and purification of specific polyclonal antibodies," in *DNA Cloning 2: Expression Systems, 2nd Edition* 15 (Glover et al., eds., Oxford University Press 1995). The immunogenicity of a zB7H6 polypeptide can be increased through the use of an adjuvant, such as alum (aluminum hydroxide) or Freund's complete or incomplete adjuvant. Polypeptides useful for immunization also include fusion polypeptides, such as fusions of zB7H6 or a portion thereof with an immunoglobulin polypeptide or with maltose binding protein. The polypeptide immunogen may be a full-length molecule or a portion thereof. If the polypeptide portion is "hapten-like," for immunization, such portion may be advantageously joined or linked to a macromolecular carrier such as, for example, keyhole limpet hemocyanin (KLH), bovine serum albumin (BSA), or tetanus toxoid.

Although polyclonal antibodies are typically raised in animals such as horses, cows, dogs, chicken, rats, mice, rabbits, guinea pigs, goats, or sheep, an anti-zB7H6 antibody of the present invention may also be derived from a subhuman primate antibody. General techniques for raising diagnostically and therapeutically useful antibodies in baboons may be found, for example, in Goldenberg et al., International Patent Publication No. WO 91/11465, and in Losman et al., *Int. J. Cancer* 46:310, 1990.

Alternatively, monoclonal anti-zB7H6 antibodies can be generated. For example, rodent monoclonal antibodies to specific antigens may be obtained by methods known to those skilled in the art (see, e.g., Kohler et al., *Nature* 256:495, 1975; Coligan et al. (eds.), *Current Protocols in Immunology*, Vol. 1 2.5.1-2.6.7 (John Wiley & Sons 1991) ["Coligan"]; Picksley et al., "Production of monoclonal antibodies against proteins expressed in *E. coli*," in *DNA Cloning 2: Expression Systems, 2nd Edition* 93 (Glover et al., eds., Oxford University Press 1995). In certain variations, monoclonal antibodies are obtained by injecting mice with a composition comprising a zB7H6 gene product (e.g., a polypeptide comprising or consisting of SEQ ID NO:2 residues 25-266), verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

An anti-zB7H6 antibody may also be a human monoclonal antibody, or an antibody derived therefrom. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13, 1994; Lonberg et al., *Nature* 368:856, 1994; and Taylor et al., *Int. Immun.* 6:579, 1994.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, e.g., Coligan at pages 2.7.1-2.7.12 and pages 2.9.1-2.9.3; Baines et al., "Purification of Immunoglobulin G (IgG)," in *Methods in Molecular Biology* (Vol. 10) 79-104 (The Humana Press, Inc. 1992)).

In some embodiments, an anti-B7H6 antibody is an antibody fragment comprising an antigen-binding domain of an intact (whole) antibody. Such antibody fragments can be obtained, for example, by proteolytic hydrolysis of an antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent $F_{ab}$ fragments and an $F_c$ fragment directly. These methods are described, for example, in U.S. Pat. No. 4,331,647 to Goldenberg; Nisonoff et al., *Arch Biochem. Biophys.* 89:230, 1960; Porter, *Biochem. J.* 73:119, 1959; Edelman et al., in *Methods in Enzymology* (Vol. 1) 422 (Academic Press 1967); and Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659, 1972. Alternatively, the variable chains can be linked by an intermolecular disulfide bond or cross-linked by chemicals such as glutaraldehyde (see, e.g., Sandhu, *Crit. Rev. Biotech.* 12:437, 1992).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97, 1991. (See also Bird et al., *Science* 242:423, 1988; U.S. Pat. No. 4,946,778 to Ladner et al.; Pack et al., *Bio/Technology* 11:1271, 1993, and Sandhu, supra.) As an illustration, a scFV can be obtained by exposing lymphocytes to zB7H6 polypeptide in vitro, and selecting antibody display libraries in phage or similar vectors (for instance, through use of immobilized or labeled zB7H6 protein or peptide).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, e.g., Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application* 166 (Ritter et al., eds., Cambridge University Press 1995); and Ward et al., "Genetic Manipulation and Expression of Antibodies," in *Monoclonal Antibodies: Principles and Applications* 137 (Birch et al., eds., Wiley-Liss, Inc. 1995)).

Alternatively, an anti-zB7H6 antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833, 1989. Techniques for producing humanized monoclonal antibodies are described, for example, by Jones et al., *Nature* 321:522, 1986; Carter et al., *Proc. Nat'l Acad. Sci. USA* 89:4285, 1992; Sandhu, *Crit. Rev. Biotech.* 12:437, 1992; Singer et al., *J. Immun.* 150:2844, 1993; Sudhir (ed.), *Antibody Engineering Protocols* (Humana Press, Inc. 1995); Kelley, "Engineering Therapeutic Antibodies," in *Protein Engineering Principles* and Practice 399-434 (Cleland et al., eds., John Wiley & Sons, Inc. 1996); and U.S. Pat. No. 5,693,762 to Queen et al.

In certain variations, an anti-zB7H6 antibody includes an Fc region, which comprises the $C_H2$ and $C_H3$ domains of an immunoglobulin (Ig) heavy chain and typically a portion of an Ig hinge region. Fc is responsible for two of the highly desirable properties of an IgG: recruitment of effector function and a long serum half-life. The ability to kill target cells to which an antibody is attached stems from the activation of immune effector pathway (ADCC) and the complement pathway (CDC) through the binding of Fc to Fc receptors and the complement protein, C1q, respectively. The binding is mediated by residues located primarily in the lower hinge region and upper $C_H2$ domain. (See, e.g., Wines et al., *J. Immunol.* 164:5313, 2000; Woof and Burton, *Nature Reviews* 4:1, 2004.) The long half-life in serum demonstrated by IgG is mediated through a pH dependent interaction between amino acids in the $C_H2$ and $C_H3$ domain and the neonatal Fc receptor, FcRn. (See, e.g., Getie and Ward, *Immunology Today* 18:592, 1997; Petkova et al., *Int. Immunol.* 18:1759, 2006.) Accordingly, in certain embodiments of an anti-zB7H6 antibody comprising an Fc region, the Fc region has ADCC and/or CDC activity. Such antibodies are particularly useful for mediating killing of target cells expressing zB7H6 such as, for example, cancer cells or virally infected cells. In other embodiments, an anti-zB7H6 antibody comprises an Fc region that lacks one or more effector functions (e.g., lacks ADCC and/or CDC activity). Fc regions lacking or having substantially reduced effector function may be obtained, for example, by introducing one or more amino acid substitutions into a native Fc region sequence, such that the Fc region does not bind, or has substantially reduced binding, to cytolytic Fc receptors and/or the C1q complement protein. Particularly suitable Fc regions lacking or having substantially reduced effector function include, for example, Fc4 (SEQ ID NO:31), Fc5 (SEQ ID NO:32), and Fc6 (SEQ ID NO:33), and Fc7 (SEQ ID NO:34), which are shown in FIGS. 13A-13C.

In certain embodiments comprising an Fc region, the Fc region is a single chain Fc (scFc), which comprises two Fc domain monomers joined by a flexible linker, such that the two Fc monomers are capable of dimerization to form a functional, dimeric Fc domain. For example, in some variations of an anti-zB7H6 antibody comprising a scFc, the antibody comprises a single chain Fv (scFv) fused to the scFc portion, wherein the scFv portion specifically binds to zB7H6. Single chain Fc polypeptides, including fusion polypeptides comprising scFc and one more antigen-binding domains (e.g., scFv), are further described in International PCT Patent Application No. US08/060,852, entitled "Single Chain Fc, Methods of Making, and Methods of Treatment," filed Apr. 18, 2008, the disclosure of which is incorporated by reference herein in its entirety.

Moreover, anti-zB7H6 antibodies or antibody fragments of the present invention can be PEGylated using methods in the art and described herein.

Anti-idiotypic antibodies may be raised against an anti-zB7H6 antibody specific for the zB7H6 extracellular domain (e.g., against SEQ ID NO:2 residues 25-266). In some variations, an anti-idiotype antibody is against an anti-zB7H6 antibody that is capable of inhibiting the interaction of zB7H6 with human NKp30; such anti-idiotype antibodies may mimic the ability of zB7H6 to bind NKp30 and, in preferred embodiments, are capable of triggering or enhancing NKp30-mediated NK cell activation. Polyclonal anti-idiotype antibodies can be prepared by immunizing animals with anti-zB7H6 antibodies or antibody fragments, using standard techniques. (See, e.g., Green et al., "Production of Polyclonal Antisera," in *Methods In Molecular Biology: Immunochemical Protocols* 1-12 (Manson, ed., Humana Press 1992). See also Coligan at pages 2.4.1-2.4.7.) Alternatively, monoclonal anti-idiotype antibodies can be prepared using anti-zB7H6 antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, in U.S. Pat. No. 5,208,146 to Irie; U.S. Pat. No. 5,637,677 to Greene, et. al., and Varthakavi and Minocha, *J. Gen. Virol.* 77:1875, 1996.

An anti-zB7H6 antibody can be conjugated with a detectable label to form an anti-zB7H6 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3H$, $^{125}I$, $^{131}I$, $^{35}S$ and $^{14}C$.

Anti-zB7H6 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-zB7H6 immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-zB7H6 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-zB7H6 immunoconjugates can be detectably labeled by linking an anti-zB7H6 antibody component to an enzyme. When the anti-zB7H6-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-zB7H6 antibodies can be accomplished using standard techniques known to the art. Typical methodology in this regard is described by Kennedy et al., *Clin. Chim. Acta* 70:1, 1976; Schurs et al.,

*Clin. Chim. Acta* 81:1, 1977; Shih et al., *Int'J. Cancer* 46:1101, 1990; Stein et al., *Cancer Res.* 50:1330, 1990; and Coligan, supra.

Moreover, the convenience and versatility of immunochemical detection can be enhanced by using anti-zB7H6 antibodies that have been conjugated with avidin, streptavidin, and biotin. (See, e.g., Wilchek et al. (eds.), "Avidin-Biotin Technology," *Methods In Enzymology* (Vol. 184) (Academic Press 1990); Bayer et al., "Immunochemical Applications of Avidin-Biotin Technology," in *Methods In Molecular Biology* (*Vol.* 10) 149-162 (Manson, ed., The Humana Press, Inc. 1992).)

Methods for performing immunoassays are well-established. (See, e.g., Cook and Self, "Monoclonal Antibodies in Diagnostic Immunoassays," in *Monoclonal Antibodies: Production, Engineering, and Clinical Application* 180-208 (Ritter and Ladyman, eds., Cambridge University Press 1995); Perry, "The Role of Monoclonal Antibodies in the Advancement of Immunoassay Technology," in *Monoclonal Antibodies: Principles and Applications* 107-120 (Birch and Lennox, eds., Wiley-Liss, Inc. 1995); Diamandis, *Immunoassay* (Academic Press, Inc. 1996).)

The present invention also contemplates kits for performing an immunological diagnostic assay for zB7H6 gene expression. Such kits comprise at least one container comprising an anti-zB7H6 antibody. A kit may also comprise a second container comprising one or more reagents capable of indicating the presence of zB7H6 antibody. Examples of such indicator reagents include detectable labels such as a radioactive label, a fluorescent label, a chemiluminescent label, an enzyme label, a bioluminescent label, colloidal gold, and the like. A kit may also comprise a means for conveying to the user that zB7H6 antibodies are used to detect zB7H6 protein. For example, written instructions may state that the enclosed antibody or antibody fragment can be used to detect zB7H6. The written material can be applied directly to a container, or the written material can be provided in the form of a packaging insert.

V. Anti-zB7H6 Antibody-Drug Conjugates

In certain aspects, the present invention provides an anti-zB7H6 antibody-drug conjugate. An "anti-zB7H6 antibody-drug conjugate" as used herein refers to an anti-zB7H6 antibody (as described in Section IV, supra) conjugated to a therapeutic agent. Such anti-zB7H6 antibody-drug conjugates produce clinically beneficial effects on zB7H6-expressing cells when administered to a subject, such as, for example, a subject with a zB7H6-expressing cancer, typically when administered alone but also in combination with other therapeutic agents.

In typical embodiments, an anti-zB7H6 antibody is conjugated to a cytotoxic agent, such that the resulting antibody-drug conjugate exerts a cytotoxic or cytostatic effect on a zB7H6-expressing cell (e.g., a zB7H6-expressing cancer cell) when taken up or internalized by the cell. Particularly suitable moieties for conjugation to antibodies are chemotherapeutic agents, prodrug converting enzymes, radioactive isotopes or compounds, or toxins. For example, an anti-zB7H6 antibody can be conjugated to a cytotoxic agent such as a chemotherapeutic agent (see infra) or a toxin (e.g., a cytostatic or cytocidal agent such as, for example, abrin, ricin A, pseudomonas exotoxin, or diphtheria toxin). Examples of additional agents that are useful for conjugating to an anti-zB7H6 antibody are provided infra.

In other embodiments, an anti-zB7H6 antibody is conjugated to a pro-drug converting enzyme. The pro-drug converting enzyme can be recombinantly fused to the antibody or chemically conjugated thereto using known methods. Exemplary pro-drug converting enzymes are carboxypeptidase G2, β-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Amon et al., "Monoclonal Antibodies For Immunotargeting Of Drugs In Cancer Therapy," in *Monoclonal Antibodies And Cancer Therapy* (Reisfeld et al. eds., Alan R. Liss, Inc., 1985); Hellstrom et al., "Antibodies For Drug Delivery," in *Controlled Drug Delivery* (Robinson et al. eds., Marcel Deiker, Inc., 2nd ed. 1987); Thorpe, "Antibody Carriers Of Cytotoxic Agents In Cancer Therapy: A Review," in *Monoclonal Antibodies '84: Biological And Clinical Applications* (Pinchera et al. eds., 1985); "Analysis, Results, and Future Prospective of the Therapeutic Use of Radiolabeled Antibody In Cancer Therapy," in *Monoclonal Antibodies For Cancer Detection And Therapy* (Baldwin et al. eds., Academic Press, 1985); and Thorpe et al., 1982, *Immunol. Rev.* 62:119-58. See also, e.g., PCT publication WO 89/12624.)

In certain variations, in accordance with methods described herein, an anti-zB7H6 antibody-drug conjugate is internalized and accumulates within a zB7H6-expressing cell, where antibody-drug conjugate exerts a therapeutic effect (e.g., a cytotoxic or cytostatic effect). Methods for determining accumulation and rates of accumulation are found in, for example, WO 2004/010957, entitled "Drug Conjugates and Their Use for Treating Cancer, an Autoimmune Disease or an Infectious Disease."

In typical embodiments, when using an anti-zB7H6 antibody conjugated to a therapeutic agent (e.g., a drug or a prodrug converting enzyme), the agent is preferentially active when internalized by zB7H6-expressing cells (e.g., cells of a zB7H6-expressing cancer) to be treated. In other embodiments, the anti-zB7H6 antibody-drug conjugate is not internalized, and the drug is effective to exert a therapeutic effect (e.g., depletion or inhibition of growth of zB7H6-expressing cells) by binding to the cell membrane.

To minimize activity of a therapeutic agent outside a zB7H6-expressing cell (e.g., a zB7H6-expressing cancer cell), a therapeutic agent is typically conjugated in a manner that reduces its activity unless it is cleaved off the antibody (e.g., by hydrolysis or by a cleaving agent). In such embodiments, the therapeutic agent is attached to the antibody with a cleavable linker that is sensitive to cleavage in the intracellular environment of the zB7H6-expressing cell but is not substantially sensitive to the extracellular environment, such that the conjugate is cleaved from the antibody when it is internalized by the zB7H6-expressing cell (e.g., in the endosomal or, for example, by virtue of pH sensitivity or protease sensitivity, in the lysosomal environment or in a caveolea). (See Section V(A), infra.)

Further, in certain embodiments, an antibody-drug conjugate comprises a therapeutic agent that is charged relative to the plasma membrane, thereby further minimizing the ability of the agent to cross the plasma membrane once internalized by a cell. As used herein, a "charged agent" means an agent that (a) is polarized, such that one region of the agent has a charge relative to the plasma membrane, or (b) has a net charge relative to the plasma membrane.

Typically, an anti-zB7H6 antibody-drug conjugate is substantially purified (e.g., substantially free from substances that limit its effect or produce undesired side-effects). In certain specific embodiments, the anti-zB7H6 antibody-drug conjugate is 40% pure, more typically about 50% pure, and most typically about 60% pure. In other specific embodiments, the anti-CD70 ADC or ADC derivative is at least approximately 60-65%, 65-70%, 70-75%, 75-80%, 80-85%, 85-90%, 90-95%, or 95-98% pure. In another specific embodiment, the anti-CD70 ADC or ADC derivative is approximately 99% pure.

A. Linkers

Typically, a zB7H6 antibody-drug conjugate comprises a linker region between the therapeutic agent and the anti-zB7H6 antibody. As noted supra, in certain embodiments, the linker is cleavable under intracellular conditions, such that cleavage of the linker releases the therapeutic agent from the antibody in the intracellular environment.

For example, in some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, *Pharm. Therapeutics* 83:67-123, 1999). Most typical are peptidyl linkers that are cleavable by enzymes that are present in zB7H6-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker). Other such linkers are described, e.g., in U.S. Pat. No. 6,214,345. In specific embodiments, the peptidyl linker cleavable by an intracellular protease is a Val-Cit (valine-citrulline) linker or a Phe-Lys (phenylalanine-lysine) linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, a pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, *Pharm. Therapeutics* 83:67-123, 1999; Neville et al., *Biol. Chem.* 264:14653-14661, 1989.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929)).

In yet other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT. (See, e.g., Thorpe et al., *Cancer Res.* 47:5924-5931, 1987; Wawrzynczak et al., *Immunoconjugates: Antibody Conjugates in Radioimagery and Therapy of Cancer* (C. W. Vogel ed., Oxford U. Press, 1987. See also U.S. Pat. No. 4,880,935.)

In yet other variations, the linker is a malonate linker (Johnson et al., *Anticancer Res.* 15:1387-93, 1995), a maleimidobenzoyl linker (Lau et al., *Bioorg-Med-Chem.* 3:1299-1304, 1995), or a 3'-N-amide analog (Lau et al., *Bioorg-Med-Chem.* 3:1305-12, 1995).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of an antibody-drug conjugate, are cleaved when the antibody-drug conjugate is present in an extracellular environment (e.g., in plasma). Whether a linker is not substantially sensitive to the extracellular environment can be determined, for example, by incubating independently with plasma both (a) the antibody-drug conjugate (the "antibody-drug conjugate sample") and (b) an equal molar amount of unconjugated antibody or therapeutic agent (the "control sample") for a predetermined time period (e.g., 2, 4, 8, 16, or 24 hours) and then comparing the amount of unconjugated antibody or therapeutic agent present in the antibody-drug conjugate sample with that present in the control sample, as measured, for example, by high performance liquid chromatography.

In some variations, the linker promotes cellular internalization. In certain embodiments, the linker promotes cellular internalization when conjugated to the therapeutic agent (i.e., in the milieu of the linker-therapeutic agent moiety of the antibody-drug conjuage). In yet other embodiments, the linker promotes cellular internalization when conjugated to both the therapeutic agent and the anti-zB7H6 antibody (i.e., in the milieu of the antibody-drug conjugate).

A variety of linkers that can be used with the present compositions and methods are described in, for example, WO 2004/010957, entitled "Drug Conjugates and Their Use for Treating Cancer, an Autoimmune Disease or an Infectious Disease."

B. Therapeutic Agents

In accordance with the present invention, any agent that exerts a therapeutic effect on a zB7H6-expressing cell can be used as the therapeutic agent for conjugation to an anti-zB7H6 antibody. In certain embodiments, such as for treatment of a zB7H6-expressing cancer, the therapeutic agent is a cytotoxic agent.

Useful classes of cytotoxic agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and -carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

Particularly suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In certain embodiments, a cytotoxic agent is a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to an anti-zB7H6-expressing antibody.

In specific variations, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP (dimethylvaline-valine-dolaisoleuine-dolaproine-phenylalanine-p-phenylenediamine), MMAF (dovaline-valine-dolaisoleunine-dolaproine-phenylalanine), and MAE (monomethyl auristatin E). The synthesis and structure of auristatin E and its derivatives are described in U.S. Patent Application Publication No. 20030083263; International Patent Publication Nos. WO 2002/088172 and WO 2004/010957; and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In other variations, the cytotoxic agent is a DNA minor groove binding agent. (See, e.g., U.S. Pat. No. 6,130,237.) For example, in certain embodiments, the minor groove binding agent is a CBI compound. In other embodiments, the minor groove binding agent is an enediyne (e.g., calicheamicin).

In certain embodiments, an antibody-drug conjugate comprises an anti-tubulin agent. Examples of anti-tubulin agents include, for example, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin. In some embodiments, the cytotoxic agent is a maytansinoid, another group of anti-tubulin agents. For example, in specific embodiments, the maytansinoid is maytansine or DM-1 (ImmunoGen, Inc.; see also Chari et al., *Cancer Res.* 52:127-131, 1992).

In other embodiments, the cytotoxic agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

C. Formation of Anti-zB7H6 Antibody-Drug Conjugates

The generation of anti-zB7H6 antibody-drug conjugates can be accomplished by any technique known to the skilled artisan. Briefly, an anti-zB7H6 antibody-drug conjugate comprises an anti-zB7H6 antibody, a drug, and optionally a linker that joins the drug and the antibody. A number of different reactions are available for covalent attachment of drugs to antibodies. This is often accomplished by reaction of the amino acid residues of the antibody molecule, including the amine groups of lysine, the free carboxylic acid groups of glutamic and aspartic acid, the sulfhydryl groups of cysteine, and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of the antibody molecule. Also available for attachment of drugs to antibodies is the Schiff base reaction. This method involves the periodate oxidation of a drug that contains glycol or hydroxy groups, thus forming an aldehyde which is then reacted with the antibody molecule. Attachment occurs via formation of a Schiff base with amino groups of the antibody molecule. Isothiocyanates can also be used as coupling agents for covalently attaching drugs to antibodies. Other techniques are known to the skilled artisan and within the scope of the present invention. Non-limiting examples of such techniques are described in, e.g., U.S. Pat. Nos. 5,665,358; 5,643,573; and 5,556,623.

In some embodiments, an intermediate, which is the precursor of the linker, is reacted with the drug under appropriate conditions. In certain embodiments, reactive groups are used on the drug and/or the intermediate. The product of the reaction between the drug and the intermediate, or the derivatized drug, is subsequently reacted with the anti-zB7H6 antibody under appropriate conditions.

D. Assays for Cytotoxic or Cytostatic Activities

In certain embodiments, an anti-zB7H6 antibody-drug conjugate comprises an anti-zB7H6 antibody conjugated to a cytotoxic agent, such that the antibody-drug conjugate exerts a cytotoxic or cytostatic effect on a zB7H6-expressing cell (e.g., a zB7H6-expressing cancer cell). zB7H6-expressing cells that can be assayed for a cytotoxic or cytostatic effect of an anti-zB7H6 antibody-drug conjugate can be culture cell lines such as, for example, those listed in Table 5, infra. Once an anti-zB7H6 antibody-drug conjugate is confirmed as exerting a cytotoxic or cytostatic on zB7H6-expressing cells, its therapeutic value can be validated in an appropriate animal model. In preferred embodiments, an anti-zB7H6 antibody-drug conjugate comprising a cytotoxic agent is used to treat a zB7H6-expressing cancer. Exemplary animal models of various cancers, which may be used to evaluate therapeutic efficacy of an antibody-drug conjugate of the present invention, are described in Section VI(B) and in Examples 21-27, infra.

Methods of determining whether an agent exerts a cytostatic or cytotoxic effect on a cell are generally known in the art. Illustrative examples of such methods are described below. Determination of any of these effects on zB7H6-expressing cells indicates that an anti-zB7H6 antibody-drug conjugate is useful in the treatment or prevention of diseases or disorders having a pathology mediated, at least in part, by aberrant growth or activation of zB7H6-expressing cells, such as, for example, a zB7H6-expressing cancer.

For determining whether an anti-zB7H6 antibody-drug conjugate exerts a cytostatic effect on zB7H6-expressing cells, a thymidine incorporation assay may be used. For example, zB7H6-expressing cells, at a density of 5,000 cells/well of a 96-well plate, can be cultured for a 72-hour period and exposed to 0.5 µCi of $^3$H-thymidine during the final 8 hours of the 72-hour period, and the incorporation of $^3$H-thymidine into cells of the culture is measured in the presence and absence of the antibody-drug conjugate.

For determining cytotoxicity, necrosis or apoptosis (programmed cell death) can be measured. Necrosis is typically accompanied by increased permeability of the plasma membrane, swelling of the cell, and rupture of the plasma membrane. Apoptosis is typically characterized by membrane blebbing, condensation of cytoplasm, and the activation of endogenous endonucleases.

Cell viability can be measured by determining in a cell the uptake of a dye such as neutral red, trypan blue, or ALAMAR™ blue (see, e.g., Page et al., *Intl. J. of Oncology* 3:473-476, 1993). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytotoxicity (Skehan et al., *J. Nat'l Cancer Inst.* 82:1107-12, 1990).

Alternatively, a tetrazolium salt, such as MTT, is used in a quantitative calorimetric assay for mammalian cell survival and proliferation by detecting living, but not dead, cells (see, e.g., Mosmann, *J. Immunol. Methods* 65:55-63, 1983).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has previously been described by Duke and Cohen, *Current Protocols In Immunology* (Coligan et al. eds., 1992, pp. 3.17.1-3.17.16). Cells can be also labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsining the attached cells, combining the preparations following a centrifugation wash step (e.g., 10 minutes, 2000 rpm), and detecting apoptosis (e.g., by measuring DNA fragmentation). (See, e.g., Piazza et al., Cancer Research 55:3110-16, 1995). ps VI. Methods of Use A. General In another aspect, the present invention provides methods of modulating activity (e.g., cytolytic activity) of an NKp30-expressing cell, including, for example, natural killer (NK) cells and T cells (e.g., CD8$^+$ T cells). Such methods include, e.g., methods for treatment of diseases or disorders associated with either increased or decreased activity of an NKp30-expressing cell. In some embodiments, the methods include contacting an NKp30-expressing cell with a zB7H6 polypeptide, or an agent capable of mimicking the interaction of zB7H6 with NKp30 (e.g., a zB7H6 anti-idiotypic antibody), in an amount effective to trigger NKp30-mediated activity (e.g., cytolytic activity). The zB7H6 polypeptides can be in either soluble or immobilized (e.g., cell-membrane-bound) form; for example, in specific variations, a method of enhancing activity of an NKp30-expressing cell includes contacting an NKp30-expressing cell with an isolated, soluble polypeptide comprising a polypeptide segment that has at least 90% or at least 95% sequence identity with the amino acid sequence set forth in residues 25-266 of SEQ ID NO:2, or contacting an NKp30-expressing cell with a cell expressing a recombinant, membrane-bound zB7H6 polypeptide. In other variations, the methods include contacting a cell expressing functional zB7H6, in the presence of an NKp30-expressing cell, with an effective amount of an anti-zB7H6 antibody or other agent capable of interfering with the interaction of zB7H6 with NKp30. Such methods can be performed in vitro, ex vivo, or in vivo.

In certain preferred variations, methods of modulating NK cell activity are provided, including, for example, methods for treatment of diseases or disorders associated with either increased or decreased NK cell activity. In some embodiments, the methods include contacting an NK cell with a zB7H6 polypeptide, or an agent capable of mimicking the interaction of zB7H6 with NKp30 (e.g., a zB7H6 anti-idiotypic antibody), in an amount effective to trigger NKp30-mediated NK cell cytolytic activity. The zB7H6 polypeptides can be in either soluble or immobilized (e.g., cell-membrane-bound) form; for example, in specific variations, a method of enhancing NK cell activity includes contacting a human NK cell with an isolated, soluble polypeptide comprising a polypeptide segment that has at least 90% or at least 95% sequence identity with the amino acid sequence set forth in residues 25-266 of SEQ ID NO:2, or contacting a human NK cell with a cell expressing a recombinant, membrane-bound zB7H6 polypeptide. In other variations, the methods include contacting a cell expressing functional zB7H6, in the presence of an NK cell, with an effective amount of an anti-zB7H6 antibody or other agent capable of interfering with the interaction of zB7H6 with NKp30. Such methods can be performed in vitro, ex vivo, or in vivo.

In other embodiments, methods of modulating NKp30-expressing T cell activity are provided, including, for example, methods for treatment of diseases or disorders associated with either increased or decreased activity of NKp30-expressing T cells. Certain T cells, including CD8$^+$ T cells, have been shown to express NKp30. (See, e.g., Srivastava and Srivastava, *Leuk. Res.* 30:37-46, 2006.) Accordingly, in some embodiments, the methods include contacting an NKp30-expressing T cell (e.g., a CD8$^+$ T cell) with a zB7H6 polypeptide, or an agent capable of mimicking the interaction of zB7H6 with NKp30 (e.g., a zB7H6 anti-idiotypic antibody), in an amount effective to trigger NKp30-mediated T cell activity (e.g., cytolytic activity). The zB7H6 polypeptides can be in either soluble or immobilized (e.g., cell-membrane-bound) form; for example, in specific variations, a method of enhancing activity of an NKp30-expressing T cell includes contacting an NKp30-expressing T cell with an isolated, soluble polypeptide comprising a polypeptide segment that has at least 90% or at least 95% sequence identity with the amino acid sequence set forth in residues 25-266 of SEQ ID NO:2, or contacting an NKp30-expressing T cell with a cell expressing a recombinant, membrane-bound zB7H6 polypeptide. In other variations, the methods include contacting a cell expressing functional zB7H6, in the presence of an NKp30-expressing T cell, with an effective amount of an anti-zB7H6 antibody or other agent capable of interfering with the interaction of zB7H6 with NKp30. Such methods can be performed in vitro, ex vivo, or in vivo.

As noted above, in particular variations, the method is a method of treating a disease or disorder associated with NK cell activity. For example, in some embodiments, the method includes administering an effective amount of a soluble zB7H6 polypeptide, or an agent capable of mimicking the interaction of zB7H6 with NKp30 (e.g., a zB7H6 anti-idiotypic antibody), to a subject suffering from, or at an elevated risk of developing, a disease or disorder characterized by insufficient natural killer (NK) cell activity (e.g., a cancer or an infectious disease). In alternative embodiments, the method includes administering an effective amount of an anti-zB7H6 antibody or other agent capable of interfering with the interaction of zB7H6 with NKp30 to a subject suffering from, or at an elevated risk of developing, an NK-cell-mediated disease or disorder (for example, NK-cell-mediated allograft rejection such as, e.g., NK-cell-mediated bone marrow cell (BMC) allograft rejection).

In some variations, a soluble zB7H6 polypeptide is used as an immunostimulatory agent for cancer therapy. A variety of secreted, immunomodulatory proteins are known to stimulate anti-tumor responses in animal models via stimulation of the immune system (see generally Rosenberg (ed.), *Principles and practice of the biologic therapy of cancer* (Lippincott Williams & Wilkins, Philadelphia, Pa., 3rd ed. 2000)). For example, the use of IL-2 and IFN-α are used for the treatments of metastatic melanoma and renal cell carcinoma. (See, e.g., Atkins et al., *J. Clin. Oncol.* 17:2105-16, 1999; Fyfe et al., *J. Clin. Oncol.* 13:688-96, 1995; Jonasch and Haluska, Oncologist 6:34-55, 2001.) The proposed mechanism of action of these cytokines includes enhancement of direct tumor cell killing by $CD8^+$ T cells and NK cells. Soluble zB7H6 receptors as described herein may be used in a similar manner to enhance direct tumor killing by NK cells or $CD8^+$ T cells via induction of NKp30-mediated cytolytic activity.

A soluble zB7H6 polypeptide can also be used as an immunostimulatory agent for the treatment of infectious disease, including, e.g., viral infections. NK cells constitute the first line of defense against invading pathogens, and usually become activated in an early phase of viral infection. (See, e.g., Ahmad and Alvarez, *J. Leukoc. Biol.* 76:743-759, 2004; Shresta et al., *Virology* 319:262-273, 2004.) $CD8^+$ T cells have also been shown to play a role in mediating immune responses to infectious pathogens. (See, e.g., Wong and Palmer, *Annu. Rev. Immunol.* 21:29-70, 2003.) Current treatments for infectious disease include immune system stimulants known to promote, inter alia, NK and T cell activity. Such treatments include, for example, the use of IL-2 as a therapeutic in HIV infection (see, e.g., Smith, *AIDS* 15 Suppl 2:S28-35, 2001), as well as the use of IFN-α in the treatment of HCV infection (see, e.g., Ahmad and Alvarez, supra). The potential for treating infectious disease via immunomodulatory proteins that increase NK cell activity is further underscored by observations that effective therapy in HCV-infected individuals correlated to their increase in NK cell activity: in the individuals in whom the therapy failed to increase an NK cell response, no decrease in viremia was observed. (See van Thiel et al., *Dig. Dis. Sci.* 39:970-976, 1994; Wozniakowska-Gesicka et al., *Pol. Merkuriusz Lek.* 8:376-377, 2000; Bonavita et al., *Int. J. Tissue React.* 15:11-16, 1993.) Thus, a soluble zB7H6 polypeptide capable of stimulating NKp30-mediated NK or $CD8^+$ T cell activity may be used to promote NK-mediated or $CD8^+$-T-cell-mediated anti-pathogen (e.g., anti-viral) defense mechanisms to treat infectious disease.

In other variations, an anti-zB7H6 antibody is used to suppress NK-cell-mediated bone marrow allograft rejection. Bone marrow transplantation (BMT) has become an accepted method of therapy for the treatment of various hematologic malignancies. The efficacy of allogeneic BMT is limited, however, by certain obstacles such as, e.g., rejection of the graft. There is ample evidence that NK cells are a barrier to the engraftment of bone marrow allografts and that they alone can mediate the specificity of BMC rejection in mice. (See, e.g., Murphy et al., *J. Exp. Med.* 165:1212-1217, 1987; Murphy et al., *J. Exp. Med.* 166:1499-1509, 1987; Murphy et al., *J. Immunol.* 144:3305-3311, 1990; Murphy et al., *Eur. J. Immunol.* 20:1729-1734, 1990; Murphy et al., *Immunol. Rev.* 181:279-289, 2001.) Clinically, allograft resistance observed in patients with SCID who have received HLA-mismatched BMTs depleted of T cells, without cytoreductive conditioning, is attributed to high activity of NK cells from the donor. (See O'Reilly et al., *Vox. Sang.* 51:81-86, 1986.) Accordingly, antibodies against the extracellular domain of zB7H6 and capable of inhibiting the interaction of zB7H6 with NKp30, as described herein, may be used during BMT to inhibit NK cell cytolytic activity against allografts and thereby treat or prevent BMC allograft rejection.

In yet other embodiments, an anti-zB7H6 antibody is used to induce antibody dependent cellular cyotoxicity (ADCC) or complement dependent cytotoxicity (CDC) against zB7H6-expressing cells such as, for example, zB7H6-expressing cancer cells. Antibody therapy has been particularly successful in cancer treatment because certain tumors either display unique antigens, lineage-specific antigens, or antigens present in excess amounts relative to normal cells. Experimental evidence demonstrates that zB7H6 is, relative to normal tissues, highly expressed by many tumor-derived cell lines, including cell lines derived from cancers of the colon, liver, cervix, lung, pancreas, and prostate, as well as those derived from various cancers of the blood such as prohemocytic leukemia, B-cell lymphoma, monocytic lymphoma, erythroleukemia, Burkitt's lymphoma, or chronic myelogenous leukemia. This evidence indicates that zB7H6 is a novel tumor-specific or tumor-associated antigen, and that an anti-zB7H6 antibody may be used as an anti-tumor therapeutic. One of the mechanisms associated with the anti-tumor activity of monoclonal antibody therapy is antibody dependent cellular cytotoxicity (ADCC). In ADCC, monoclonal antibodies bind to a target cell (e.g., cancer cell) and specific effector cells expressing receptors for the monoclonal antibody (e.g., NK cells, $CD8^+$ T cells, monocytes, granulocytes) bind the monoclonal antibody/target cell complex resulting in target cell death.

Accordingly, in some embodiments, an anti-zB7H6 antibody comprising an Fc region with effector function is used to induce antibody dependent cellular cytotoxicity (ADCC) or complement dependent cytotoxicity (CDC) against a zB7H6-expressing cell. Methods for inducing ADCC generally include contacting the zB7H6-expressing cell with an effective amount an anti-zB7H6 antibody comprising an Fc region having ADCC activity, wherein the contacting step is in the presence of a cytolytic immune effector cell expressing an Fc receptor having cytolytic activity. Immune effector cells expressing cytolytic Fc receptors (e.g., FcγRIIIα or CD16) include, for example, NK cells as well certain $CD8^+$ T cells. Methods for inducing CDC generally include contacting the zB7H6-expressing cell with an effective amount an anti-zB7H6 antibody comprising an Fc region having CDC activity, wherein the contacting step is in the presence of complement. zB7H6-expressing cells that can be targeted for killing using such methods include, for example, cancer cells, such as, e.g., colon cancer cells, liver cancer cells, cervical cancer cells, lung cancer cells, pancreatic cancer cells, prostate cancer cells, prohemocytic leukemia cells, B-cell lymphoma cells, monocytic lymphoma cells, erythroleukemia cells, Burkitt's lymphoma cells, and chronic myelogenous leukemia cells, to name a few.

In related embodiments, an anti-zB7H6 antibody comprising an Fc region with effector function is used to treat a zB7H6-expressing cancer in a subject. Such methods generally include administering to a subject an effective amount of an anti-zB7H6 antibody comprising an Fc region having ADCC activity and/or CDC activity. zB7H6-expressing cancers particularly amenable to treatment using such methods include, for example, cancers of the colon, liver, cervix, lung, pancreas, or prostate, as well as cancers of the blood such as, e.g., prohemocytic leukemia, B-cell lymphoma, monocytic lymphoma, erythroleukemia, Burkitt's lymphoma, or chronic myelogenous leukemia.

In yet other embodiments, an anti-zB7H6 antibody-drug conjugate (see Section V, supra) is used to deliver a therapeutic agent to a zB7H6-expressing cell, where the agent exerts a therapeutic effect. In certain preferred variations utilizing an anti-zB7H6 antibody-drug conjugate, the therapeutic agent is a cytotoxic agent that exerts a cytotoxic or cytostatic effect on a zB7H6-expressing cell, such as a zB7H6-expressing cancer cell. As indicated above, experimental evidence demonstrates that zB7H6 is, relative to normal tissues, highly expressed by many tumor-derived cell lines, including cell lines derived from cancers of the colon, liver, cervix, lung, pancreas, and prostate, as well as those derived from various cancers of the blood such as prohemocytic leukemia, B-cell lymphoma, monocytic lymphoma, erythroleukemia, Burkitt's lymphoma, or chronic myelogenous leukemia. This evidence indicates that zB7H6 is a novel tumor-specific or tumor-associated antigen useful for targeting agents having therapeutic efficacy in cancer treatment, particularly cytotoxic agents that can deplete or inhibit the growth of tumor cells. Accordingly, in some embodiments, an anti-zB7H6 antibody-drug conjugate, comprising an anti-zB7H6 antibody conjugated to a cytotoxic agent, is used to treat a zB7H6-expressing cancer.

In each of the embodiments of the treatment methods described herein, the soluble zB7H6 polypeptide, antibody, or other zB7H6-related agent (including, e.g., a zB7H6 polynucleotide or anti-zB7H6 antibody-drug conjugate) is delivered in a manner consistent with conventional methodologies associated with management of the disease or disorder for which treatment is sought. In accordance with the disclosure herein, an effective amount of the agent is administered to a subject in need of such treatment for a time and under conditions sufficient to prevent or treat the disease or disorder.

Subjects for administration of soluble zB7H6 polypeptides, antibodies, or other zB7H6-related agents as described herein include patients at high risk for developing a particular disease or disorder associated with NK cell activity as well as patients presenting with an existing NK cell-associated disease or disorder. In certain embodiments, the subject has been diagnosed as having the disease or disorder for which treatment is sought. Further, subjects can be monitored during the course of treatment for any change in the disease or disorder (e.g., for an increase or decrease in clinical symptoms of the disease or disorder). Also, in some variations, the subject does not suffer from another disease or disorder requiring treatment that involves mimicking or blocking the interaction of zB7H6 with a cognate receptor.

In prophylactic applications, pharmaceutical compositions or medicants are administered to a patient susceptible to, or otherwise at risk of, a particular disease in an amount sufficient to eliminate or reduce the risk or delay the outset of the disease. In therapeutic applications, compositions or medicants are administered to a patient suspected of, or already suffering from such a disease in an amount sufficient to cure, or at least partially arrest, the symptoms of the disease and its complications. An amount adequate to accomplish this is referred to as a therapeutically- or pharmaceutically-effective dose or amount. In both prophylactic and therapeutic regimes, agents are usually administered in several dosages until a sufficient response (e.g., triggering of appropriate NK cell activity or inhibition of inappropriate NK cell activity) has been achieved. Typically, the response is monitored and repeated dosages are given if the desired response starts to fade.

To identify subject patients for treatment according to the methods of the invention, accepted screening methods may be employed to determine risk factors associated with specific NK cell-associated disorders or to determine the status of an existing disorder identified in a subject. Such methods can include, for example, determining whether an individual has relatives who have been diagnosed with a particular disease. Screening methods can also include, for example, conventional work-ups to determine familial status for a particular disease known to have a heritable component (for example, in the case of BMT, clinical studies have shown that the presence of certain HLA-C alleles correlates with an increased risk for BM allograft rejection [see Scott et al., *Blood* 92:486-44871, 1998] and various cancers are also known to have certain inheritable components). Inheritable components of cancers include, for example, mutations in multiple genes that are transforming (e.g., Ras, Raf, EGFR, cMet and others), the presence or absence of certain HLA and killer inhibitory receptor (KIR) molecules, or mechanisms by which cancer cells are able to modulate immune suppression of cells like NK cells and T cells, either directly or indirectly (see, e.g., Ljunggren and Malmberg, *Nature Rev. Immunol.* 7:329-339, 2007; Boyton and Altmann, *Clin. Exp. Immunol.* 149:1-8, 2007). Toward this end, nucleotide probes can be routinely employed to identify individuals carrying genetic markers associated with a particular disease of interest. In addition, a wide variety of immunological methods are known in the art that are useful to identify markers for specific diseases. For example, various ELISA immunoassay methods are available and well-known in the art that employ monoclonal antibody probes to detect antigens associated with specific tumors. Screening may be implemented as indicated by known patient symptomology, age factors, related risk factors, etc. These methods allow the clinician to routinely select patients in need of the methods described herein for treatment. In accordance with these methods, modulation of NK cell activity may be implemented as an independent treatment program or as a follow-up, adjunct, or coordinate treatment regimen to other treatments.

For administration, the zB7H6 polypeptide, antibody, or other zB7H6-related agent is formulated as a pharmaceutical composition. A pharmaceutical composition comprising a soluble zB7H6 polypeptide, anti-zB7H6 antibody, or other agent can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), *Remington's Pharmaceutical Sciences* (Mack Publishing Company, 19th ed. 1995).) Formulations may further include one or more excipients, preservatives, solubilizers, buffering agents, albumin to prevent protein loss on vial surfaces, etc.

A pharmaceutical composition comprising a zB7H6 polypeptide, antibody, or other zB7H6-related agent is administered to a subject in an effective amount. According to the methods of the present invention, the polypeptide, antibody, or other agent may be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration. For prevention and treatment purposes, the agent may be administered to a subject in a single bolus delivery, via continuous delivery (e.g., continuous transdermal delivery) over an extended time period, or in a repeated administration protocol (e.g., on an hourly, daily, or weekly basis).

Determination of effective dosages in this context is typically based on animal model studies followed up by human clinical trials and is guided by determining effective dosages and administration protocols that significantly reduce the occurrence or severity of the subject disease or disorder in model subjects. Effective doses of the compositions of the present invention vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically or prophylactically effective amount is also one in which any undesired collateral effects are outweighed by beneficial effects of modulating NKp30-mediated NK cell activity. For administration of a soluble zB7H6 polypeptide or an antibody, a dosage typically ranges from about 0.1 µg to 100 mg/kg or 1 µg/kg to about 50 mg/kg, and more usually 10 µg to 5 mg/kg of the subject's body weight. In more specific embodiments, an effective amount of the agent is between about 1 µg/kg and about 20 mg/kg, between about 10 µg/kg and about 10 mg/kg, or between about 0.1 mg/kg and about 5 mg/kg. Dosages within this range can be achieved by single or multiple administrations, including, e.g., multiple administrations per day or daily, weekly, bi-weekly, or monthly administrations. For example, in certain variations, a regimen consists of an initial administration followed by multiple, subsequent administrations at weekly or bi-weekly intervals. Another regimen consists of an initial administration followed by multiple, subsequent administrations at monthly or bimonthly intervals. Alternatively, administrations can be on an irregular basis as indicated by monitoring of NK cell activity and/or clinical symptoms of the disease or disorder.

Dosage of the pharmaceutical composition may be varied by the attending clinician to maintain a desired concentration at a target site. For example, if an intravenous mode of delivery is selected, local concentration of the agent in the bloodstream at the target tissue may be between about 1-50 nanomoles of the composition per liter, sometimes between about 1.0 nanomole per liter and 10, 15, or 25 nanomoles per liter depending on the subject's status and projected measured response. Higher or lower concentrations may be selected based on the mode of delivery, e.g., trans-epidermal delivery versus delivery to a mucosal surface. Dosage should also be adjusted based on the release rate of the administered formulation, e.g., nasal spray versus powder, sustained release oral or injected particles, transdermal formulations, etc. To achieve the same serum concentration level, for example, slow-release particles with a release rate of 5 nanomolar (under standard conditions) would be administered at about twice the dosage of particles with a release rate of 10 nanomolar.

A pharmaceutical composition comprising a soluble zB7H6 polypeptide, antibody, or other zB7H6-related composition can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants. (See, e.g., Bremer et al., *Pharm. Biotechnol.* 10:239, 1997; Ranade, "Implants in Drug Delivery," in *Drug Delivery Systems* 95-123 (Ranade and Hollinger, eds., CRC Press 1995); Bremer et al., "Protein Delivery with Infusion Pumps," in *Protein Delivery: Physical Systems* 239-254 (Sanders and Hendren, eds., Plenum Press 1997); Yewey et al., "Delivery of Proteins from a Controlled Release Injectable Implant," in *Protein Delivery: Physical Systems* 93-117 (Sanders and Hendren, eds., Plenum Press 1997).) Other solid forms include creams, pastes, other topological applications, and the like.

Liposomes provide one means to deliver therapeutic polypeptides to a subject, e.g., intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments. (See, generally, Bakker-Woudenberg et al., *Eur. J. Clin. Microbiol. Infect. Dis.* 12 (Suppl. 1):S61, 1993; Kim, *Drugs* 46:618, 1993; Ranade, "Site-Specific Drug Delivery Using Liposomes as Carriers," in *Drug Delivery Systems* 3-24 (Ranade and Hollinger, eds., CRC Press 1995).) Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s). (See, e.g., Machy et al., *Liposomes In Cell Biology And Pharmacology* (John Libbey 1987); Ostro et al., *American J. Hosp. Pharm.* 46:1576, 1989.) Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (see Scherphof et al., *Ann. N.Y. Acad. Sci.* 446:368, 1985). After intravenous administration, small liposomes (0.1 to 1.0 µm) are typically taken up by cells of the reticuloendothelial system, located principally in the liver and spleen, whereas liposomes larger than 3.0 µm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (see Claassen et al., *Biochim. Biophys. Acta* 802:428, 1984). In addition, incorporation of glycolipid- or polyethelene glycol-derivatized phospholipids into liposome membranes has been shown to result in a significantly reduced uptake by the reticuloendothelial system (see Allen et al., *Biochim. Biophys. Acta* 1068:133, 1991; Allen et al., *Biochim. Biophys. Acta* 1150:9, 1993).

Liposomes can also be prepared to target particular cells or organs by varying phospholipid composition or by inserting receptors or counter-receptors into the liposomes. For example, liposomes, prepared with a high content of a non-ionic surfactant, have been used to target the liver. (See, e.g., Japanese Patent 04-244,018 to Hayakawa et al.; Kato et al., *Biol. Pharm. Bull.* 16:960, 1993.) These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver. (See Shimizu et al., *Biol. Pharm. Bull.* 20:881, 1997.)

Alternatively, various targeting counter-receptors can be bound to the surface of the liposome, such as antibodies, antibody fragments, carbohydrates, vitamins, and transport proteins. For example, for targeting to the liver, liposomes can be modified with branched type galactosyllipid derivatives to target asialoglycoprotein (galactose) receptors, which are exclusively expressed on the surface of liver cells. (See Kato and Sugiyama, *Crit. Rev. Ther. Drug Carrier Syst.* 14:287, 1997; Murahashi et al., *Biol. Pharm. Bull.* 20:259, 1997.) In a more general approach to tissue targeting, target cells are prelabeled with biotinylated antibodies specific for a counter-receptor expressed by the target cell. (See Harasym et al., *Adv. Drug Deliv. Rev.* 32:99, 1998.) After plasma elimination of free antibody, streptavidin-conjugated liposomes are administered. In another approach, targeting antibodies are directly attached to liposomes. (See Harasym et al., supra.)

Polypeptides and antibodies can be encapsulated within liposomes using standard techniques of protein microencapsulation. (See, e.g., Anderson et al., *Infect. Immun.* 31:1099, 1981; Anderson et al., *Cancer Res.* 50:1853, 1990; Cohen et al., *Biochim. Biophys. Acta* 1063:95, 1991; Alving et al. "Preparation and Use of Liposomes in Immunological Studies," in *Liposome Technology* (Vol. III) 317 (Gregoriadis, ed., CRC Press, 2nd ed. 1993); Wassef et al., *Meth. Enzymol.* 149:124, 1987.) As noted above, therapeutically useful liposomes may contain a variety of components. For example, liposomes may comprise lipid derivatives of poly(ethylene glycol). (See Allen et al., *Biochim. Biophys. Acta* 1150:9, 1993.)

Degradable polymer micro spheres have been designed to maintain high systemic levels of therapeutic proteins. Micro spheres are prepared from degradable polymers such as poly (lactide-co-glycolide) (PLG), polyanhydrides, poly (ortho esters), nonbiodegradable ethylvinyl acetate polymers, in which proteins are entrapped in the polymer. (See, e.g., Gombotz and Pettit, *Bioconjugate Chem.* 6:332, 1995; Ranade, "Role of Polymers in Drug Delivery," in *Drug Delivery Systems* 51-93 (Ranade and Hollinger, eds., CRC Press 1995); Roskos and Maskiewicz, "Degradable Controlled Release Systems Useful for Protein Delivery," in *Protein Delivery: Physical Systems* 45-92 (Sanders and Hendren, eds., Plenum Press 1997); Bartus et al., *Science* 281:1161, 1998; Putney and Burke, *Nature Biotechnology* 16:153, 1998; Putney, *Curr. Opin. Chem. Biol.* 2:548, 1998.) Polyethylene glycol (PEG)-coated nanospheres can also provide carriers for intravenous administration of therapeutic proteins. (See, e.g., Gref et al., *Pharm. Biotechnol.* 10:167, 1997.)

Other dosage forms can be devised by those skilled in the art, as shown by, e.g., Ansel and Popovich, *Pharmaceutical Dosage Forms and Drug Delivery Systems* (Lea & Febiger, 5th ed. 1990); Gennaro (ed.), *Remington's Pharmaceutical Sciences* (Mack Publishing Company, 19th ed. 1995), and Ranade and Hollinger, *Drug Delivery Systems* (CRC Press 1996).

zB7H6 polypeptides can be used in the context of gene therapy. Gene therapy can be broadly defined as the transfer of genetic material into a cell to transiently or permanently alter the cellular phenotype. Numerous methods are being developed for delivery of cytokines, tumor antigens, and additional co-stimulatory molecules via gene therapy to specific locations within tumor patients (see generally Rosenberg (ed.), *Principles and practice of the biologic therapy of cancer* (Lippincott Williams & Wilkins, Philadelphia, Pa., 3rd ed. 2000)). These methodologies could be adapted to use zB7H6 DNA or RNA.

Accordingly, in some embodiments, NK cell responses in a subject are modulated by administration of a nucleic acid encoding a zB7H6 protein, including, e.g., a soluble zB7H6 polypeptide as described herein. Using such zB7H6-encoding nucleic acids, disease or disorders characterized by insufficient NK cell activity can be treated as generally discussed above. In the case of nucleic acid therapy, a zB7H6 polypeptide may be expressed as a soluble receptor, which is secreted from cells to induce NKp30-mediated effects in a manner similar to a soluble zB7H6 polypeptide that is directly administered to a subject as described above. Alternatively, a zB7H6 polypeptide may be expressed in a form that maintains association with the surface of the cell in which the protein is expressed (e.g., with a functional transmembrane domain or a GPI linkage); such embodiments are particularly useful for facilitating targeting to particular cells or tissues to maintain localized NKp30-mediated effects.

zB7H6 polypeptide-encoding nucleic acids for use in therapeutic methods can be DNA or RNA. A nucleic acid segment encoding the zB7H6 polypeptide is typically linked to regulatory elements, such as a promoter and enhancer, that allow expression of the DNA segment in the intended target cells of a patient. For expression in blood cells, as is desirable for induction of a NK cell-mediated responses via expression of zB7H6 polypeptides, promoter and enhancer elements from light or heavy chain immunoglobulin genes or the CMV major intermediate early promoter and enhancer are suitable to direct expression. The linked regulatory elements and coding sequences are often cloned into a vector.

A number of viral vector systems are available including retroviral systems (see, e.g., Lawrie and Tumin, *Cur. Opin. Genet. Develop.* 3, 102-109, 1993); adenoviral vectors (see, e.g., Bett et al., *J. Virol.* 67, 5911, 1993); adeno-associated virus vectors (see, e.g., Zhou et al., *J. Exp. Med.* 179, 1867, 1994), viral vectors from the pox family including vaccinia virus and the avian pox viruses, viral vectors from the alpha virus genus such as those derived from Sindbis and Semliki Forest Viruses (see, e.g., Dubensky et al., *J. Virol.* 70, 508-519, 1996), and papillomaviruses (Ohe et al., *Human Gene Therapy* 6, 325-333, 1995; WO 94/12629 (Woo et al.); Xiao & Brandsma, *Nucleic Acids. Res.* 24, 2630-2622, 1996).

Nucleic acids may be also used to decrease the level of functional zB7H6 expression in cells. For example, nucleic acids for use in therapeutic methods may include, for example, inhibitory polynucleotides (e.g., antisense polynucleotides, small inhibitory RNAs (siRNA), ribozymes, and external guide sequences), as well as nucleic acids encoding zB7H6 dominant negative variants. Such nucleic acids can be used to inhibit zB7H6 activity in a subject by reducing the level of NKp30 interaction with functional zB7H6.

DNA encoding a zB7H6 polypeptide, or a vector containing the same, can be packaged into liposomes. Suitable lipids and related analogs are described by U.S. Pat. Nos. 5,208,036, 5,264,618, 5,279,833 and 5,283,185. Vectors and DNA encoding a zB7H6 polypeptide can also be adsorbed to or associated with particulate carriers, examples of which include polymethyl methacrylate polymers and polylactides and poly(lactide-co-glycolides) (see, e.g., McGee et al., *J. Micro Encap.,* 1996).

Gene therapy vectors or naked DNA can be delivered in vivo by administration to an individual patient, typically by systemic administration (e.g., intravenous, intraperitoneal, nasal, gastric, intradermal, intramuscular, subdermal, or intracranial infusion) or topical application (see e.g., U.S. Pat. No. 5,399,346). DNA can also be administered using a gene gun. (See Xiao & Brandsma, supra.) The DNA encoding a polypeptide is precipitated onto the surface of microscopic metal beads. The microprojectiles are accelerated with a shock wave or expanding helium gas, and penetrate tissues to a depth of several cell layers. For example, The Accel™ Gene Delivery Device manufactured by Agacetus, Inc. Middleton Wis. is suitable. Alternatively, naked DNA can pass through skin into the blood stream simply by spotting the DNA onto skin with chemical or mechanical irritation (see, e.g., WO 95/05853).

In a further variation, vectors encoding a zB7H6 polypeptide can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

In certain embodiments, the methods may additionally involve the use of viruses or other delivery vehicles that specifically recognize a target cell or tissue (e.g., tumor-targeted viruses, or other delivery vehicles that specifically recognize tumor cells.)

Pharmaceutical compositions as described herein may also be used in the context of combination therapy. The term "combination therapy" is used herein to denote that a subject is administered at least one therapeutically effective dose of a zB7H6-related composition and another agent. The zB7H6-related composition may be, e.g., a soluble zB7H6 polypeptide, an anti-zB7H6 antibody (including, e.g., an anti-zB7H6 antibody-drug conjugate), a zB7H6 mimicking agent such as a zB7H6 anti-idiotypic antibody, a zB7H6-encoding polynucleotide, an inhibitory polynucleotide, or other agent that demonstrates zB7H6 biological activity, inhibition of zB7H6 biological activity, or specific binding to zB7H6 (such as, e.g., in the context of targeting therapeutic agents to zB7H6-expressing cells).

For example, in the context of cancer immunotherapy, compositions having zB7H6 biological activity can be used as an immunostimulatory agent in combination with chemotherapy, radiation, and myeloablation. zB7H6 polypeptides and other agents having zB7H6 biological activity can work in synergy with conventional types of chemotherapy or radiation. For instance, in preclinical models of lymphoma and renal cell carcinoma, the combination of IL-2 with doxorubicin (Ehrke et al., *Cancer Immunol. Immunother.* 42:221-30, 1996), or the combinations of IL-2 (Younes et al., *Cell Immunol.* 165:243-51, 1995) or IFN-α (Nishisaka et al., *Cytokines Cell Mol. Ther.* 6:199-206, 2000) with radiation provided superior results over the use of single agents. In this setting, zB7H6 polypeptides and zB7H6 mimicking agents can further reduce tumor burden and allow more efficient killing by the chemotherapeutic. Additionally, lethal doses of chemotherapy or radiation followed by bone marrow transplantation or stem cell reconstitution could reduce tumor burden to a sufficiently small level (e.g., minimal residual disease) to better allow for a zB7H6-mediated anti-tumor effect. Examples of this type of treatment regimen include the uses of IL-2 and IFN-α to modify anti-cancer responses following myeloablation and transplantation (Porrata et al., *Bone Marrow Transplant.* 28:673-80, 2001; Slavin and Nagler, *Cancer J. Sci. Am. Suppl* 1:S59-67, 1997; Fefer et al., *Cancer J. Sci. Am. Suppl* 1:S48-53, 1997). In the case of lymphoma and other cancers, depending on when a zB7H6-related composition is used relative to the chemotherapeutic agent(s), the zB7H6-related composition may be employed to directly synergize with the chemotherapeutic agent's effect on the tumor cells or alternatively employed after the chemotherapy to stimulate the immune system. Those skilled in the art would design a protocol to take advantage of both possibilities.

Compositions of the present invention demonstrating zB7H6 biological activity can be used in combination with other immunomodulatory compounds including various cytokines and co-stimulatory/inhibitory molecules. For example, the NK cell stimulatory activity of zB7H6 in mediating an anti-cancer response can be enhanced in patients when compositions having zB7H6 activity are used with other classes of immunomodulatory molecules. These could include, but are not limited to, the use of additional cytokines. For instance, the combined use of IL-2 and IL-12 shows beneficial effects in T-cell lymphoma, squamous cell carcinoma, and lung cancer. (See Zaki et al., *J. Invest. Dermatol.* 118:366-71, 2002; Li et al., *Arch. Otolayngol. Head Neck Surg.* 127:1319-24, 2001; Hiraki et al., *Lung Cancer* 35:329-33, 2002.) In addition, compositions having zB7H6 activity could be combined with reagents that co-stimulate various cell surface molecules found on immune-based effector cells, such as the activation of CD137. (See Wilcox et al., *J. Clin. Invest.* 109:651-9, 2002) or inhibition of CTLA4 (Chambers et al., *Ann. Rev. Immunol.* 19:565-94, 2001.) Alternatively, composition having zB7H6 activity could be used with reagents that induce tumor cell apoptosis by interacting with TRAIL-related receptors. (See, e.g., Takeda et al., *J. Exp. Med.* 195:161-9, 2002; Srivastava, *Neoplasia* 3:535-46, 2001.) Such reagents include TRAIL ligand, TRAIL ligand-Ig fusions, anti-TRAIL antibodies, and the like.

In other variations, compositions having zB7H6 activity are used in combination with monoclonal antibody therapy. Such combination therapy is particularly useful for treatment of cancer, in which the use of monoclonal antibodies is becoming a standard practice for many tumors including Non-Hodgkins lymphoma (rituximab or RITUXAN®), forms of leukemia (gemtuzumab or MYLOTARG®), breast cell carcinoma (trastuzumab or HERCEPTIN®), and colon carcinoma (cetuximab or ERBITUX®). One mechanism by which antibodies mediate an anti-cancer effect is through a process referred to as antibody-dependent cell-mediated cytotoxicity (ADCC) in which immune-based cells, including NK cells, macrophages, and neutrophils, kill those cells that are bound by the antibody complex. Accordingly, due to its immunomodulatory in triggering NKp30-mediated NK cell activity, zB7H6 can be used to enhance the effectiveness of antibody therapy. Examples of this type of treatment paradigm include the combination use of RITUXAN™ (rituximab) and either IL-2, IL-12, or IFN-α for the treatment of Hodgkin's and Non-Hodgkin's lymphoma. (See Keilholz et al., *Leuk. Lymphoma* 35:641-2, 1999; Ansell et al., *Blood* 99:67-74, 2002; Carson et al., *Eur. J. Immunol.* 31:3016-25, 2001; Sacchi et al., *Haematologica* 86:951-8, 2001.)

Pharmaceutical compositions may be supplied as a kit comprising a container that comprises a therapeutic polypeptide or polynucleotide as described herein. A therapeutic molecule can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide or polynucleotide. Such a kit may further comprise written information on indications and usage of the pharmaceutical composition. For example, such information may include a statement that a zB7H6 composition is contraindicated in patients with known hypersensitivity to zB7H6.

B. Cancer Treatment

1. Types of Cancer

As described herein, zB7H6 is an activating ligand for the stimulatory NK cell receptor, NKp30. As such, in certain variations, agents having agonistic zB7H6 activity against NKp30 may be used as immunostimulatory agents for cancer therapy by enhancing direct tumor killing by NK cells via induction of NKp30-mediated NK cell cytolytic activity. In addition, as shown by studies described herein, zB7H6 is expressed on a variety of tumor-derived cells. Accordingly, in other variations, a zB7H6 antibody may be used to direct killing of a zB7H6-expressing cell by activating the ADCC or CDC pathway through binding of Fc to Fc receptors and the complement protein, C1q. In yet other variations, an anti-zB7H6 antibody-drug conjugate, comprising a cytotoxic agent conjugated to an anti-zB7H6 antibody, may be used to deliver a cytotoxic agent to zB7H6-expressing cancer cells, where the cytotoxic agent exerts a therapeutic effect by depleting or inhibition the growth of the cancer cells.

Table 4 below lists some cancers amenable to treatment in accordance with the present invention, organized predominantly by target tissues.

TABLE 4

List of Exemplary Cancer Types

1. Head and Neck cancer
    a. Brain
    b. Oral cavity
    c. Orophyarynx
    d. Nasopharynx
    e. Hypopharynx
    f. Nasal cavities and paranasal sinuses
    g. Larynx
    h. Lip
2. Lung cancers
    a. Non-small cell carcinoma
    b. Small cell carcinoma
3. Gastrointestinal Tract cancers
    a. Colorectal cancer
    b. Gastric cancer
    c. Esophageal cancer
    d. Anal cancer
    e. Extrahepatic Bile Duct cancer
    f. Cancer of the Ampulla of Vater
    g. Gastrointestinal Stromal Tumor (GIST)
4. Liver cancer
    a. Liver Cell Adenoma
    b. Hepatocellular Carcinoma
5. Breast cancer TABLE 4-continued List of Exemplary Cancer Types 6. Gynecologic cancer
    a. Cervical cancer
    b. Ovarian cancer
    c. Vaginal cancer
    d. Vulvar cancer
    e. Gestational Trophoblastic Neoplasia
    f. Uterine cancer
7. Urinary Tract cancer
    a. Renal cancer carcinoma
    b. Prostate cancer
    c. Urinary Bladder cancer
    d. Penile cancer
    e. Urethral cancer
8. Urinary Bladder cancer
9. Neurological Tumors
    a. Astrocytoma and glioblastoma
    b. Primary CNS lymphoma
    c. Medulloblastoma
    d. Germ Cell tumors
    e. Retinoblastoma
10. Endocrine Neoplasms
    a. Thyroid cancer
    b. Pancreatic cancer
        1) Islet Cell tumors
            a) Insulinomas
            b) Glucagonomas
    c. Pheochromocytoma
    d. Adrenal carcinoma
    e. Carcinoid tumors
    f. Parathyroid cancinoma
    g. Pineal gland neoplasms
11. Skin cancers
    a. Malignant melanoma
    b. Squamous Cell carcinoma
    c. Basal Cell carcinoma
    d. Kaposi's Sarcoma
12. Bone cancers
    a. Osteoblastoma
    b. Osteochondroma
    c. Osteosarcoma
13. Connective Tissue neoplasms
    a. Chondroblastoma
    b. Chondroma
14. Hematopoietic malignancies
    a. Non-Hodgkin Lymphoma
        1) B-cell lymphoma
        2) T-cell lymphoma
        3) Undifferentiated lymphoma
    b. Leukemias
        1) Chronic Myelogenous Leukemia
        2) Hairy Cell Leukemia
        3) Chronic Lymphocytic Leukemia
        4) Chronic Myelomonocytic Leukemia
        5) Acute Myelocytic Leukemia
        6) Acute Lymphoblastic Leukemia
    c. Myeloproliferative Disorders
        1) Multiple Myeloma
        2) Essential Thrombocythemia
        3) Myelofibrosis with Myeloid Metaplasia
        4) Hypereosinophilic Syndrome
        5) Chronic Eosinophilic Leukemia
        6) Polycythemia Vera
    d. Hodgkin Lymphoma
15. Childhood Cancers
    a. Leukemia and Lymphomas
    b. Brain cancers
    c. Neuroblastoma
    d. Wilm's Tumor (nephroblastoma)
    e. Phabdomyosarcoma
    f. Retinoblastoma
16. Immunotherapeutically sensitive cancers
    a. melanoma
    b. kidney cancer
    c. leukemias, lymphomas and myelomas
    d. breast cancer
    e. prostate cancer
    f. colorectal cancer
    g. cervical cancer TABLE 4-continued List of Exemplary Cancer Types h.  ovarian cancer
    i.  lung cancer Some of the cancers listed above, including some of the relevant animal models for evaluating the effects of an zB7H6-related agent in accordance with the present invention on tumor responses, are discussed in further detail below.

a. Chronic Myeloid Leukemia

Chronic myeloid leukemia (CML) is a rare type of cancer affecting mostly adults. It is a cancer of granulocytes (one of the main types of white blood cells). In CML many granulocytes are produced and they are released into the blood when they are immature and unable to work properly. The immature white blood cells are known as blasts. The production of other types of blood cells is also disrupted. Normally, white blood cells repair and reproduce themselves in an orderly and controlled manner, but in chronic myeloid leukaemia the process gets out of control and the cells continue to divide and mature abnormally. The disease usually develops very slowly, which is why it is called "chronic" myeloid leukemia.

Because CML develops (progresses) slowly, it is difficult to detect in its early stages. Sometimes it is discovered only when a blood test is done for another reason. The symptoms of CML are often vague and non-specific and are caused by the increased number of abnormal white blood cells in the bone marrow and the reduced number of normal blood cells: a feeling of fullness or a tender lump on the left side of the abdomen. This is because, in CML, the spleen can become enlarged. The spleen is an organ which lies just below the ribs on the left side of the abdomen. It filters the blood and removes worn-out red blood cells. The swelling of the spleen may also cause pressure on the stomach, which can lead to indigestion and poor appetite some people feel tired and look pale, due to a lack of red blood cells (anemia) due to a lower number of platelets in the blood some people may notice that they bleed or bruise more easily. As well as bruising more easily than normal, a special type of bruising can be seen. This consists of small blood-like spots usually seen on the legs or in the mouth and is called petechiae. Women may find that their periods become very much heavier. However, these symptoms and signs are rare some people may notice a generalised itching. Chronic myeloid leukaemia can occur at any age, but it more commonly affects middle-aged and older people. It is rare in children (cancerbacup internet website). The effects of an agent (e.g., an anti-zB7H6 antibody-drug conjugate) on tumor response can be evaluated, for example, in a human tumor xenograft model, using human CML cells engrafted in immunodeficient mice (see, e.g., Ren, *Leukemia and Lymphoma* 8:1549-1561, 2002; Van Etten, *Blood Cells Mol. Dis.* 27:201-205, 2001; Wong and Witte, *Oncogene* 20:5644-5659, 2001).

b. Multiple Myeloma

Multiple myeloma is a type of cancer affecting certain white blood cells called plasma cells. When cancer involves plasma cells, the body keeps producing more and more of these cells. The unneeded plasma cells—all abnormal and all exactly alike—are called myeloma cells. Myeloma cells tend to collect in the bone marrow and in the hard, outer part of bones. Sometimes they collect in only one bone and form a single mass, or tumor, called a plasmacytoma. In most cases, however, the myeloma cells collect in many bones, often forming many tumors and causing other problems. When this happens, the disease is called multiple myeloma.

Because people with multiple myeloma have an abnormally large number of identical plasma cells, they also have too much of one type of antibody. These myeloma cells and antibodies can cause a number of serious medical problems. (1) As myeloma cells increase in number, they damage and weaken bones, causing pain and sometimes fractures. Bone pain can make it difficult for patients to move. (2) When bones are damaged, calcium is released into the blood. This may lead to hypercalcemia—too much calcium in the blood. Hypercalcemia can cause loss of appetite, nausea, thirst, fatigue, muscle weakness, restlessness, and confusion. (3) Myeloma cells prevent the bone marrow from forming normal plasma cells and other white blood cells that are important to the immune system. Patients may not be able to fight infection and disease. (4) The cancer cells also may prevent the growth of new red blood cells, causing anemia. Patients with anemia may feel unusually tired or weak. And (5) Multiple myeloma patients may have serious problems with their kidneys. Excess antibody proteins and calcium can prevent the kidneys from filtering and cleaning the blood properly. Symptoms of multiple myeloma depend on how advanced the disease is. In the earliest stage of the disease, there may be no symptoms. When symptoms do occur, patients commonly have bone pain, often in the back or ribs. Patients also may have broken bones, weakness, fatigue, weight loss, or repeated infections. When the disease is advanced, symptoms may include nausea, vomiting, constipation, problems with urination, and weakness or numbness in the legs (National Cancer Institute's Internet website). The effects of an agent (e.g., an anti-zB7H6 antibody-drug conjugate) on tumor response can be evaluated in a human tumor xenograft model in immunodeficient mice, such as described in Miyakawa et al., *Biochem. Biophys. Res. Comm n.* 313:258-62, 2004.

c. Non-Hodgkin's Lymphoma

Non-Hodgkin's lymphomas are a type of cancer of the lymphatic system. There are two main types of lymphoma. One is called Hodgkin's disease (named after Dr. Hodgkin, who first described it). The other is called non-Hodgkin's lymphoma. There are about 20 different types of non-Hodgkin's lymphoma. In most cases of Hodgkin's disease, a particular cell known as the Reed-Sternberg cell is found in the biopsies. This cell is not usually found in other lymphomas, so they are called non-Hodgkin's lymphoma. This may not seem a very big difference, but it is important because the treatment for Hodgkin's and non-Hodgkin's lymphomas can be very different.

Often, the first sign of a non-Hodgkin's lymphoma is a painless swelling of a lymph node in the neck, armpit or groin. Other symptoms may include any of the following: night sweats or unexplained high temperatures (fever); loss of appetite, unexplained weight loss and excessive tiredness; children may develop a cough or breathlessness. They may also complain of abdominal pain, or you may notice a lump in your child's abdomen or persistent itching of the skin all over the body (cancerbacup internet website). The effects of an agent (e.g., an anti-zB7H6 antibody-drug conjugate) on tumor response can be evaluated in a non-Hodgkin's lymphoma xenograft model similar to that described in Ansell et al., *Leukemia* 18:616-23, 2004.

The classification of Non-Hodgkin's lymphomas most commonly used is the REAL classification system (Ottensmeier, *Chemico-Biological Interactions* 135-136:653-664, 2001.) Specific immunological markers have been identified for classifications of lymphomas. For example, follicular lymphoma markers include CD20+, CD3−, CD10+, CD5−; small lymphocytic lymphoma markers include CD20+, CD3−, CD10−, CD5+, CD23+; marginal zone B cell lymphoma markers include CD20+, CD3−, CD10−, CD23−; diffuse large B cell lymphoma markers include CD20+, CD3−; mantle cell lymphoma markers include CD20+, CD3−, CD10−, CD5+, CD23+; peripheral T cell lymphoma markers include CD20−, CD3+; primary mediastinal large B cell lymphoma markers include CD20+, CD3−, lymphoblastic lymphoma markers include CD20−, CD3+, Tdt+, and Burkitt's lymphoma markers include CD20+, CD3−, CD10+, CD5− (Decision Resourses, Non-Hodgkins Lymphoma, Waltham, Mass., February 2002).

Clinical classification of Non Hodgkins lymphoma (NHL) by the International Working Formulation breaks down disease into subtypes: (1) low grade (indolent) disease which includes small lymphocytic, consistent with chronic lymphocytic leukemia (SC); follicular, predominantly small cleaved cell (FSC); follicular, mixed small cleaved and large cell (FM); (2) intermediate grade disease which includes follicular, predominantly large cell (FL); diffuse, small cleaved cell (DSC); diffuse mixed, small and large cell (DM); diffuse, large cleaved or noncleaved cell (DL); and (3) high grade disease which includes immunoblastic, large cell (IBL); lymphoblastic, convoluted or nonconvoluted cell (LL); and small noncleaved cell, Burkitt's or non-Burkitts (SNC; (The Non-Hodgkin's Lymphoma Pathologic Classification Project, *Cancer* 49:2112-35, 1982). The Ann Arbor Staging system is commonly used to stage patients with NHL. Stage I means involvement of a single lymph node region or localized involvement of a single extralymphatic organ or site. Stage II means involvement of two or more lymph node regions on the same side of the diaphragm or localized involvement of an extranoldal site or organ and one or more lymph node regions on the same side of the diaphragm. Stage III means involvement of lymph node regions on both sides of the diaphragm, possibly accompanied by localized involvement of an extranodal organ or site. Stage 1V means diffuse or disseminated involvement of one or more distant extranodal organs with or without associated lymph node involvement ("Lymphoid neoplasms," In *American Joint Committee on Cancer: AJCC Cancer Staging Manual* 6th ed. New York, N.Y.: Springer, 2002, pp. 393-406). Rituximab has been shown effective in treating indolent and follicular lymphomas (Boye et al., *Annals of Oncol.* 14:520-535, 2003).

d. Cervical Cancer

The cervix is the neck of the uterus that opens into the vagina. Cervical cancer, also called cervical carcinoma, develops from abnormal cells on the surface of the cervix. Cervical cancer is one of the most common cancers affecting women. Cervical cancer is usually preceded by dysplasia, precancerous changes in the cells on the surface of the cervix. These abnormal cells can progress to invasive cancer. Once the cancer appears it can progress through four stages. The stages are defined by the extent of spread of the cancer. The more the cancer has spread, the more extensive the treatment is likely to be. There are 2 main types of cervical cancer: (1) Squamous type (epidermoid cancer): This is the most common type, accounting for about 80% to 85% of cervical cancers. This cancer may be caused by sexually transmitted diseases. One such sexual disease is the human papillomavirus, which causes venereal warts. The cancerous tumor grows on and into the cervix. This cancer generally starts on the surface of the cervix and may be diagnosed at an early stage by a Pap smear. (2) Adenocarcinoma: This type of cervical cancer develops from the tissue in the cervical glands in the canal of the cervix. Early cervical cancer usually causes no symptoms. The cancer is usually detected by a Pap smear and pelvic exam. Later stages of cervical cancer cause abnormal vaginal bleeding or a bloodstained discharge at unexpected times, such as between menstrual periods, after intercourse, or after menopause. Abnormal vaginal discharge may be cloudy or bloody or may contain mucus with a bad odor. Advanced stages of the cancer may cause pain (University of Michigan Health System Internet website). The effects of an agent (e.g., an anti-zB7H6 antibody-drug conjugate) on tumor response can be evaluated in a human tumor xenograft model similar to that described in Downs et al., *Gynecol. Oncol.* 98:203-10, 2005; and Li et al., *Int. J. Gynecol. Cancer* 15:301-7, 2005.

e. Head and Neck Tumors

Most cancers of the head and neck are of a type called carcinoma (in particular squamous cell carcinoma). Carcinomas of the head and neck start in the cells that form the lining of the mouth, nose, throat or ear, or the surface layer covering the tongue. However, cancers of the head and neck can develop from other types of cells. Lymphoma develops from the cells of the lymphatic system. Sarcoma develops from the supportive cells which make up muscles, cartilage or blood vessels. Melanoma starts from cells called melanocytes, which give colour to the eyes and skin. The symptoms of a head and neck cancer will depend on where it is—for example, cancer of the tongue may cause some slurring of speech. The most common symptoms are an ulcer or sore area in the head or neck that does not heal within a few weeks; difficulty in swallowing, or pain when chewing or swallowing; trouble with breathing or speaking, such as persistent noisy breathing, slurred speech or a hoarse voice; a numb feeling in the mouth; a persistent blocked nose, or nose bleeds; persistent earache, ringing in the ear, or difficulty in hearing; a swelling or lump in the mouth or neck; pain in the face or upper jaw; in people who smoke or chew tobacco, pre-cancerous changes can occur in the lining of the mouth, or on the tongue. These can appear as persistent white patches (leukoplakia) or red patches (erythroplakia). They are usually painless but can sometimes be sore and may bleed (Cancerbacup Internet website). The effects of an agent (e.g., an anti-zB7H6 antibody-drug conjugate) on tumor response can be evaluated in a human head and neck tumor xenograft model similar to that described in Kuriakose et al., *Head Neck* 22:57-63, 2000; Cao et al., *Clin. Cancer Res.* 5:1925-34, 1999; Braakhuis et al., *Cancer Res.* 51:211-4, 1991; and Baker, *Laryngoscope* 95:43-56, 1985.

f. Brain Cancer

Tumors that begin in brain tissue are known as primary tumors of the brain. Primary brain tumors are named according to the type of cells or the part of the brain in which they begin. The most common primary brain tumors are gliomas. They begin in glial cells. There are many types of gliomas. (1) Astrocytoma—The tumor arises from star-shaped glial cells called astrocytes. In adults, astrocytomas most often arise in the cerebrum. In children, they occur in the brain stem, the cerebrum, and the cerebellum. A grade III astrocytoma is sometimes called an anaplastic astrocytoma. A grade IV astrocytoma is usually called a glioblastoma multiforme. (2) Brain stem glioma—The tumor occurs in the lowest part of the brain. Brain stem gliomas most often are diagnosed in young children and middle-aged adults. (3) Ependymoma—The tumor arises from cells that line the ventricles or the central canal of the spinal cord. They are most commonly found in children and young adults. (4) Oligodendroglioma—This rare tumor arises from cells that make the fatty substance that covers and protects nerves. These tumors usually occur in the cerebrum. They grow slowly and usually do not spread into surrounding brain tissue. They are most common in middle-aged adults. The symptoms of brain tumors depend on tumor size, type, and location. Symptoms may be caused when a tumor presses on a nerve or damages a certain area of the brain. They also may be caused when the brain swells or fluid builds up within the skull. These are the most common symptoms of brain tumors: Headaches (usually worse in the morning); Nausea or vomiting; Changes in speech, vision, or hearing; Problems balancing or walking; Changes in mood, personality, or ability to concentrate; Problems with memory; Muscle jerking or twitching (seizures or convulsions); and Numbness or tingling in the arms or legs (National Cancer Institute's Internet website). The effects of an agent (e.g., an anti-zB7H6 antibody-drug conjugate) on tumor response can be evaluated in a human glioma xenograft model similar to that described in Bello et al., *Clin. Cancer Res.* 8:3539-48, 2002.

g. Thyroid Cancer

Papillary and follicular thyroid cancers account for 80 to 90 percent of all thyroid cancers. Both types begin in the follicular cells of the thyroid. Most papillary and follicular thyroid cancers tend to grow slowly. If they are detected early, most can be treated successfully. Medullary thyroid cancer accounts for 5 to 10 percent of thyroid cancer cases. It arises in C cells, not follicular cells. Medullary thyroid cancer is easier to control if it is found and treated before it spreads to other parts of the body. Anaplastic thyroid cancer is the least common type of thyroid cancer (only 1 to 2 percent of cases). It arises in the follicular cells. The cancer cells are highly abnormal and difficult to recognize. This type of cancer is usually very hard to control because the cancer cells tend to grow and spread very quickly. Early thyroid cancer often does not cause symptoms. But as the cancer grows, symptoms may include: A lump, or nodule, in the front of the neck near the Adam's apple; Hoarseness or difficulty speaking in a normal voice; Swollen lymph nodes, especially in the neck; Difficulty swallowing or breathing; or Pain in the throat or neck (National Cancer Institute's Internet website). The effects of an agent (e.g., an anti-zB7H6 antibody-drug conjugate) on tumor response can be evaluated in a human tumor xenograft model similar to that described in Quidville et al., *Endocrinology* 145:2561-71, 2004.

h. Liver Cancer

There are two different types of primary liver cancer. The most common kind is called hepatoma or hepatocellular carcinoma (HCC), and arises from the main cells of the liver (the hepatocytes). This type is usually confined to the liver, although occasionally it spreads to other organs. It occurs mostly in people with a liver disease called cirrhosis. There is also a rarer sub-type of hepatoma called Fibrolamellar hepatoma, which may occur in younger people and is not related to previous liver disease. The other type of primary liver cancer is called cholangiocarcinoma or bile duct cancer, because it starts in the cells lining the bile ducts. Most people who develop hepatoma usually also have a condition called cirrhosis of the liver. This is a fine scarring throughout the liver which is due to a variety of causes including infection and heavy alcohol drinking over a long period of time. However, only a small proportion of people who have cirrhosis of the liver develop primary liver cancer. Infection with either the hepatitis B or hepatitis C virus can lead to liver cancer, and can also be the cause of cirrhosis, which increases the risk of developing hepatoma. People who have a rare condition called haemochromatosis, which causes excess deposits of iron in the body, have a higher chance of developing hepatoma. A zB7H6-related agent of the present invention (e.g., a soluble zB7H6 polypeptide or an anti-zB7H6 antibody-drug conjugate) may be used to treat, prevent, inhibit the progression of, delay the onset of, and/or reduce the severity or inhibit at least one of the conditions or symptoms associated with hepatocellular carcinoma. The hepatocellular carcinoma may or may not be associated with a hepatitis (e.g., hepatitis A, hepatitis B, hepatitis C and hepatitis D) infection. The effects of an agent (e.g., an anti-zB7H6 antibody-drug conjugate) on tumor response can be evaluated in a human tumor xenograft model similar to that described in Zhou et al., *Clin. Cancer Res.* 9:6030-7, 2003; and Huynh et al., *J. Cell Mol. Med.* 2008 (E-Published as a "Postprint," 10.1111/j.1582-4934.2008.00364.x, 2008, at Blackwell Synergy website).

i. Lung Cancer

The effects of an agent (e.g., an anti-zB7H6 antibody-drug conjugate) on tumor response can be evaluated in a human small/non-small cell lung carcinoma xenograft model. Briefly, human tumors are grafted into immunodeficient mice and these mice are treated with an agent, such as an anti-zB7H6 antibody-drug conjugate, alone or in combination with other agents. Efficacy of the treatment can be demonstrated by evaluating tumor growth (Nemati et al., *Clin Cancer Res.* 6:2075-86, 2000; and Hu et al., *Clin. Cancer Res.* 10:7662-70, 2004).

2. Endpoints and Anti-Tumor Activity for Solid Tumors

While each protocol may define tumor response assessments differently, exemplary guidelines can be found in *Clinical Research Associates Manual* (Southwest Oncology Group, CRAB, Seattle, Wash., Oct. 6, 1998, updated August 1999) ("CRA Manual"). According to the CRA Manual (see chapter 7, "Response Assessment"), tumor response means a reduction or elimination of all measurable lesions or metastases. Disease is generally considered measurable if it comprises bi-dimensionally measurable lesions with clearly defined margins by medical photograph or X-ray, computerized axial tomography (CT), magnetic resonance imaging (MRI), or palpation. Evaluable disease means the disease comprises uni-dimensionally measurable lesions, masses with margins not clearly defined, lesion with both diameters less than 0.5 cm, lesions on scan with either diameter smaller than the distance between cuts, palpable lesions with diameter less than 2 cm, or bone disease. Non-evaluable disease includes pleural effusions, ascites, and disease documented by indirect evidence. Previously radiated lesions that have not progressed are also generally considered non-evaluable.

The criteria for objective status are required for protocols to assess solid tumor response. Representative criteria include the following: (1) Complete Response (CR), defined as complete disappearance of all measurable and evaluable disease; no new lesions; no disease related symptoms; no evidence of non-evaluable disease; (2) Partial Response (PR) defined as greater than or equal to 50% decrease from baseline in the sum of products of perpendicular diameters of all measurable lesions; no progression of evaluable disease; no new lesions; applies to patients with at least one measurable lesion; (3) Progression, defined as 50% or an increase of 10 $cm^2$ in the sum of products of measurable lesions over the smallest sum observed using same techniques as baseline, or clear worsening of any evaluable disease, or reappearance of any lesion which had disappeared, or appearance of any new lesion, or failure to return for evaluation due to death or deteriorating condition (unless unrelated to this cancer); (4) Stable or No Response, defined as not qualifying for CR, PR, or Progression. (See *Clinical Research Associates Manual*, supra.)

Additional endpoints that are accepted within the oncology art include overall survival (OS), disease-free survival (DFS), objective response rate (ORR), time to progression (TTP), and progression-free survival (PFS) (see *Guidance for Industry: Clinical Trial Endpoints for the Approval of Cancer*

*Drugs and Biologics*, April 2005, Center for Drug Evaluation and Research, FDA, Rockville, Md.)

3. Combination Cancer Therapy

As previously discussed, in certain embodiments, a zB7H6 polypeptide, antibody, or other zB7H6-related agent is used in combination with a second agent for treatment of a disease or disorder. When used for treating cancer, a zB7H6 polypeptide, antibody, or other agent of the present invention, including, for example, an anti-zB7H6 antibody-drug conjugate, may be used in combination with conventional cancer therapies such as, e.g., surgery, radiotherapy, chemotherapy, or combinations thereof. In certain aspects, other therapeutic agents useful for combination cancer therapy with a zB7H6-related agent in accordance with the present invention include anti-angiogenic agents. In some other aspects, other therapeutic agents useful for combination therapy include an antagonist of certain factors that are involved in tumor growth such as, for example, EGFR, ErbB2 (Her2), ErbB3, ErbB4, or TNF. In some aspects, an agent in accordance with the present invention is co-administered with a cytokine (e.g., a cytokine that stimulates an immune response against a tumor). Exemplary combination therapies particularly amenable for treatment of cancer are described in further detail below.

a. Antibodies Targeting Tumor-Associated Antigens

As previously noted, antibody therapy has been particularly successful in cancer treatment because certain tumors either display unique antigens, lineage-specific antigens, or antigens present in excess amounts relative to normal cells. One of the mechanisms associated with the anti-tumor activity of monoclonal antibody therapy is antibody dependent cellular cytotoxicity (ADCC). In ADCC, monoclonal antibodies bind to a target cell (e.g., cancer cell) and specific effector cells expressing receptors for the monoclonal antibody (e.g., NK cells, monocytes, granulocytes) bind the monoclonal antibody/target cell complex resulting in target cell death. Accordingly, in certain variations of the present invention, a zB7H6 polypeptide, antibody, or other zB7H6-related agent having efficacy against a cancer is co-administered with a monoclonal antibody against a tumor-associated antigen. In those variations where an anti-zB7H6 antibody is utilized, either to induce anti-tumor activity via ADCC or CDC or, alternatively, in the context of an anti-zB7H6 antibody-drug conjugate, the monoclonal antibody used in the combination will be an antibody to a second tumor-specific or tumor-associated antigen. The dose and schedule of the MAbs is based on pharmacokinetic and toxicokinetic properties ascribed to the specific antibody co-administered, and should optimize these effects, while minimizing any toxicity that may be associated with administration of a zB7H6 polypeptide, antibody, or other zB7H6-related agent.

Combination therapy with a zB7H6-related agent as described herein and a monoclonal antibody against a tumor-associated antigen may be indicated when a first line treatment has failed and may be considered as a second line treatment. The present invention also provides using the combination as a first line treatment in patient populations that are newly diagnosed and have not been previously treated with anticancer agents ("de novo patients") and patients that have not previously received any monoclonal antibody therapy ("naïve patients").

A zB7H6-related agent as described herein is also useful in combination therapy with monoclonal antibodies against tumor-associated antigens in the absence of any direct antibody-mediated ADCC or CDC of tumor cells. For example, antibodies that block an inhibitory signal in the immune system can lead to augmented immune responses. Examples include (1) antibodies against molecules of the B7R family that have inhibitory function such as, cytotoxic T lymphocyte-associated antigen 4 (CTLA-4), programmed death-1 (PD-1), B and T lymphocyte attenuator (BTLA); (2) antibodies against inhibitory cytokines like IL-10, TGFβ; and (3) antibodies that deplete or inhibit functions of suppressive cells like anti-CD25 or CTLA-4. For example, anti-CTLA4 MAbs in both mice and humans are thought to either suppress function of immune-suppressive regulatory T cells (Tregs) or inhibit the inhibitory signal transmitted through binding of CTLA-4 on T cells to B7-1 or B7-2 molecules on APCs or tumor cells.

Table 6 is a non-exclusive list of monoclonal antibodies approved or being tested for which combination therapy in accordance with the present invention is possible.

TABLE 6

Monoclonal Antibody Therapies for Use in Combination with PDGFRβ and/or VEGF-A Antagonists

| Target | Drug Name | Clinical Indication | Company |
|---|---|---|---|
| TRAIL-R1 | HGS-ETR1 | Cancers | HGS |
| TRAIL-R2 | HGS-ETR2 | solid tumors | HGS |
| CD40 | SGN40 | MM | Seattle Genetics |
| HER2 | Herceptin | Breast cancer | Genentech |
| EGF-R | ABX-EGF | CRC, NSCLC, RCC | Abgenix |
| EGF-R | EMD72000 | solid tumors | Merck |
| EGF-R | MDX-214 | EGF-R-positive tumors | Medarex |
| EGF-R | Erbitux | CRC | Imclone |
| α5β3 integrin | Vitaxin | psoriasis, prostate cancer | AME/Lilly |
| CD152 | CTLA-4 | Cancers | Medarex |
| CD49e | Integrin α5 | Cancers | Protein Design Labs |
| MUC18 (TIM-like) | ABX-MA1 | Melanoma | |
| TAG-72 Mucin | Anatumomab | Cancers | |
| CD3 | Ecromeximab | Melanoma | Kyowa Hakko |
| CD64 (Fc GR1) | AntiCD64 | Cancers | Medarex |
| CEA | CEA-Cide | Cancers | Immunomedics |
| EpCAM | Panorex | colorectal cancer | Centocor |
| Lewis-Y-Ag | SGN15 | Cancers | Seattle Genetics | b. Tyrosine Kinase Inhibitors

In some embodiments, a zB7H6 polypeptide, antibody, or other zB7H6-related agent as described herein is used in combination with a tyrosine kinase inhibitor. Tyrosine kinases are enzymes that catalyze the transfer of the γ phosphate group from the adenosine triphosphate to target proteins. Tyrosine kinases can be classified as receptor and non-receptor protein tyrosine kinases. They play an essential role in diverse normal cellular processes, including activation through growth receptors and affect proliferation, survival and growth of various cell types. Additionally, they are thought to promote tumor cell proliferation, induce anti-apoptotic effects and promote angiogenesis and metastasis. In addition to activation through growth factors, protein kinase activation through somatic mutation is a common mechanism of tumorigenesis. Some of the mutations identified are in B-Raf kinase, FLt3 kinase, BCR-ABL kinase, c-KIT kinase, epidermal growth factor (EGFR) and PDGFR pathways. The Her2, VEGFR and c-Met are other significant receptor tyrosine kinase (RTK) pathways implicated in cancer progression and tumorigenesis. Because a large number of cellular processes are initiated by tyrosine kinases, they have been identified as key targets for inhibitors.

Tyrosine kinase inhibitors (TKIs) are small molecules that act inside the cell, competing with adenosine triphosphate (ATP) for binding to the catalytic tyrosine kinase domain of both receptor and non-receptor tyrosine kinases. This competitive binding blocks initiation of downstream signaling leading to effector functions associated with these signaling events like growth, survival, and angiogenesis. Using a structure and computational approach, a number of compounds from numerous medicinal chemistry combinatorial libraries was identified that inhibit tyrosine kinases.

Most TKIs are thought to inhibit growth of tumors through direct inhibition of the tumor cell or through inhibition of angiogenesis. Moreover, certain TKIs affect signaling through the VEGF family receptors, including sorafenib and sunitinib. In some cases TKIs have been shown to activate functions of dendritic cells and other innate immune cells, like NK cells. This has been recently reported in animal models for imatinib. Imatinib is a TKI that has shown to enhance killer activity by dendritic cells and NK cells (for review, see Smyth et al., *NEJM* 354:2282, 2006).

BAY 43-9006 (sorafenib, Nexavar®) and SU11248 (sunitinib, Sutent®) are two such TKIs that have been recently approved for use in metastatic renal cell carcinoma (RCC). A number of other TKIs are in late and early stage development for treatment of various types of cancer. Other TKIs include, but are not limited to: Imatinib mesylate (Gleevec®, Novartis); Gefitinib (Iressa®, AstraZeneca); Erlotinib hydrochloride (Tarceva®, Genentech); Vandetanib (Zactima®, AstraZeneca), Tipifarnib (Zarnestra®, Janssen-Cilag); Dasatinib (Sprycel®, Bristol Myers Squibb); Lonafarnib (Sarasar®, Schering Plough); Vatalanib succinate (Novartis, Schering AG); Lapatinib (Tykerb®, GlaxoSmithKline); Nilotinib (Novartis); Lestaurtinib (Cephalon); Pazopanib hydrochloride (GlaxoSmithKline); Axitinib (Pfizer); Canertinib dihydrochloride (Pfizer); Pelitinib (National Cancer Institute, Wyeth); Tandutinib (Millennium); Bosutinib (Wyeth); Semaxanib (Sugen, Taiho); AZD-2171 (AstraZeneca); VX-680 (Merck, Vertex); EXEL-0999 (Exelixis); ARRY-142886 (Array BioPharma, AstraZeneca); PD-0325901 (Pfizer); AMG-706 (Amgen); BIBF-1120 (Boehringer Ingelheim); SU-6668 (Taiho); CP-547632 (OSI); (AEE-788 (Novartis); BMS-582664 (Bristol-Myers Squibb); JNK-401 (Celgene); R-788 (Rigel); AZD-1152 HQPA (AstraZeneca); NM-3 (Genzyme Oncology); CP-868596 (Pfizer); BMS-599626 (Bristol-Myers Squibb); PTC-299 (PTC Therapeutics); ABT-869 (Abbott); EXEL-2880 (Exelixis); AG-024322 (Pfizer); XL-820 (Exelixis); OSI-930 (OSI); XL-184 (Exelixis); KRN-951 (Kirin Brewery); CP-724714 (OSI); E-7080 (Eisai); HKI-272 (Wyeth); CHIR-258 (Chiron); ZK-304709 (Schering AG); EXEL-7647 (Exelixis); BAY-57-9352 (Bayer); BIBW-2992 (Boehringer Ingelheim); AV-412 (AVEO); YN-968D1 (Advenchen Laboratories); Midostaurin (Novartis); Perifosine (AEterna Zentaris, Keryx, National Cancer Institute); AG-024322 (Pfizer); AZD-1152 (AstraZeneca); ON-01910Na (Onconova); and AZD-0530 (AstraZeneca).

c. Chemotherapy Combinations

In certain embodiments, a zB7H6 polypeptide, antibody, or other zB7H6-related agent is administered in combination with one or more chemotherapeutic agents. Chemotherapeutic agents have different modes of actions, for example, by influencing either DNA or RNA and interfering with cell cycle replication. Examples of chemotherapeutic agents that act at the DNA level or on the RNA level are anti-metabolites (such as Azathioprine, Cytarabine, Fludarabine phosphate, Fludarabine, Gemcitabine, cytarabine, Cladribine, capecitabine 6-mercaptopurine, 6-thioguanine, methotrexate, 5-fluoroouracil and hyroxyurea; alkylating agents (such as Melphalan, Busulfan, Cis-platin, Carboplatin, Cyclophosphamide, Ifosphamide, Dacarabazine, Procarbazine, Chlorambucil, Thiotepa, Lomustine, Temozolamide); anti-mitotic agents (such as Vinorelbine, Vincristine, Vinblastine, Docetaxel, Paclitaxel); topoisomerase inhibitors (such as Doxorubincin, Amsacrine, Irinotecan, Daunorubicin, Epirubicin, Mitomycin, Mitoxantrone, Idarubicin, Teniposide, Etoposide, Topotecan); antibiotics (such as actinomycin and bleomycin); asparaginase; anthracyclines or taxanes.

d. Radiotherapy Combinations

In some variations, a zB7H6 polypeptide, antibody, or other zB7H6-related agent is administered in combination with radiotherapy. Certain tumors can be treated with radiation or radiopharmaceuticals. Radiation therapy is generally used to treat unresectable or inoperable tumors and/or tumor metastases. Radiotherapy is typically delivered in three ways. External beam irradiation is administered at distance from the body and includes gamma rays ($^{60}$Co) and X-rays. Brachytherapy uses sources, for example $^{60}$Co, $^{137}$Cs, $^{192}$Ir, or $^{125}$I, with or in contact with a target tissue.

e. Hormonal Agent Combinations

In some embodiments, a zB7H6 polypeptide, antibody, or other zB7H6-related agent is administered in combination with a hormone or anti-hormone. Certain cancers are associated with hormonal dependency and include, for example, ovarian cancer, breast cancer, and prostate cancer. Hormonal-dependent cancer treatment may comprise use of anti-androgen or anti-estrogen compounds. Hormones and anti-hormones used in cancer therapy include Estramustine phosphate, Polyestradiol phosphate, Estradiol, Anastrozole, Exemestane, Letrozole, Tamoxifen, Megestrol acetate, Medroxyprogesterone acetate, Octreotide, Cyproterone acetate, Bicaltumide, Flutamide, Tritorelin, Leuprorelin, Buserelin and Goserelin.

VII. Methods of Screening

In another aspect, the present invention provides methods of screening for an agonsist or antagonstist of the interaction of zB7H6 with NKp30. Generally, such methods of screening for an antagonist include the following steps: (a) contacting an agent with a zB7H6 polypeptide in the presence of an NKp30 polypeptide; (b) detecting a measure of the interaction of the zB7H6 polypeptide with the NKp30 polypeptide; and (c) determining whether the level of the zB7H6/NKp30 interaction measured in step (b) is significantly less relative to the level of interaction measured for control zB7H6 and NKp30 polypeptides in the absence of the agent, such that if the level of zB7H6/NKp30 interaction is less, then the agent is identified as an antagonist of the interaction of zB7H6 with NKp30.

Methods of screening for an agonist generally include the following steps:
(a) contacting an agent with a zB7H6 polypeptide in the presence of an NKp30 polypeptide; (b) detecting a measure of the interaction of the zB7H6 polypeptide with the NKp30 polypeptide; and (c) determining whether the level of the zB7H6/NKp30 interaction measured in step (b) is significantly greater relative to the level of interaction measured for control zB7H6 and NKp30 polypeptides in the absence of the agent, such that if the level of zB7H6/NKp30 interaction is greater, then the agent is identified as an agonist of the interaction of zB7H6 with NKp30.

A measure of zB7H6 interaction with NKp30 can include, for example, detection of zB7H6 binding to NKp30 as well as the ability of the zB7H6 polypeptide to trigger NKp30-mediated cellular activity (e.g., cytolytic activity), or of the ability of the NKp30 polypeptide to trigger zB7H6-mediated cellular activity. For identifying agonists of the zB7H6/NKp30 interaction, particularly where the measure of the interaction is a level of NKp30- or zB7H6-mediated cellular activity, the methods can further include an additional control to determine whether the agent is capable of inducing the cellular activity in the absence of the zB7H6 polypeptide or NKp30 polypeptide, such that if the agent is capable of inducing the cellular activity in the absence of the zB7H6 polypeptide or NKp30 polypeptide, then the agent is not an agonist of the interaction of zB7H6 with NKp30.

zB7H6 polypeptides for use in the screening methods will generally comprise a zB7H6 extracellular domain, or a functional variant or fragment thereof. Accordingly, a zB7H6 polypeptide for use in screening will include a polypeptide region selected from the following:
 (i) the extracellular domain of the zB7H6 polypeptide of SEQ ID NO:2 (i.e., residues 25-266 of SEQ ID NO:2);
 (ii) a functional variant of the zB7H6 extracellular domain of (i), the variant having at least 80% identity with residues 25-266 of SEQ ID NO:2; and
 (iii) a functional fragment of the zB7H6 extracellular domain of (i) or of the domain variant of (ii).

In typical variations, the zB7H6 polypeptide includes the extracellular domain of the zB7H6 SEQ ID NO:2 (i.e., residues 25-266 of SEQ ID NO:2), or a functional variant having at least 90% or 95% sequence identity with residues 25-266 of SEQ ID NO:2. The zB7H6 polypeptide can be a soluble zB7H6 receptor as disclosed herein. In alternative variations, the zB7H6 polypeptide is a membrane-bound form of zB7H6 expressed on a cell (e.g., a zB7H6 polypeptide having a GPI linkage, or a zB7H6 polypeptide having a functional transmembrane domain, such as the zB7H6 polypeptide of SEQ ID NO:2, expressed on a recombinant cell).

Similarly, the NKp30 polypeptide for use in the screening method will include the extracellular domain of NKp30, or a functional variant or fragment thereof. Typically, the NKp30 polypeptide is a human NKp30 polypeptide or a polypeptide derived from human NKp30. The NKp30 polypeptide can be a soluble NKp30 receptor or a membrane-bound form of NKp30. In certain variations, the NKp30 is a full-length NKp30 protein (e.g., full-length human NKp30) expressed on cells; such embodiments are particularly amenable to, inter alia, use of NKp30-mediated cytolytic activity as a functional read-out to detect the interaction of zB7H6 with NKp30.

In certain variations utilizing zB7H6 or NKp30 polypeptides expressed on recombinant cells, a cDNA or gene encoding the zB7H6 or NKp30 receptor is combined with other genetic elements required for its expression (e.g., a transcription promoter), and the resulting expression vector is inserted into a host cell. Cells that express the DNA and produce functional receptor are selected and used within a variety of screening systems. Each component of the monomeric, homodimeric, heterodimeric and multimeric receptor complex can be expressed in the same cell. Moreover, the components of the monomeric, homodimeric, heterodimeric and multimeric receptor complex can also be fused to a transmembrane domain or other membrane fusion moiety to allow complex assembly and screening of transfectants. In some embodiments, each of the zB7H6 polypeptide and NKp30 polypeptide are expressed in separate host cells. Alternatively, only one of the zB7H6 and NKp30 polypeptides is expressed in a cell.

In an animal model system, the cell can be contacted with the candidate agent by administering the candidate agent to the animal. The candidate agent can be administered orally, intravenously, by infusion or injection, or the like.

Agents for use in screening can include any agent with a potential to structurally interact with biomolecules, particularly proteins, through non-covalent interactions, such as, for example, through hydrogen bonds, ionic bonds, van der Waals attractions, or hydrophobic interactions. Accordingly, many types of agents can be screened by the present methods. Suitable candidate agents include, for example, small molecules, nucleic acids, peptides, peptidomimetics, synthetic compounds, and/or natural compounds.

Agents for screening can include random and/or semi-random libraries of peptides and/or nucleic acids. In variations comprising expression of recombinant zB7H6 or NKp30 in host cells, a nucleic acid agent can be screened by contacting the cell of the expression system with the nucleic acid. In a specific example, a genomic or cDNA library can be introduced into and expressed in a population of recombinant cells expressing zB7H6 or NKp30 to identify a genetic agent that reduces or enhances the interaction of zB7H6 with NKp30.

In other embodiments, an agent to be screened is a peptidomimetic. The term "peptidomimetic" refers to a synthetic chemical compound that has substantially the same structural and functional characteristics as a protein, polypeptide, or peptide. Peptide analogs are commonly used in the pharmaceutical industry as non-peptide drugs with properties analogous to those of the template peptide. These types of non-peptide compounds are termed "peptide mimetics" or "peptidomimetics" (see, e.g., Fauchere, *J. Adv. Drug Res.* 15:29, 1986; Veber and Freidinger *TINS* p. 392, 1985; and Evans et al., *J. Med. Chem.* 30:1229, 1987). Peptide mimetics that are structurally similar to therapeutically useful peptides may be used to produce an equivalent or enhanced therapeutic or prophylactic effect. Generally, peptidomimetics are structurally similar to a paradigm polypeptide (e.g., a polypeptide that has a desired biological or pharmacological activity), but have one or more peptide linkages optionally replaced by a linkage selected from the group consisting of, e.g., —CH2NH—, —CH2S—, —CH2—CH2—, —CH=CH— (cis and trans), —COCH2—, —CH(OH)CH2—, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate natural amino acid conservative substitutions as long as such substitutions also do not substantially alter the mimetic's structure and/or activity.

Agents for screening can also be from libraries of synthetic and/or natural compounds. One example is a library of FDA-approved compounds that can be used by humans. In addition, synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.), and a rare chemical library is available from Aldrich (Milwaukee, Wis.).

Combinatorial libraries are available and/or can be prepared. Alternatively, libraries of natural compounds in the form of bacterial, fungal, plant, and animal extracts are also available, for example, from Pan Laboratories (Bothell, Wash.) or MycoSearch (N.C.), or can be prepared. Compounds isolated from natural sources, such as animals, bacteria, fungi, plant sources, including leaves and bark, and marine samples also can be screened as candidate agents.

Other suitable agents include antisense molecules, ribozymes, and antibodies (including single chain antibodies and Fv fragments). For example, an antisense molecule that binds to a translational or transcriptional start site, or a splice junction, can be a candidate agent. Additionally, natural and synthetically-produced libraries and compounds are readily modified through conventional chemical, physical, and biochemical means.

Screening of such libraries, including combinatorially generated libraries (e.g., peptide libraries) can be performed in a rapid and efficient way to screen a large number of related and/or unrelated compounds. Combinatorial approaches also lend themselves to rapid evolution of potential therapeutic agents by the creation of second, third and fourth generation compounds modeled on active, but otherwise undesirable compounds.

Preparation and screening of combinatorial chemical libraries is well known to those of skill in the art. Such combinatorial chemical libraries include, but are not limited to, peptide libraries (see, e.g., U.S. Pat. No. 5,010,175; Furka, *Int. J. Pept. Prot. Res.* 37:487-93, 1991; Houghton et al., *Nature* 354:84-88, 1991). Other chemistries for generating chemical diversity libraries also can be used. Such chemistries include, but are not limited to: peptoids (see, e.g., PCT Publication No. WO 91/19735), encoded peptides (see, e.g., PCT Publication WO 93/20242), random bio-oligomers (see, e.g., PCT Publication No. WO 92/00091), benzodiazepines (see, e.g., U.S. Pat. No. 5,288,514; Baum, C&EN, Jan. 18, 1993, p. 33), diversomers such as hydantoins, benzodiazepines and dipeptides (see, e.g., Hobbs et al., *Proc. Nat. Acad. Sci. USA* 90:6909-13, 1993), vinylogous polypeptides (see, e.g., Hagihara et al., *J. Amer. Chem. Soc.* 114:6568, 1992), nonpeptidal peptidomimetics with glucose scaffolding (see, e.g., Hirschmann et al., *J. Amer. Chem. Soc.* 114:9217-18, 1992), analogous organic syntheses of small compound libraries (see, e.g., Chen et al., *J. Amer. Chem. Soc.* 116:2661, 1994), oligocarbamates (see, e.g., Cho et al., *Science* 261: 1303, 1993), peptidyl phosphonates (see, e.g., Campbell et al., *J. Org. Chem.* 59:658, 1994), nucleic acid libraries (see, e.g., Ausubel et al., supra; Sambrook, supra), peptide nucleic acid libraries (see, e.g., U.S. Pat. No. 5,539,083), antibody libraries (see, e.g., Vaughn et al., *Nature Biotechnology*, 14:309-14, 1996 and PCT/US96/10287), carbohydrate libraries (see, e.g., Liang et al., *Science* 274:1520-22, 1996; U.S. Pat. No. 5,593,853), small organic molecule libraries, such as isoprenoids (see, e.g., U.S. Pat. No. 5,569,588), thiazolidinones and metathiazanones (see, e.g., U.S. Pat. No. 5,549,974), pyrrolidines (see, e.g., U.S. Pat. Nos. 5,525,735 and 5,519,134), morpholino compounds (see, e.g., U.S. Pat. No. 5,506,337), or the like.

Devices for the preparation of combinatorial libraries are commercially available (see, e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences, Columbia, Md.; etc.).

Agents that are initially identified by any of the foregoing screening methods can be further tested to validate the apparent activity. For example, subsequent validation can be performed with suitable animal models or ex vivo human cells. For in vivo validation using an animal model system, the basic format of such methods can involve administering an agent identified during an initial screen to an animal that serves as a model for an NK cell-associated disease or disorder and then determining if NK cell activity is modulated, or if other clinical symptoms of the disease or disorder are ameliorated. The animal models utilized in validation studies generally are mammals of any kind. Specific examples of suitable animals include, but are not limited to, primates, mice, and rats.

The invention is further illustrated by the following non-limiting examples.

EXAMPLE 1

Inhibition of NK-92 Cytolytic Activity Against K562 Targets with Soluble NKp30/VASP A cytolytic assay was performed with NK-92 cells as effectors against K562 targets.

NK-92 cells were washed 1× with HBSSF (Hank's buffered saline (Ca, Mg Free)+5% FBS) and resuspended in HBSSF at $1.35 \times 10^6$/ml (to achieve a 27:1 ratio). 150 µl of washed cells were plated in the top row of a U-bottom 96-well plate and serially diluted (1:3) into HBSSF.

K562 target cells were washed 1× with HBSSF and labeled at $1 \times 10^6$ cells/ml in 10 µM calcein AM Molecular probes #C1430 (2.5 µl/ml of 4 mM stock in DMSO, 4 mM=4 mg/ml) for 60 minutes at 37° C. Labeled cells were washed 2× in HBSSF and $1 \times 10^6$ cells were resuspended in 20 ml HBSSF (5000 cells/100 µl). 100 ul of suspended target cells were added to diluted effectors for a total volume of 200 ul. A soluble form of NKp30 (NKp30/VASP A1683F) was also added to some sets of serially diluted wells at a concentration of 2 µg/ml.

Effector and target cells were spun at 500 rpm for 2 min, incubated at 37° C. for 3 hours, spun at 1500 rpm for 5 min, and then 100 µl supernatant transferred to a new flat bottom 96-well. Flat bottom plates containing transferred supernatants were read on a fluorometer for 1 second at an excitation wavelength of 485 nm and emission wavelength of 535 nm.

Figure 1A:
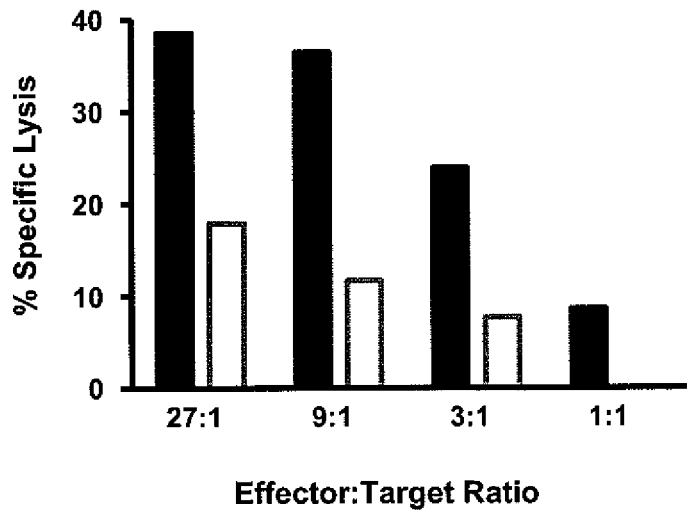
FIGS. 1A and 1B depict inhibition of NK-92 cytolytic activity against K562 targets with a soluble NKp30 fusion protein. In particular, soluble NKp30/VASP A1683F inhibited the cytolytic activity of NK-92 cells against K562 targets. (See FIG. 1A.) In a separate cytolytic assay experiment using different concentrations of soluble NKp30/VASP (0.25, 0.5, 1.0, 2.0, 4.0, 8.0, and 16.0 µg/ml) added to wells containing NK-92 effectors and K562 targets at an effector:target ratio of 9:1, soluble NKp30 inhibited lysis by NK-92 cells in a dose dependent manner. (See FIG. 1B.)
Figure 1B:
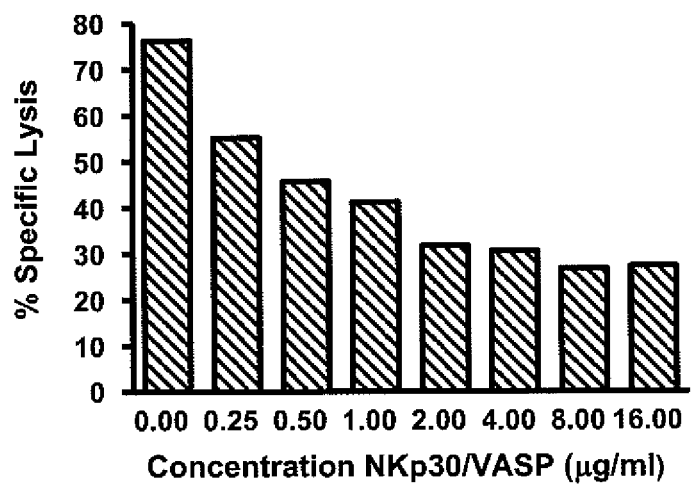

As shown in FIG. 1, soluble NKp30/VASP A1683F inhibited the cytolytic activity of NK-92 cells against K562 targets. (See FIG. 1A.) Other VASP controls had no effect, suggesting that the ability of NK-92 to lyse K562 targets was dependent on NKp30.

In a separate cytolytic assay experiment, soluble NKp30/VASP was added to wells containing NK-92 effectors and K562 targets (effector:target ratio of 9:1) at different concentrations (0.25, 0.5, 1.0, 2.0, 4.0, 8.0, and 16.0 µg/ml). The results of this experiment demonstrated that soluble NKp30 inhibits lysis by NK-92 cells in a dose dependent manner. (See FIG. 1B.) These results suggested the presence of a ligand for NKp30 on K562 cells and encouraged further investigation.

EXAMPLE 2

Soluble NKp30 Specifically Binds K562 Cells

K562 cells were probed by FACS with a soluble form of NKp30 (NKp30/mFc2 (SEQ ID NO:8), containing the extracellular domain of NKp30 and a murine Fc fragment). K562 cells were resuspended in PBS/2% FBS at a concentration of $1.6 \times 10^6$ cells/ml (160,000 cells/sample). 100 µl samples were aliquoted and 1 µl of whole human IgG (Jackson #009-000-003) added to each. NKp30/mFc2 probe was added at a concentration of 2 µg/ml together with 10 µg/ml Heparin and 100-fold mass excess of a VASP protein (NKp30/VASP or a control VASP protein, human zB7R1/VASP (SEQ ID NO:12) or B7-DC/VASP (SEQ ID NO:13)). Cells were incubated for 1 hour on ice and washed with 2 ml cold PBS. Washed cells were resuspended in 100 µl of PBS/2% FBS with 1 µl PE anti-mIgG (Jackson 115-116-071) and incubated for 30 minutes on ice. Cells were then washed twice with 2 ml cold PBS, resuspended in 500 µl of PBS, and analyzed for PE staining on a FACSCalibur.

Figure 2:
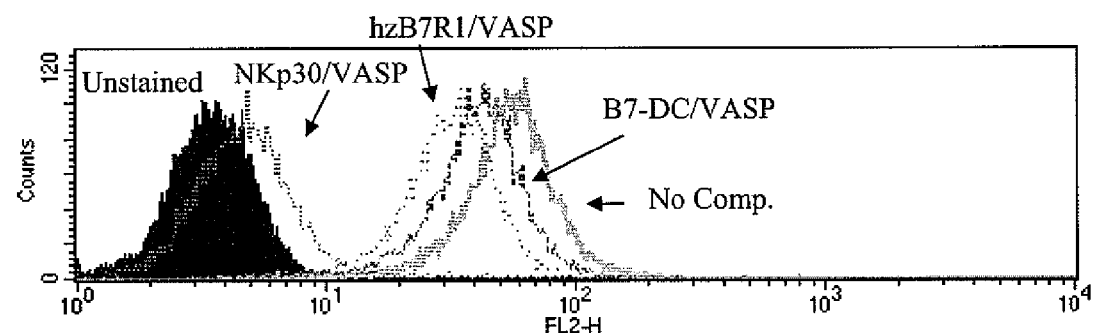
FIG. 2 depicts binding of soluble NKp30 fusion protein to K562 cells. K562 cells were incubated in the presence of NKp30/mFc2 fusion protein followed by secondary labeling with PE anti-mIgG and analyzed for PE staining by FACS. NKp30/mFc2 bound to K562 cells ("No Comp."). This binding was competable with a second soluble NKp30 fusion protein, NKp30/VASP, but not competable with control VASP proteins ("hzB7R1/Vasp" and "B7-DC/Vasp").

As shown in FIG. 2, NKp30/mFc2 bound to K562 cells ("No Comp."). This binding was competable with NKp30/VASP, but not competable with control VASP proteins ("hzB7R1/Vasp" and "B7-DC/Vasp"), demonstrating that the binding of NKp30/mFc2 to K562 cells was specific.

Figure 3A:
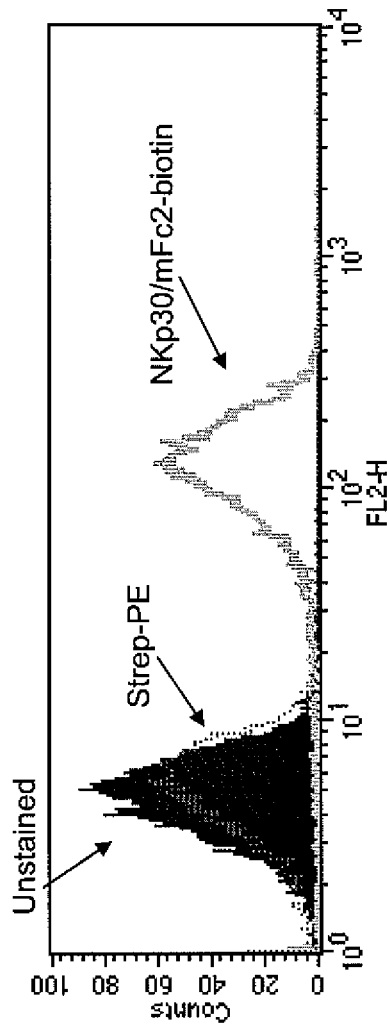
FIG. 3 depicts binding of soluble NKp30 fusion protein to K562 cells, but not to BaF3 cells. K562 cells and BaF3 cells were probed with NKp30/mFc2 conjugated to biotin, followed by secondary labeling with PE-conjugated streptavidin.
Figure 3B:
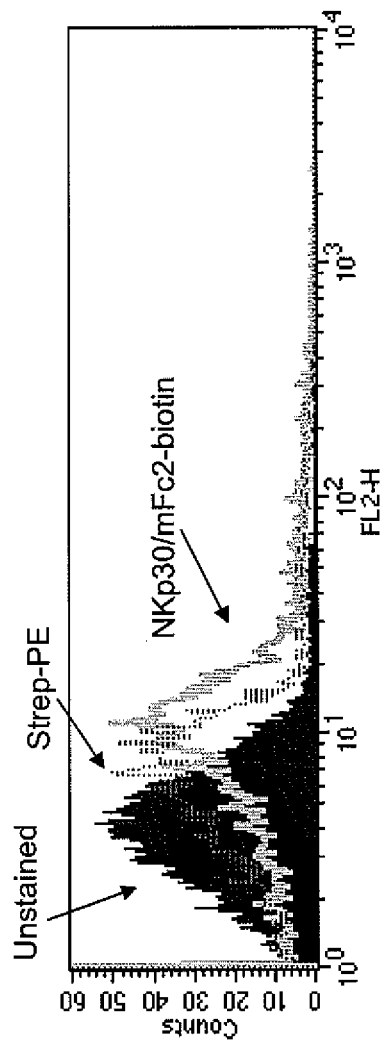

In a separate FACS experiment, K562 cells and BaF3 cells were probed with NKp30/mFc2 conjugated to biotin (NKp30/mFc2-biotin, 4 µg/ml). For these studies, PE-conjugated streptavidin (BD Pharmingen 554061) was used as the secondary reagent. The results of this experiment demonstrated that NKp30/mFc2 bound to K562 cells, but not to BaF3 cells. (See FIG. 3.)

EXAMPLE 3

Crosslinking of K562 Cells and Biotinylated NKp30/mFc2

In an effort to identify an NKp30 ligand on K562 cells, K562 cells were cross-linked with biotinylated NKp30/mFc2, followed by immunoprecipitation and mass spectrometry.

Four samples, the sample of interest and three negative control samples, were analyzed. The sample of interest was K562 cells incubated with biotinylated NKp30/mFc2. The three negative control samples were K562 cells with no NKp30 and BaF3 cells with and without NKp30. $100 \times 10^6$ cells were washed once in PBS and resuspended in 2 ml binding buffer (RPMI, 3 mg/ml BSA, 20 mM HEPES), in the presence or absence of 2 µg/ml NKp30/mFc2-biotin, and incubated for 2 hours on ice. Cells were washed (once in binding buffer, once in PBS), resuspended in 1 ml of crosslinking reagent (3 mm $BS^3$ [Pierce 21580]), and incubated for 30 minutes at room temperature. 7.5 µl of 2 M Tris (pH 7.4) was then added for a final Tris concentration 15 mM, and cells were incubated for 15 minutes at room temperature. Cells were washed twice in PBS and then lysed in 1 ml RIPA/1% TX-100/0.1% SDS for 5 minutes on ice (RIPA buffer: 20 mM Tris pH 7.4, 150 mM NaCl, 2 mM EGTA, 1 mM $NaVO_4$, 1 mM β-glycerophosphate, 1 tablet/25 mls Complete Mini Protease inhibitor cocktail tablet (Roche 10946900)). Lysate supernatants were incubated with 50 µl of streptavidin agarose (Pierce 20347), lysate supernatants for 2 hours at 4° C. with rocking. Streptavidin agarose was washed three times in PBS. Bound protein was eluted by resuspension of strepatividin agarose in 7.5 µl Nupage sample buffer (Invitrogen NP0007), 19.5 µl $H_2O$ and 3 µl reducing agent (Invitrogen NP0004) followed by boiling for 10 minutes. Samples were then split in half and each half run on one of two identical 4-12% NuPage gels (about $40 \times 10^6$ cells/lane). Uncrosslinked NKp30/mFc2-biotin (100 ng, 33 ng, 11 ng, and 3.6 ng) was also run on these gels as a control. One of the two gels was used for tandem mass spectrometry analysis while the other was used for Western blot analysis.

Figure 4:
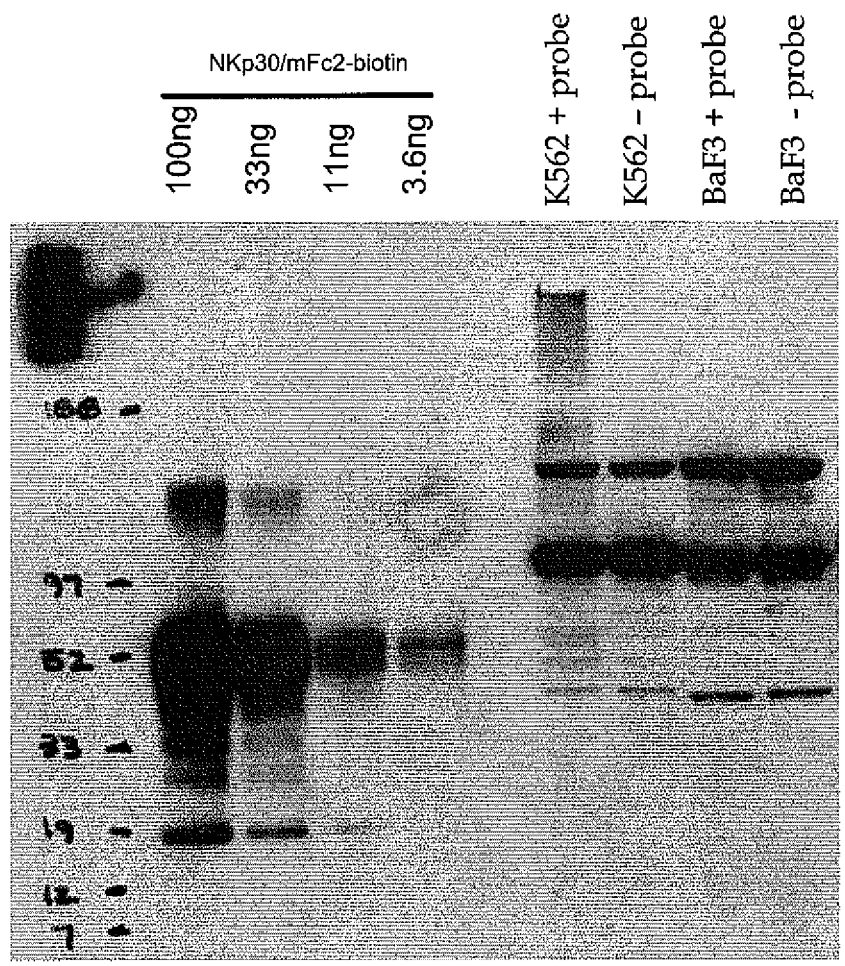
FIGS. 4 and 5A-5B depict crosslinking of K562 cells and biotinylated NKp30/mFc2. Four samples, the sample of interest and three negative control samples, were analyzed. The sample of interest was K562 cells incubated with biotinylated NKp30/mFc2. The three negative control samples were K562 cells with no NKp30 and BaF3 cells with and without NKp30. Each sample was reacted with a chemical crosslinker to covalently link any protein-protein interactions and the biotinylated components were separated and collected by streptavidin agarose precipitation. Samples were split and run on identical 4-12% Nu-Page gels. One gel was used for a Western blot probed with streptavidin-HRP (see FIGS. 4 and 5B). The second gel was coomassie-stained (see FIG. 5A).

For Western blot analysis, proteins were transferred to a nitrocellulose membrane (Invitrogen LC2000) in Western transfer buffer (0.025 M Tris/0.186 M glycine/20% (v/v) methanol) at 600 mAmps constant current for 45 minutes. The nitrocellulose membrane was then blocked with blocking buffer Western A (0.097% Tris Base (w/w)/0.661% Tris HCl (w/w)/0.186% EDTA (w/w)/0.05% Igepal (v/v)/0.877% NaCl (w/w)/0.25% gelatin 1 (w/w)) for 1 hour at room temperature. Blocked membrane was probed with Streptavidin-HRP (1:8000, Pierce 21126) for 1 hour at room temperature and then washed three times with PBS. Washed membrane was incubated in 10 ml ECL A+B buffer (Amersham RPN2209) for 1 min at room temperature, wrapped in Saran® wrap, and exposed to x-ray film. A 5 second exposure gave the result shown in FIG. 4. As shown in FIG. 4, high molecular weight signal is only detected for K562 cells probed with NKp30/mFc2-biotin. Proteins corresponding to this high molecular weight band were excised from the corresponding NuPage gel for tandem mass spectrometry analysis.

EXAMPLE 4

Identification of zB7H6 by LC-MS/MS Proteomic Analysis of NKp30 Interacting Proteins Introduction K562 cells were incubated with biotinylated NKp30/mFc2 and any interactions were preserved by covalently binding the interaction with a chemical crosslinker (see Example 3, supra). Differential mass spectrometry analysis can identify unique proteins by using an automated search algorithm to match tandem mass spectra with peptide sequences. In this analysis, the search algorithm X!Tandem was used to identify proteins unique to the interaction of NKp30/mFc2 with K562 cells.

Materials and Methods

Four samples, the sample of interest and three negative control samples, were analyzed. The sample of interest was K562 cells incubated with biotinylated NKp30/mFc2. The three negative control samples were K562 cells with no NKp30 and BaF3 cells with and without NKp30. Each sample was reacted with a chemical crosslinker to covalently link any protein-protein interactions and the biotinylated components were separated and collected by precipitating with streptavidin agarose.

Figures 5A, 5B:
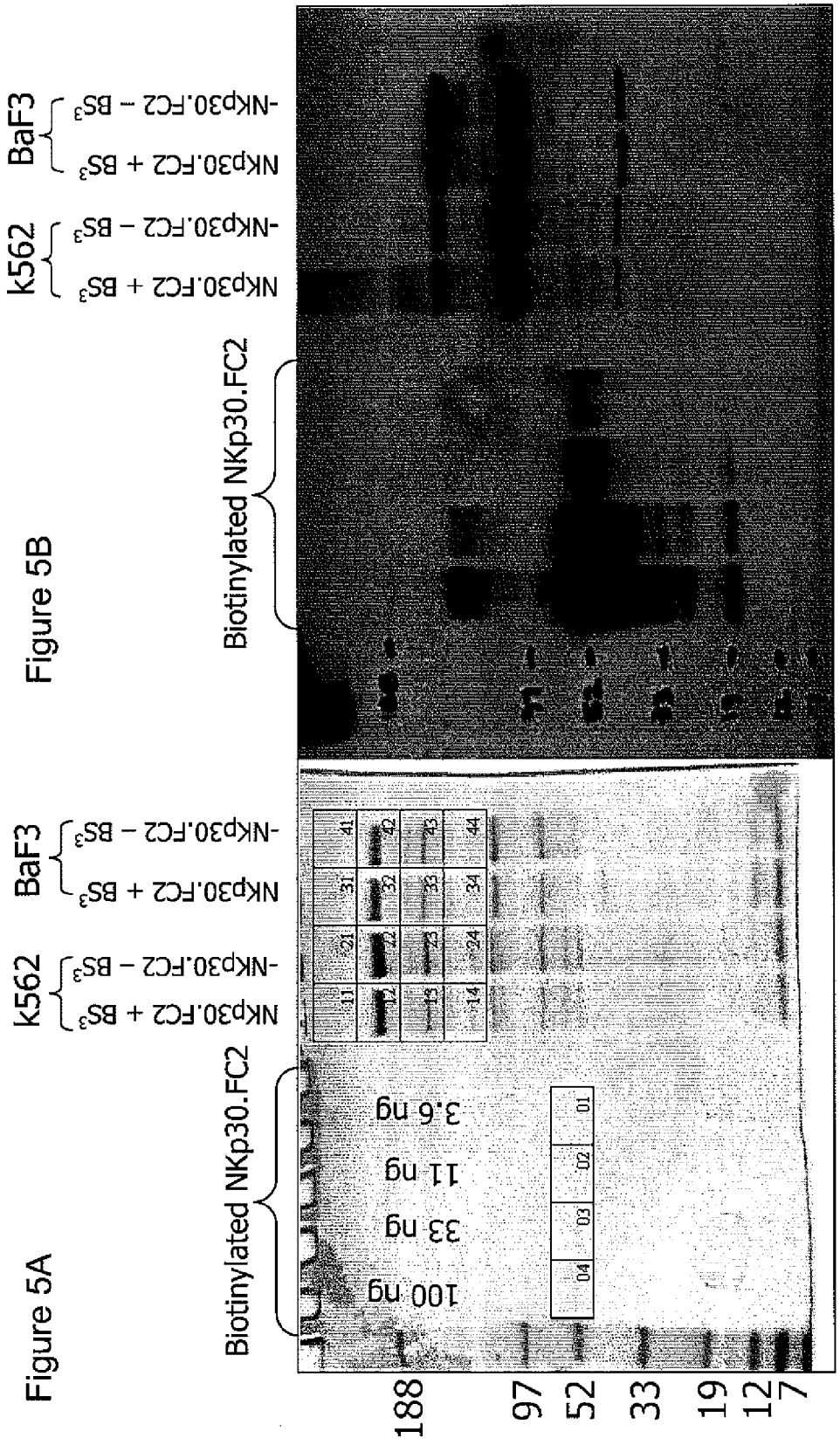

The streptavidin purified fractions containing the biotinylated components were separated by SDS-PAGE electrophoresis. A Western blot was prepared and probed with Strepavidin-HRP (see Example 3, supra). The second gel was coomassie stained. FIGS. 5A and 5B show the coomassie-stained gel and corresponding Western blot juxtaposed.

16 gel bands were excised. These bands corresponded to regions 11-14, 21-24, 31-34, and 41-44 as delineated in FIG. 5A. The proteins in these gel bands were reduced with TCEP (25 µl, 25 mM, 80° C., 15 min), the resulting free cysteines were capped with IAM (25 µl, 100 mM, 25° C., 2 hr) and the sample was digested with trypsin (Promega V5111, lot 18889904, 10 µl, 20 µg/mL, 37° C., 18 hr). The resulting peptides were extracted from the gel pieces, dried down and reconstituted in 20 µL of 0.1% FA. 5 µl of the resulting peptide mixture was separated on Magic C18AQ 3 µm, 200A resin packed into ~10 cm of 50 um fused silica. Eluting peptides were analyzed on an LTQ Ion Trap mass spectrometer. The analysis on the mass spectrometer consisted of a cycle of ten scans. In the first scan, a full MS scan from 400 to 2000 m/z was obtained. Subsequent scans analyzed the nine most intense ions by MS/MS. Dynamic exclusion prevented an analyzed ion from being targeted for MS/MS analysis from 15 seconds to 30 seconds after its initial MS/MS analysis.

The raw data files were converted to text files using Bioworks. The resulting text files were searched against a human ipi database using the automated search algorithm, X!Tandem.

Results and Discussion

As previously noted, the Western blot and coomassie-stained gel are shown in FIGS. 5A and 5B. In the Western blot, unique bands appear in the lane containing the sample of interest that run at a molecular weight greater than the molecular weight of the biotinylated NKp30/mFc2 (~50 kDa). (See FIG. 5B.) This suggests that these bands are biotinylated NKp30 crosslinked to binding partners on the surface of the K562 cells. In the corresponding coomassie-stained gel (see FIG. 5A), band 11 contains the proteins identified in the Western blot as NKp30 conjugated to binding partners on the K562 cell surface. A list of proteins identified from this section of the gel that were not identified in the corresponding negative control bands (21, 31 and 41) can be found in Table 7. Analysis of the genomics database identified one of these proteins as hypothetical protein DKFZp686O24166. The location of the three peptides identified by LC-MS/MS in the amino acid sequence of hypothetical protein DKFZP686I1167 can be found in FIG. 6. All spectra were also manually inspected to confirm the peptide/protein identifications made by X!Tandem.

TABLE 7

Unique proteins identified in gel band 11

| Protein name | Unique peptides ID'ed by LC-MS/MS |
|---|---|
| Natural cytotoxicity triggering receptor 3 | 3 |
| Hypothetical protein DKFZP686I21167 | 3 |
| Plectin 6 | 6 |
| Cation-independent mannose-6-phosphate receptor precursor | 13 |
| NKp30/Fc2 | 8 |

Conclusion

NKp30/mFc2 and hypothetical protein DKFZP686I21167 were identified only in the sample in which NKp30/mFc2 was allowed to interact with K562 cells. These data support hypothetical protein DKFZP686I21167 as a binding partner to NKp30.

EXAMPLE 5

Analysis of zB7H6 Sequence and Gene Structure and Identification of zB7H6 as a B7 Family Member Based on B7 family gene profiling, hypothetical protein DKFZP686I21167 was identified as a member of the B7 family of cellular receptors. The gene structure profile is Signal-2-IgV-2-IgC-2-TMD-0-LgEx. (See FIG. 7.) The extracellular region of this profile matches a B7 gene structure model, with includes characteristic exon patterns in which the first exon encodes a leader sequence, the second exon encodes an IgV domain and the third exon encodes an IgC domain. Another characteristic feature of the B7 family gene structure is the phasing of the exons: in the region corresponding to the extracellular domain, B7 family members show a conserved phasing of 2 between exons 1 to 4. (See id.) Based partly on the identification of DKFZP686I21167 as a B7 family member, this protein was assigned the in-house designation zB7H6. zB7H6's cytoplasmic region is homologous to Gag polyprotein with 44% identity, and it contains potential signaling motifs such as SaYtpL (ITIM), YqlQ (SH2), and PdaPilPvsP (SH3). (See FIG. 7.) Therefore, it may have other functions in addition to triggering pNKp30.

A search of public EST databases identified at least 20 human ESTs corresponding to zB7H6, but no mouse EST or mRNAs. There are only predicted sequences for all the other species (e.g., mouse, rat, dog, cow). There is no similarity within the intracellular region between human and predicted peptides from other species except Apes.

EXAMPLE 6

Human zB7H6 Expression Construct cDNA clone CT#102296, corresponding to DKFZp686O24166 (designated zB7H6), was purchased from the German Cancer Research Center, Heidelberg, Germany.

An expression plasmid containing a polynucleotide encoding the full-length human zB7H6 (SEQ ID NO:2) was constructed via PCR, restriction digestion and ligation. A fragment of human zB7H6 cDNA was isolated by PCR using CT#102296 as template, with flanking regions at the 5' and 3' ends corresponding to the vector sequences flanking the human zB7H6 insertion point using primers zc58067 (SEQ ID NO:9) and zc58401 (SEQ ID NO:10)

The PCR reaction mixture was run on a 1% agarose gel and a band corresponding to the size of the insert is gel-extracted using a QIAquick™ Gel Extraction Kit (Qiagen, Valencia, Calif.). The resulting purified PCR product was digested with EcoRI and XhoI for 2 hours at 37° C. and run on a 1% agarose gel for band purification as described above. Plasmid pZP-7NX was digested with EcoRI and XhoI for 2 hours at 37° C. and run on a 1% agarose gel for band purification as described above. 2 µl of the PCR product and 1 µl of cut pZP-7NX were ligated in a total volume of 20 µl with 2 µl 10× ligation buffer, 14 ul of $H_2O$ and 1 ul of T4 DNA Ligase (Promega, Madison, Wis.) for 2 hours at room temperature. 1 ul of the ligation was electroporated into Electromax DH10B (Invitrogen, Carlsbad, Calif.) using a Gene Pulser II electroporator (BioRad, Hercules, Calif.) set at 25 uF, 300 ohms and 2100 volts. 100 µl of the transformation was plated on one LB AMP plates (LB broth (Lennox), 1.8% Bacto™ Agar (Difco), 100 mg/L Ampicillin).

Individual colonies were grown overnight in a 2 ml LB 100 mg/L Ampicillin growth media and miniprepped using a plasmid mini kit (Qiagen, Valencia, Calif.) The minipreps were digested with BamHI and BglII and clones with the correct 1.152 kB insert were submitted for DNA sequencing. The correct construct was designated as pZP-7NX hzB7H6.

EXAMPLE 7

Expression of Full-Length zB7H6 in P815 and BaF3 Cells: zB7H6 Specifically Binds to NKp30 and is Able to Trigger NK Cell Activity The zB7H6 clone that was verified sequence correct (pZP-7NX hzB7H6) was reintroduced into electromax DH10B by electroporation and then scaled up to a 200 ml LB+amp overnight culture from which DNA was purified using Qiagen kit#12183. 40 µg of DNA was linearized by digestion with HindIII and ethanol precipitated. This DNA was electroporated into P815 and BaF3 cells using the following protocol. P815 cells were washed 2 times with Optimem serum free medium (Invitrogen, Carlsbad, Calif.) and resuspended at $1×10^7$ cells/ml in Optimem. 800 µl of cells were transferred to the tube containing the linearized DNA from above and incubated for 15 minutes at room temperature. The DNA/cell mix was transferred to a 4 mm electroporation cuvette and shocked at 800 µF and 300 volts. After a 1 minute incubation, cells were reshocked at 1180 µF and 300 volts. Cells were incubated overnight at 37° C. before being selected in 1 mg/ml Geneticin (Invitrogen 1013-027) and clones were generated by plating by limiting dilution at 0.3 cells/well. Randomly selected clones were screened by FACS for binding to a soluble form of NKp30 (NKp30/VASP; SEQ ID NO:11). The highest selecting clone was put into a FACS binding competition assay and a cytolytic assay.

A FACS binding competition assay was performed using BaF3 cells resuspended at $3 \times 10^6$/ml and aliquoted at 100 µl/sample for a final count of 300,000 cells/sample. 1 µl of whole mouse IgG (Jackson 015-000-003) was added per sample followed by addition of NKp30/mFc2-A647 labeled probe at 2 µg/ml. In samples to include competition, unlabeled probe was added at 100-fold mass excess and the samples were incubated for 1 hour on ice. Samples were washed one time with cold PBS and samples were analyzed for binding of soluble NKp30/mFc2-A647 on a FACSCalibur.

Figure 8A:
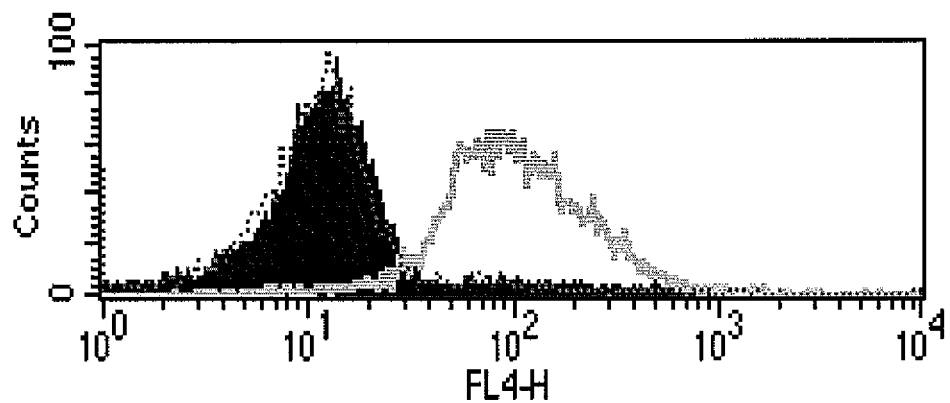
FIG. 8 depicts binding of soluble NKp30 to BaF3 cells expressing full-length zB7H6. Soluble NKp30/VASP-A647 bound to cells electroporated with the human zB7H6 expression vector (see FIGS. 8A and 8B—solid, unfilled line), but not to control cells containing an empty vector control (see FIGS. 8A and 8B—filled line). Staining with NKp30/VASP-A647 was not observed in the presence of a 100-fold excess of unlabeled NKp30VASP (see FIG. 8A—dashed line), but was observed in the presence of a 100-fold excess of unlabeled irrelevant VASP protein (see FIG. 8B—dashed line).
Figure 8B:
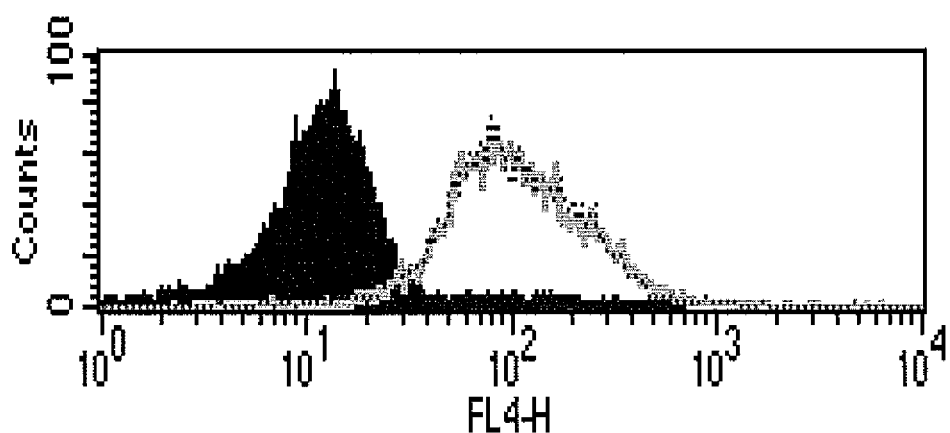
Figure 9:
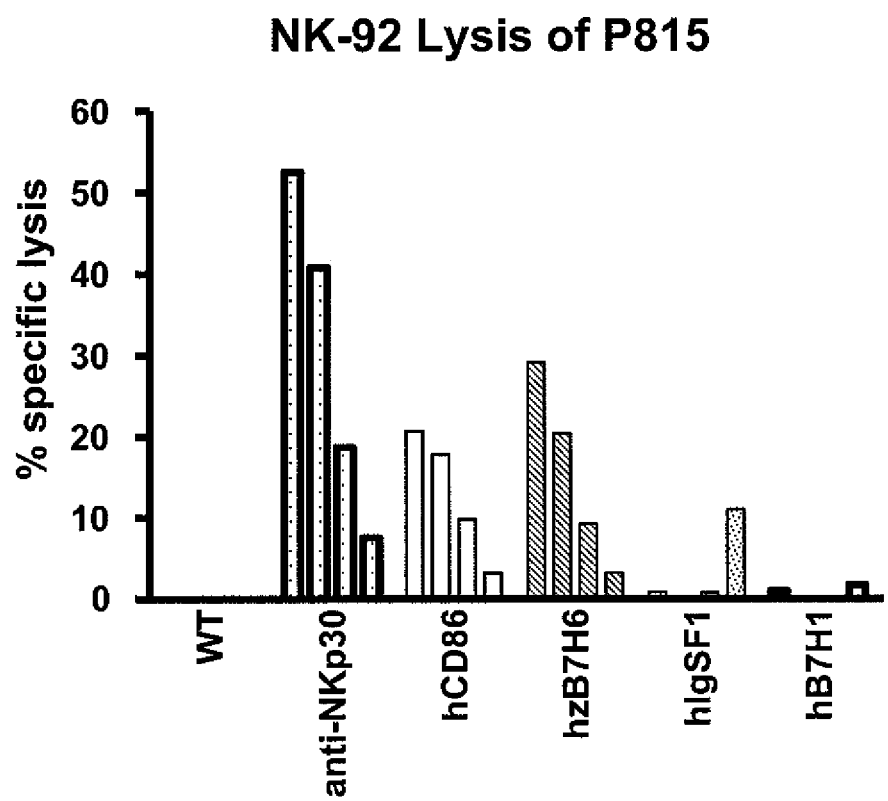
FIG. 9 depicts NK-92 lysis of P815 cells. NK-92 cells were cultured with P815 cells at an effector:target ratio from 27:1 down to 1:1 in 3-fold dilutions. NK-92 cells did not lyse wild-type P815 cells or P815 cells transfected with two non-triggering control proteins (hIgSF1 and hB7H1), while addition of an activating anti-NKp30 monoclonal antibody triggered re-directed lysis. Transfection of either hCD86 or zB7H6 triggered direct killing of P815 cells.

The results of the FACS binding competition assay are shown in FIGS. 8A and 8B. Soluble NKp30/VASP-A647 bound to cells electroporated with the hzB7H6 expression vector, but not to control cells containing an empty vector control. Staining with NKp30/VASP-A647 was not observed in the presence of a 100-fold excess of unlabeled NKp30/VASP (see FIG. 8A), but was observed in the presence of a 100-fold excess of unlabeled irrelevant VASP protein (see FIG. 8B).

A cytolytic assay was performed with NK-92 cells as effectors against P815 targets. NK-92 cells were washed 1× with HBSSF (Hank's buffered saline (Ca, Mg Free)+5% FBS) and resuspended in HBSSF at $1.35 \times 10^6$/ml (to achieve a 27:1 ratio). 150 µl of washed cells were plated in the top row of a U-bottom 96-well plate and serially diluted (1:3) into HBSSF. P815 target cells were washed 1× with HBSSF and labeled at $1 \times 10^6$ cells/ml in 10 µM calcein AM Molecular probes #C1430 (2.5 µl/ml of 4 mM stock in DMSO, 4 mM=4 mg/ml) for 60 minutes at 37° C. Labeled cells were washed 2× in HBSSF and $1 \times 10^6$ cells were resuspended in 20 ml HBSSF (5000 cells/100 µl). 100 µl of suspended target cells were added to diluted effectors for a total volume of 200 µl (effector:target ratios of 27:1, 9:1, 3:1, and 1:1). An activating anti-NKp30 monoclonal antibody was also added to some sets of serially diluted wells at a concentration of 2 µg/ml.

Effector and target cells were spun at 500 rpm for 2 min, incubated at 37° C. for 3 hours, spun at 1500 rpm for 5 min, and then 100 µl supernatant transferred to a new flat bottom 96-well. Flat bottom plates containing transferred supernatants were read on a fluoremeter for 1 second at an excitation wavelength of 485 nm and emission wavelength of 535 nm.

NK-92 cells did not lyse wild-type P815 cells or P815 cells transfected with two non-triggering control proteins (hIgSF1 (SEQ ID NO:14) and hB7H1 (SEQ ID NO:15)), while addition of an activating anti-NKp30 monoclonal antibody triggered re-directed lysis. Transfection of either hCD86 (Azuma et al., Nature 366:76, 1993) or zB7H6 triggered direct killing of P815 cells.

These data demonstrate that zB7H6 specifically binds to NKp30 and is able to trigger cytolytic activity.

EXAMPLE 8

Cloning and Construction of Human zB7H6/mFc2

An expression plasmid containing a polynucleotide encoding the extra-cellular domain of human zB7H6 and the mouse Fc2 portion was constructed via PCR amplification, restriction digestion and ligation. A DNA fragment of the extra-cellular domain of human zB7H6 was isolated by PCR using SEQ CT#102296 as template with flanking regions at the 5' and 3' ends corresponding to the vector sequence and the mouse Fc2 sequence flanking the human zB7H6 insertion point using primers zc50437 (SEQ ID NO:20) and zc50438 (SEQ ID NO:21).

The PCR reaction mixture was run on a 1% agarose gel and a band corresponding to the size of the insert is gel-extracted using a QIAquick™ Gel Extraction Kit (Qiagen, Valencia, Calif.). The initial plasmid used was pZMP21 as a base vector with the mouse Fc2 portion built into it. Plasmid pZMP21 is a mammalian expression vector containing an expression cassette having the MPSV promoter, multiple restriction sites for insertion of coding sequences, a stop codon, an E. coli origin of replication; a mammalian selectable marker expression unit comprising an SV40 promoter, enhancer and origin of replication, a DHFR gene, and the SV40 terminator; and URA3 and CEN-ARS sequences required for selection and replication in S. cerevisiae. It was constructed from pZP9 (deposited at the American Type Culture Collection, 10801 University Boulevard, Manassas, Va. 20110-2209, under Accession No. 98668) with the yeast genetic elements taken from pRS316 (deposited at the American Type Culture Collection, 10801 University Boulevard, Manassas, Va. 20110-2209, under Accession No. 77145), an internal ribosome entry site (IRES) element from poliovirus, and the extracellular domain of CD8 truncated at the C-terminal end of the transmembrane domain. Plasmid hBTLA mFc2 pZMP21 was digested with EcoRl/BglII to cleave off human BTLA and used for ligation with the PCR insert.

2 µl of the cut PCR product and 1 µl of cut pZMP21 were ligated in a total volume of 20 ul with 2 ul 10× ligation buffer, 14 ul of H$_2$O and 1 ul of T4 DNA Ligase (Promega, Madison, Wis.) for 2 hours at room temperature. 1 ul of the ligation was electroporated into Electromax DH10B (Invitrogen, Carlsbad Calif.) using a Gene Pulser II electroporator (BioRad, Hercules, Calif.) set at 25 uF, 300 ohms and 2100 volts. 100 µl of the transformation was plated on one LB AMP plate (LB broth (Lennox), 1.8% Bacto™ Agar (Difco), 100 mg/L Ampicillin). The colonies were screened by restriction digestion with EcoRI and KpnI, with clones showing the expected 1.596 kB insert being submitted for DNA sequencing. A sequence correct construct was designated as hB7H6mFc2pZMP21. The DNA sequence coding for hzB7H6/mFc2 is shown as SEQ ID NO:16; the amino acid sequence for hzB7H6/mFc2 is shown as SEQ ID NO:17.

EXAMPLE 9

Cloning and Construction of zB7H6/VASP

Human vasodialator-activated phosphoprotein (VASP) is described by Kühnel, et al. (Proc. Nat'l. Acad. Sci. USA 101: 17027, 2004). VASP nucleotide and amino acid sequences are provided as SEQ ID NOs: 3 and 4. Two overlapping oligonucleotides, which encoded both sense and antisense strands of the tetramerization domain of human VASP protein, were synthesized by solid phased synthesis using oligonucleotide zc50629 (SEQ ID NO:22) and oligonucleotide ZC 50630 (SEQ ID NO:23). These oligonucleotides were annealed at 55° C., and amplified by PCR with the olignucleotide primers zc50955 (SEQ ID NO:24) and zc50956 (SEQ ID NO:25).

The amplified DNA was fractionated on 1.5% agarose gel and then isolated using a Qiagen gel isolation kit according to manufacturer's protocol (Qiagen, Valiencia, Calif.). The isolated DNA was inserted into BglII cleaved pzmp21 vector by yeast recombination. DNA sequencing confirmed the expected sequence of the vector, which was designated pzmp21VASP-His$_6$.

The extracellular domain of human zB7H6 was generated by PCR amplification from CT#102296 with oligos zc58284 (SEQ ID NO:26) and zc58419 (SEQ ID NO:27). The PCR reaction mixture was run on a 1% agarose gel and a band corresponding to the size of the insert is gel-extracted using a QIAquick™ Gel Extraction Kit (Qiagen, Valencia, Calif.). The resulting purified PCR product was digested with EcoRI and BglII for 2 hours at 37° C. and run on a 1% agarose gel for band purification as described above. The isolated fragment was inserted into EcoRI/BglII cleaved pZMP21VASP-His$_6$ vector by ligation. 2 µl of the PCR product and 1 µl of cut pZMP21VASP-His$_6$ were ligated in a total volume of 20 µl with 2 µl 10× ligation buffer, 14 µl of H$_2$O and 1 µl of T4 DNA Ligase (Promega, Madison, Wis.) for 2 hours at room temperature. 1 µl of the ligation was electroporated into Electromax DH10B (Invitrogen, Carlsbad, Calif.) using a Gene Pulser II electroporator (BioRad, Hercules, Calif.) set at 25 µF, 300 ohms and 2100 volts. 100 µl of the transformation was plated on one LB AMP plates (LB broth (Lennox), 1.8% Bacto™ Agar (Difco), 100 mg/L Ampicillin).

Individual colonies were grown overnight in a 2 ml LB AMP growth media and miniprepped using a plasmid mini kit (Qiagen, Valencia, Calif.) The minipreps were digested with BamHI and BglII and clones with the correct 1.152 kB insert were submitted for DNA sequencing. The correct construct was designated as pZMP21 hzB7H6 VASP-His$_6$. The DNA sequence coding for hzB7H6/VASP-His$_6$ is shown as SEQ ID NO:18; the amino acid sequence for hzB7H6/VASP-His$_6$ is shown as SEQ ID NO:19.

EXAMPLE 10

Stable Transfection and Expression of zB7H6/mFc2 in CHO Cells

Three sets of 50 µg of the hB7H6mFc2pZMP21 construct were each digested with 25 units of Pvu I at 37° C. for three hours and then were precipitated with IPA and spun down in a 1.5 mL microfuge tube. The supernatant was decanted off the pellet, and the pellet was washed with 0.5 mL of 70% ethanol. The tube was spun in a microfuge for 15 minutes at 13,000 RPM and the supernatant was decanted off the pellet. The pellet was then resuspended in 1 ml of ZF1 media in a sterile environment, allowed to incubate at 60° C. for 15 minutes, and was allowed to cool to room temperature. 5E6 5×SA APFDXB11 CHO cells were spun down in each of three tubes and were resuspended using the DNA-media solution. The DNA/cell mixtures were placed in a 4 mm gap cuvette and electroporated using the following parameters: 950 µF, high capacitance, and 300 V. The contents of the cuvettes were then removed, pooled, and diluted to 25 mLs with ZF1 media and placed in a 125 mL shake flask. The flask was placed in an incubator on a shaker at 37° C., 6% CO$_2$, and shaking at 120 RPM.

The cell line was subjected to nutrient selection followed by step amplification to 200 nM methotrexate (MTX), and then to 500 nM MTX. Expression was confirmed by Western blot probed with anti-mouse IgG2a antibody and anti-mouse IgG H+L antibody, and the cell line was scaled-up and protein purification followed.

EXAMPLE 11

Stable Transfection and Expression of zB7H6/VASP in CHO Cells

Three sets of 50 µg of the pZMP21 hzB7H6 VASP-His$_6$ construct were each digested with 25 units of Pvu I at 37° C. for three hours and then were precipitated with IPA and spun down in a 1.5 mL microfuge tube. The supernatant was decanted off the pellet, and the pellet was washed with 0.5 mL of 70% ethanol. The tube was spun in a microfuge for 15 minutes at 13,000 RPM and the supernatant was decanted off the pellet. The pellet was then resuspended in 1 ml of ZF1 media in a sterile environment, allowed to incubate at 60° C. for 15 minutes, and was allowed to cool to room temperature. 5E6 5×SA APFDXB11 CHO cells were spun down in each of three tubes and were resuspended using the DNA-media solution. The DNA/cell mixtures were placed in a 4 mm gap cuvette and electroporated using the following parameters: 950 µF, high capacitance, and 300 V. The contents of the cuvettes were then removed, pooled, and diluted to 25 mLs with ZF1 media and placed in a 125 mL shake flask. The flask was placed in an incubator on a shaker at 37° C., 6% CO2, and shaking at 120 RPM.

The cell line was subjected to nutrient selection followed by step amplification to 200 nM methotrexate (MTX), and then to 500 nM MTX. Expression was confirmed by Western blot probed with anti-6-His antibody, and the cell line was scaled-up and protein purification followed.

EXAMPLE 12 zB7H6 Triggers Cytolytic Activity in Human Primary NK Cells

A cytolytic assay was performed with human primary NK cells as effectors against P815 targets. NK cells were purified from human peripheral blood using negative selection with magnetic bead labeling Miltenyi #130-092-657. These purified NK cells were cultured overnight in RPMI/10% FBS supplemented with 10 ng/ml of human IL-2 (R&D #202-IL-010). The NK cells were then washed 1× with HBSSF (Hank's buffered saline (Ca, Mg Free)+5% FBS) and resuspended in HBSSF at 1.35×10$^6$/ml (to achieve a 27:1 ratio). 150 µl of washed cells were plated in the top row of a U-bottom 96-well plate and serially diluted (1:3) into HBSSF. P815 target cells were washed 1× with HBSSF and labeled at 1×10$^6$ cells/ml in 10 µM calcein AM Molecular probes #C1430 (2.5 µl/ml of 4 mM stock in DMSO, 4 mM=4 mg/ml) for 60 minutes at 37° C. Labeled cells were washed 2× in HBSSF and 1×10$^6$ cells were resuspended in 20 ml HBSSF (5000 cells/100 µl). 100 µl of suspended target cells were added to diluted effectors for a total volume of 200 µl (effector:target ratios of 27:1, 9:1, 3:1, and 1:1). An activating anti-NKp30 monoclonal antibody was also added to some sets of serially diluted wells at a concentration of 2 µg/ml. A soluble mFc version of NKp30 was added at 2 µg/ml to some sets of serially diluted wells and an unrelated protein, HHLA2/mFc2 was added to a different set at the same concentration.

Effector and target cells were spun at 500 rpm for 2 min, incubated at 37° C. for 3 hours, spun at 1500 rpm for 5 min, and then 100 µl of supernatant was transferred to a new flat bottom 96-well. Flat bottom plates containing transferred supernatants were read on a fluorometer for 1 second at an excitation wavelength of 485 nm and emission wavelength of 535 nm.

NK cells lysed wild-type P815 cells at low levels but P815 cells transfected with zB7H6 were lysed at levels approximating re-directed killing triggered by an activating anti-NKp30 monoclonal antibody. Soluble NKp30 inhibited lysis of zB7H6 transfected P815 to approximately background levels, but addition of HHLA2/mFc2 had no effect.

EXAMPLE 13

Generation of Mouse Anti-zB7H6 Polyclonal Antibody

Immunizations

Five 3 month old female BALB/c mice (Charles River Laboratories, Wilmington, Mass.) were immunized with human zB7H6. The mice were initially immunized by subcutaneous injection with ~50 µg of purified, recombinant human zB7H6 (ZGI produced in CHO DXB 11 5SA, Lot # A1980F) fused with VASP, 6His, and BSA conjugated (SJAS 9 Aug. 2007) in combination with Emulsigen®-P adjuvant (MVP Laboratories INC, Omaha, Nebr.) as per manufacturer's instructions. Following the initial immunization each of the mice received an additional 50 µg of human zB7H6 in Emulsigen®-P adjuvant via the subcutaneous route every two weeks over a nine week period. Seven days after the third and fourth immunizations the mice were bled via the retro orbital plexus and the serum was separated from the blood for analysis of its ability to bind to human zB7H6.

Direct Assay

The ability of anti-human zB7H6 antibodies in the antisera to bind to human zB7H6 (lot# A1980F) was assessed using a direct style ELISA assay. In this assay, wells of 96-well polystyrene ELISA plates were first coated with 100 µL/well of human zB7H6 (lot # A1980F) at a concentration of 1 µg/mL in Coating Buffer (0.1M Na2CO3, pH 9.6). Plates were incubated overnight at 4° C. after which unbound receptor was aspirated and the plates washed twice with 300 µL/well of Wash Buffer (PBS-Tween defined as 0.137M NaCl, 0.0022M KCl, 0.0067M Na2HPO4, 0.0020M KH2PO4, 0.05% v/w polysorbate 20, pH 7.2). Wells were blocked with 200 µL/well of Blocking Buffer (PBS-Tween plus 1% w/v bovine serum albumin (BSA)) for 1 hour, after which the plates were washed twice with Wash Buffer. Serial 10-fold dilutions (in 1% BSA in PBS-Tween) of the sera were prepared beginning with an initial dilution of 1:100 and ranged to 1:100,000. Normal mouse sera served as a control. Duplicate samples of each dilution were then transferred to the assay plate, 100 µL/well in order to bind human zB7H6. Following a 1 hour incubation at room temperature, the wells were aspirated and the plates washed twice as described above. Horseradish peroxidase labeled Goat anti Mouse Kappa antibody (SouthernBiotech, Birmingham, Ala.) at a dilution of 1:5,000 was then added to each well, 100 µL/well, and the plates incubated at RT for 1 hour. After removal of unbound HRP conjugated antibody, the plates were washed twice, 100 µL/well of tetra methyl benzidine (TMB) (BioFX Laboratories, Owings Mills, Md.) added to each well and the plates incubated for 2.5 minutes at RT. Color development was stopped by the addition of 100 µL/well of TMB Stop Reagent (BioFX Laboratories, Owings Mills, Md.) and the absorbance values of the wells read on a Molecular Devices Spectra MAX 340 instrument at 450 nm.

Immune sera from all mice showed a strong anti-VASP and anti-zB7H6 response. Sera was pooled and anti-zB7H6 antibody was purified as described below.

Purification of zB7H6 Polyclonal Antibodies

Serum from mice challenged with zB7H6C(VASP)H6 was pooled, diluted 1:1 (v/v) with 35 mM NaPO4, 120 mM NaCl, pH 7.2 and 0.2 µm sterile filtered prior to loading (via batch method) onto CNBr-activated Sepharose™ 4B (GE Healthcare, Piscataway, N.J.) coupled with zB7H6 (mFc2). Prior to loading the diluted serum, the CNBr-activated Sepharose™ 4B resin was pre-equilibrated with, 20 column volumes (approximately 50 ml) of 35 mM NaPO4, 120 mM NaCl, pH 7.2 The ratio of diluted serum to coupled resin was 2.8:1 (v/v).

The chromatography process was performed at both 5° C. and ambient room temperature. Specifically, the loading (capture step) of the diluted serum onto the zB7H6 (mFc2) coupled CNBr-activated Sepharose™ 4B resin was performed using a rocking platform at 5° C. The wash step and subsequent elution step were performed at ambient room temperature (approximately 22° C.) after the serum/resin slurry was poured into an empty glass Econo-Column (Bio-Rad, Hercules, Calif.). The column was washed (via gravity flow) with 15 column volumes (approximately 37.5 ml) of 35 mM NaPO4, 120 mM NaCl, pH 7.2. Bound antibody was then pH eluted (via gravity flow) with 100 mM glycine, pH 2.7. 0.5 ml fractions were collected and immediately neutralized with 0.05 ml 2.0M Tris-HCl, pH 8.0. Fractions were collected and pooled based on A280 readings from a Nanoprop (Thermo Scientific, Fremont, Calif.). The retained flow-through was then reapplied to the zB7H6 (mFc2) coupled CNBr-activated Sepharose™ 4B resin after column regeneration/equilibration. This batch/elute cycle was repeated two times.

The pooled fractions of the corresponding purifications were pooled and then desalted (buffer-exchanged) against 35 mM NaPO4, 120 mM NaCl, pH 7.2 using pre-packed Sephadex™ G-25 Superfine columns, HiTrap™ columns (GE Healthcare, Piscataway, N.J.). 0.5 ml fractions were collected. The pooling of these fractions was determined by the A280 reading on the AKTA Explorer. Pooled, desalted, fractions were then 0.22 µm sterile filtered prior to aliquoting and storage at −80° C.

EXAMPLE 14

Validation of Mouse Anti-zB7H6 Polyclonal Antibody Activity and Specificity

Mouse anti-zB7H6 affinity purified polyclonal antibody was conjugated with Alexa-647 fluorescent marker using an Alexafluor-A647 antibody labeling kit (Invitrogen A30009) following the manufacturer's instructions. 150,000 cells/sample wild-type or zB7H6-transfected P815 cells were probed with anti-zB7H6-A647 at 1 µg/ml with or without unlabeled competitors at 100-fold mass excess. Cells were incubated for 1 hour on ice, washed once with 2 ml of ice cold PBS and then read by flow cytometry on a FACSCalibur instrument. Binding was recorded as mean fluorescent intensity (MFI). Results of this study showed that anti-zB7H6-A647 antibody bound to zB7H6-transfected P815 cells (MFI 600), but not to wild-type (untransfected) P815 cells (MFI≈25). This binding was competable with a 100-fold mass excess of unlabeled anti-zB7H6 (MFI≈40), but not with a 100-fold mass excess of an isotype control antibody (MFI≈500).

Mouse anti-zB7H6 polyclonal antibody was also used in a competition binding assay of NKp30/mFc2-biotin binding to P815 transfectants. 150,000 wild-type or zB7H6-transfected P815 cells were probed with NKp30/mFc2-biotin at 1 µg/ml in 100 µl PBS/2% FBS. Unlabeled anti-zB7H6 polyclonal antibody or other control antibodies or soluble receptors were added at 100-fold mass excess. Cells were stained for 1 hour on ice, washed once with 2 ml of ice cold PBS, and then stained with streptavidin-PE at 1 µg/ml (BD:554061) for 15 min. on ice. Cells were again washed with cold PBS before being read by flow cytometry on a FACSCalibur instrument. Binding was recorded as mean fluorescent intensity (MFI). Results of this study showed that NKp30/mFc2-biotin bound to zB7H6-transfected cells (MFI≈825), but not to wild-type P815 cells (MFI<15). Binding of labeled NKp30/mFc2 was competable by both unlabeled anti-zB7H6 antibody and NKp30/mFc2 (MFI≈25), but not with an isotype control antibody (MFI≈775).

EXAMPLE 15

Inhibition of NK-92 Cytolytic Activity Against K562 and P815 zB7H6 Targets with Soluble Proteins A cytolytic assay was performed with NK-92 cells as effectors against K562 and P815 zB7H6 targets.

NK-92 cells were washed 1× with HBSSF (Hank's buffered saline (Ca, Mg Free)+5% FBS) and resuspended in HBSSF at $1.35 \times 10^6$/ml (to achieve a 27:1 ratio). 150 µl of washed cells were plated in the top row of a U-bottom 96-well plate and serially diluted (1:3) into HBSSF.

K562 and P815 zB7H6 target cells were washed 1× with HBSSF and labeled at $1 \times 10^6$ cells/ml in 10 µM calcein AM Molecular probes #C1430 (2.5 µl/ml of 4 mM stock in DMSO, 4 mM=4 mg/ml) for 60 minutes at 37° C. Labeled cells were washed 2× in HBSSF and $1 \times 10^6$ cells were resuspended in 20 ml HBSSF (5000 cells/100 µl). 100 µl of suspended target cells were added to diluted effectors for a total volume of 200 µl. A soluble form of NKp30 (NKp30VASP tetrameric receptor), a VASP control (B7H3/VASP; SEQ ID NO:[28]), an anti-zB7H6 polyclonal antibody (E10607), or an irrelevant control antibody was also added to some sets of serially diluted wells at a concentration of 5 µg/ml.

Effector and target cells were spun at 500 rpm for 2 minutes, incubated at 37° C. for 3 hours, spun at 1500 rpm for 5 minutes, and then 100 µl supernatant transferred to a new flat bottom 96-well. Flat bottom plates containing transferred supernatants were read on a fluorometer for 1 second at an excitation wavelength of 485 nm and emission wavelength of 535 nm.

Figure 10:
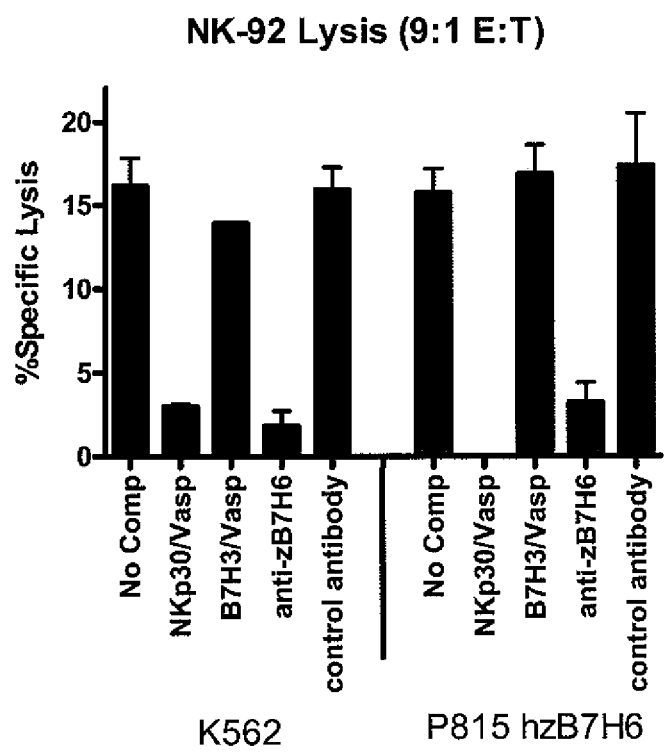
FIG. 10 depicts inhibition of NK-92 cytolytic activity against zB7H6 expressing cells with soluble NKp30 and anti-zB7H6 antibody. NK-92 cells were cultured with either K562 cells or P815 cells expressing zB7H6 at an effector:target ratio of 9 to 1. A soluble form of NKp30 (NKp30/VASP), a control VASP protein (B7H3/VASP), an anti-zB7H6 polyclonal antibody, and an irrelevant control antibody were added to some wells. Soluble NKp30/VASP and anti-zB7H6 polyclonal antibody inhibited the cytolytic activity of NK-92 cells against K562 and P815 zB7H6 targets, while the VASP and antibody controls had no effect.

As shown in FIG. 10, soluble NKp30/VASP and anti-zB7H6 polyclonal antibody inhibited the cytolytic activity of NK-92 cells against K562 and P815 zB7H6 targets at a 9:1 effector to target ratio. (See FIG. 10.) Inhibition was also seen at target to effector ratios of 27:1 and 3:1. VASP and irrelevant antibody controls had no effect. These data suggest that the ability of NK-92 to lyse K562 and P815 zB7H6 targets is NKp30-mediated and is further dependent on zB7H6.

EXAMPLE 16

Soluble NKp30 Specifically Binds K562, P815 zB7H6 and 293F Cells

K562, P815 zB7H6 and 293F cells were probed by FACS with a biotinylated soluble form of NKp30 (Kp30/mFc2), containing the extracellular domain of NKp30 and a murine Fc fragment. Cells were resuspended in PBS/2% FBS at a concentration of $1.5 \times 10^6$ cells/ml (150,000 cells/sample). 100 µl samples were aliquoted with 100 µg/ml of whole human IgG (Jackson #009-000-003) included for Fc receptor blocking. NKp30/mFc2-biotin probe was added at a concentration of 2 µg/ml and 100-fold mass excess of a VASP protein (NKp30VASP or human zB7H6/VASP) or a control VASP protein (B7H3/VASP). Cells were incubated for 1 hour on ice and washed with 2 ml cold PBS. Washed cells were resuspended in 100 µl of PBS/2% FBS with streptavidin-PE (BD: 554061) at 1 µg/ml and incubated for 15 minutes on ice. Cells were then washed with 1 ml cold PBS, resuspended in 250 µl of PBS, and analyzed for PE staining on a FACSCalibur.

Figure 11A:
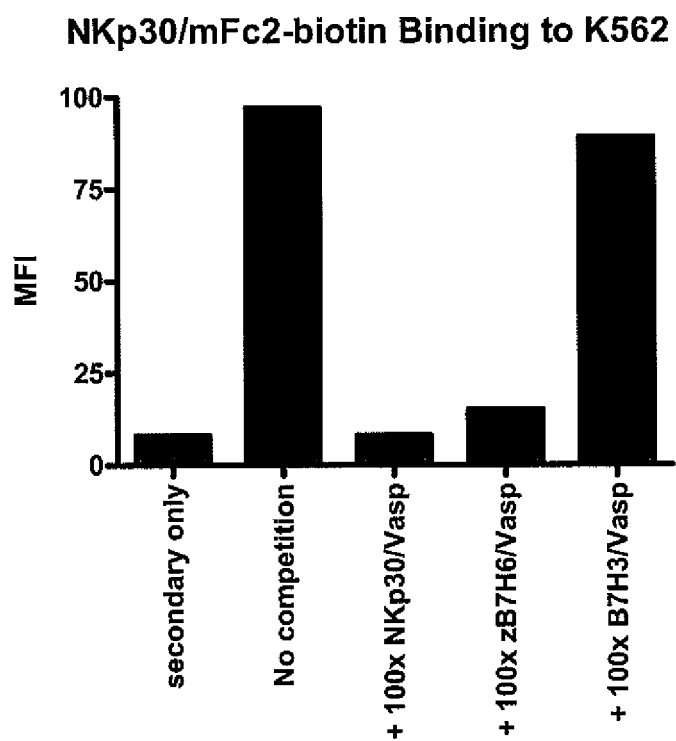
FIGS. 11A-11C depict specific binding of soluble NKp30 to K562, P815 zB7H6 and 293F cells. K562, P815 zB7H6 and 293F cells were probed by FACS with a biotinylated NKp30/mFc2, either in the absence or presence of a 100-fold mass excess of NKp30VASP, zB7H6/VASP, or a control VASP protein (B7H3/VASP). Following incubation with biotinylated NKp30/mFc2, cells were washed and stained with streptavidin-PE. Cells were then washed and analyzed for PE staining on a FACSCalibur. NKp30/mFc2-biotin bound to K562 (11A), 293F (11B), and P815 zB7H6 (11C) cells ("No Competition"). This binding was competable with NKp30/VASP and zB7H6/VASP, but not with control VASP protein ("B7H3/VASP").
Figure 11B:
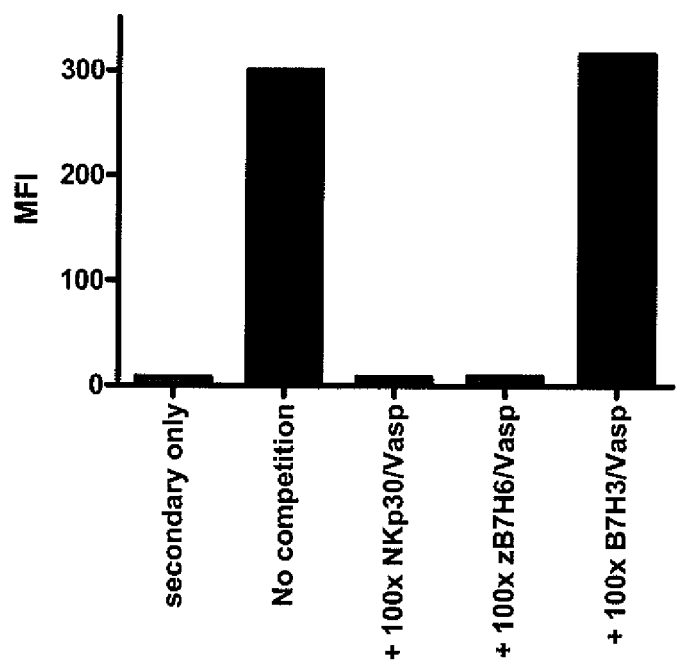
Figure 11C:
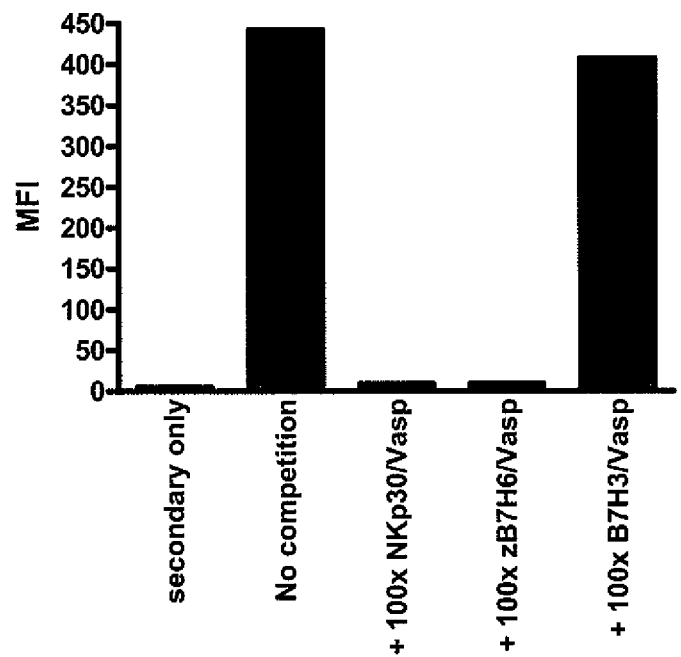
Figure 12A:
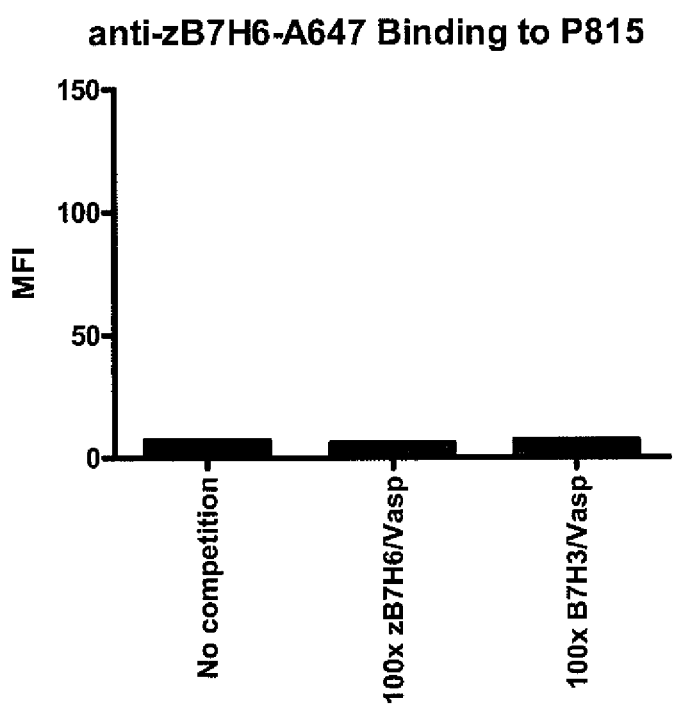
FIGS. 12A-12D depict specific binding of anti-B7H6 antibody to K562, P815 zB7H6, and 293F cells. K562, P815, P815 zB7H6 and 293F cells were probed with an A647 conjugated form of anti-zB7H6 mouse polyclonal antibody (E10607). Cells were incubated with whole human IgG to block Fc receptors, and A647-conjugated anti-zB7H6 ("anti-zB7H6-A647") antibody was added to cells in the absence or presence of a 100-fold mass excess of a VASP protein (zB7H6/VASP or a control VASP protein, B7H3/VASP). Following incubation with antibody, cells were washed and analyzed for APC staining on a FACSCalibur. Anti-zB7H6 bound to K562 (12B), P815 zB7H6 (12C), and 293F (12D) cells but not to untransfected P815 cells (12A) ("No Competition"). This binding was competable with zB7H6/VASP, but not with control VASP protein.
Figure 12B:
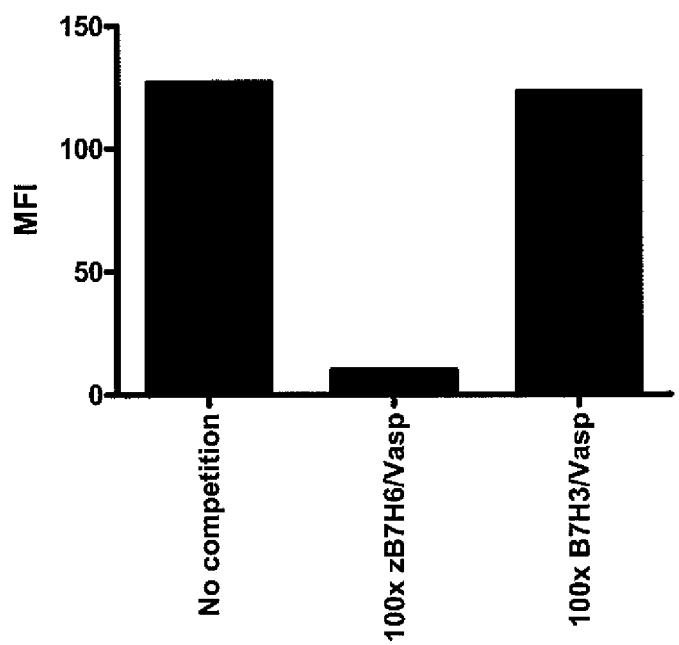
Figure 12C:
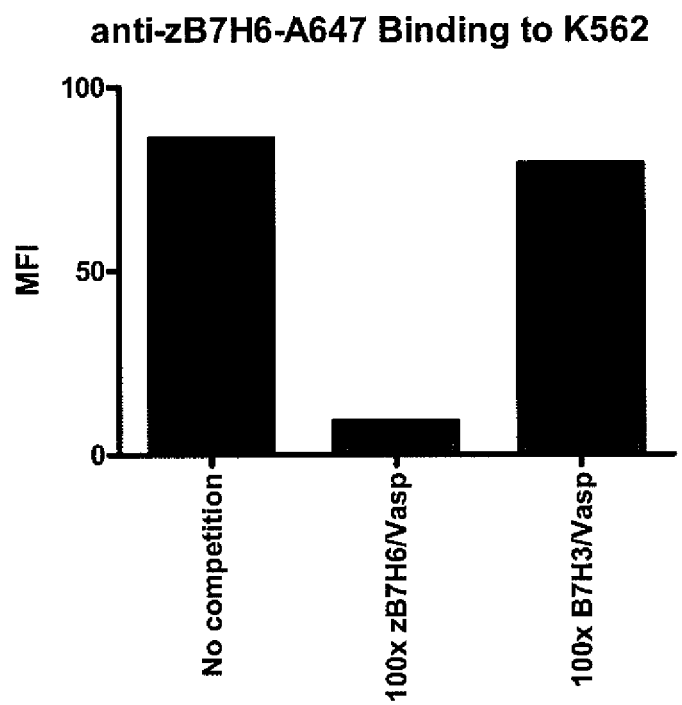
Figure 12D:
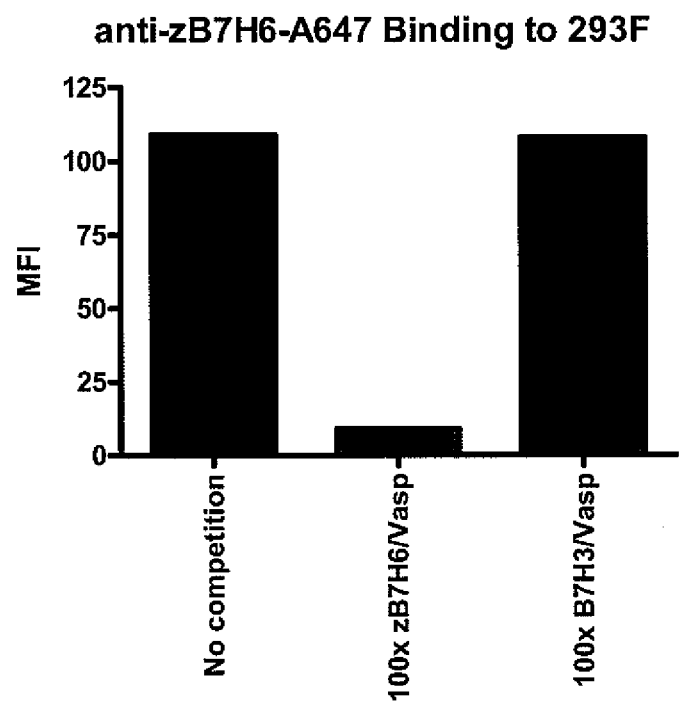

As shown in FIG. 11, NKp30/mFc2-biotin bound to K562, 293F and P815 zB7H6 cells ("No Competition"). This binding was competable with NKp30/VASP and zB7H6/VASP, but not with control VASP protein (B7H3/VASP) demonstrating that the binding of NKp30/mFc2 to K562, P815 zB7H6 and 293F cells was specific. Little or no binding was observed for MCF-7, Aspc-1, A549, and HL-60 tumor cell lines.

EXAMPLE 17

Anti-zB7H6 Specifically Binds K562, P815 zB7H6 and 293F Cells

K562, P815, P815 zB7H6 and 293F cells were probed with an A647 conjugated form of anti-zB7H6 mouse polyclonal antibody (E10607). Cells were resuspended in PBS/2% FBS at a concentration of $1.5 \times 10^6$ cells/ml (150,000 cells/sample). 100 µl samples were aliquoted with 100 µg/ml of whole human IgG (Jackson #009-000-003) included to block Fc receptors. Anti-zB7H6-A647 antibody was added at a concentration of 2 µg/ml and 100-fold mass excess of a VASP protein (zB7H6/VASP or a control VASP protein (B7H3/VASP)). Cells were incubated for 1 hour on ice and washed with 2 ml cold PBS. Cells were then resuspended in 250 µl of PBS and analyzed for APC staining on a FACSCalibur.

As shown in FIG. 12, anti-zB7H6 bound to K562, P815 zB7H6 and 293F cells but not to untransfected P815 cells ("No Competition"). This binding was competable with zB7H6/VASP, but not with control VASP protein (B7H3/VASP), demonstrating that the binding of anti-zB7H6-A647 to K562, P815 zB7H6 and 293F cells was specific. Little or no binding was observed for MCF-7, Aspc-1, A549, and HL-60 tumor cell lines. These data, taken together with the NKp30/mFc2-biotin binding data, show the correspondence of NKp30/mFc-biotin binding with zB7H6 expression.

EXAMPLE 18

Quantitative Real Time PCR Analysis of Normal Human Tissues

Quantitative real-time polymerase chain reaction (qRT-PCR) was used to assay zB7H6 mRNA message levels in normal human tissues. zB7H6 primer and probe were purchased from ABI using their proprietary software that generates primers with FAM reporter dye designed to span exon/intron boundaries to avoid amplification from genomic DNA. This primer (ABI:Hs02340611_m1) was used in a validation experiment in combination with a primer for the housekeeping gene HPRT1 (ABI:4333768-0712016) on 293F cDNA in a 5 log dilution series starting at 100 ng. A plot of the Log of 293F cDNA concentration versus delta cycle threshold (deltaCt) gave a statistically fitted line with the formula Y=−0.02571x+3.504 indicating that the efficiencies of zB7H6 primer and probe set matched that of HPRT1 making $Log_2$ Ct calculations valid (a passing validation experiment is defined as the absolute value of the slope of deltaCt vs. log input cDNA <0.1). A no reverse transcriptase (−RT) control was performed for each of the concentrations in the 293F dilution series to verify the absence of amplification from genomic DNA. A Normal tissue qPCR array was purchased from Origene (Origene HMRT102). 1st strand cDNAs from poly-A RNA in this array were normalized for GAPDH by the manufacturer. Lyophilized samples were resuspended in 30 µl $DiH_2O$ and 13.5 µl was split into each of two reactions, one for HPRT1 and one for zB7H6 RT-PCR. Primers were used at 900 nM and probe at 250 nM in 10 µl reactions run in triplicate on an ABI 7900HT RT-PCR instrument. No amplification with the zB7H6 primers in any of the 48 normal tissues samples was observed despite amplification of the HPRT1 housekeeping gene amplifying in all samples. Additionally, a 293F positive control cDNA gave zB7H6 amplification, indicating that the qRT-PCR reaction was working properly.

EXAMPLE 19

Quantitative Real-Time PCR Analysis of Tumor Cell Lines qRT-PCR was also used to evaluate zB7H6 mRNA from a panel of tumor cell lines of various origin. Total RNA was generated from cells using RNeasy Midi columns (Qiagen 75142) following the manufacturer's instructions. First strand cDNA was synthesized by reverse transcription of 1 µg of RNA using Invitrogen Superscript III Kit (Invitrogen 11752-250) following the manufacturer's instructions. The same primer and probe sets as described in Example 18, supra, were used to analyze 19.3 ng of 1st strand cDNA from tumor lines. Daudi cells, which were observed to have low binding levels of NKp30/mFc2 and anti-zB7H6, gave a $Log_2$ Ct average value of 0.079 from 3 different reactions run in triplicate on three different days; therefore, 0.07 was used as a threshold to define zB7H6 positivity in the qRT-PCR assay. 23 of the 118 cell lines assayed were found to express zB7H6 message. Tumor cell lines expressing zB7H6 are listed in Table 8, below.

TABLE 8 zB7H6 positive tumor cell-lines

| Cell-line | Source | $2^{\hat{}}Ct$ |
|---|---|---|
| NCI-H716 | Colon | 0.152 |
| hct15 | Colon | 0.219 |
| hct116 | Colon | 0.070 |
| ht29 | Colon | 0.160 |
| HEP3B2.1.7 | Liver | 0.071 |
| HuH7 | Liver | 0.075 |
| C3a | Liver | 0.249 |
| hepg2 | Liver | 0.146 |
| Hela | Cervix | 0.097 |
| SHP-77 | Lung | 0.076 |
| NCI-H441 | Lung | 0.152 |
| BxPC3 | Pancreas | 0.983 |
| Aspc-1 | Pancreas | 0.074 |
| LN-CAP-FGC | Prostate | 0.095 |
| HL-60 | prohemocytic leukemia | 0.080 |
| GRANTA519 | B-cell lymphoma | 0.115 |
| DOHH2 | B-cell lymphoma | 0.088 |
| U-937 | Monocytic lymphoma | 0.184 |
| HEL92.1.7 | Erythroleukemia | 0.098 |
| Daudi | Burkitt's lymphoma | 0.079 |
| K562 | chronic myelogenous leukemia | 0.080 |
| 293F | | 0.091 |
| MV-4-11 | | 0.130 |

EXAMPLE 20

BxPC3 Pancreatic Carcinoma Model for Evaluating Efficacy of an Anti-zB7H6 Antibody or Antibody-Drug Conjugate Against Tumor Growth To test if an anti-zB7H6 antibody or antibody-drug conjugate has activity on tumor growth in mice, groups of mice are injected s.c with the BxPC3 pancreatic tumor on Day 0. Once tumors grow to 150-200 mm³, groups of mice (n=10/gp) mice are then injected with 1 mg/Kg to 30 mg/Kg control reagent, anti-zB7H6 antibody, or anti-zB7H6 antibody-drug conjugate 1×-3×/week for 3 weeks. Tumor volume is monitored 3×/week for 5 weeks. Significantly smaller tumors in mice injected with a an anti-zB7H6 antibody or antibody-drug conjugate, as compared to mice injected with control reagent, indicates efficacy of the antagonist for inhibition of tumor growth.

Study design: Eight to ten-week old female C.B-17 SCID mice (Charles River Laboratories) are injected s.c. on the right flank with 2×10⁶ BxPC-3 cells on Day 0, Starting with a tumor size of 150-200 mm³, groups of mice (n=10/group) are injected i.p. with 1 mg/Kg to 30 mg/Kg control reagent, anti-zB7H6 antibody, or anti-zB7H6 antibody-drug conjugate 1×-3×/week for 3 weeks. Tumor growth is monitored 3×/week for 5 weeks using caliper measurements. Tumor volume is calculated using the formula $½*(B)^2*L$ (mm³).

EXAMPLE 21

Inhibition of Human Hepatocellular Carcinoma Cell Growth In Vivo Using Anti-zB7H6 Antibody or Antibody-Drug Conjugate To evaluate anti-tumor activity of an anti-zB7H6 antibody or antibody-drug conjugate against human hepatocellular carcinoma cells in vivo, groups of BALB/c nude mice are injected with either HuH7 or C3A hepatocellular carcinoma cells on Day 0. Groups (n=10/group) of tumor bearing mice receive 5-75 µg of anti-zB7H6 antibody or antibody-drug conjugate by i.p. or peritumoral injection every other day (EOD) from Days 5-33. Tumor volume is monitored 3×/week for 6 weeks. Inhibition of tumor growth by anti-zB7H6 antibody or antibody-drug conjugate indicates that the respective protein has inhibitory effects on human heptocellular carcinoma in vivo.

Study design: Eight-week old female BALB/c nude mice (Charles River Laboratories) are injected s.c. on the right flank with 6×10⁶ HuH7 or C3A cells on Day 0. Groups of mice (n=10/group) are injected i.p. or peritumorally with 5 µg-75 µg of an anti-zB7H6 antibody or anti-zB7H6 antibody-drug conjugate from days 5-33. Injections are given in a total volume of 200 µl. Tumor growth is monitored 3×/week for 6 weeks using caliper measurements. Tumor volume was calculated using the formula $½*(B)^2*L$ (mm³).

EXAMPLE 22

Inhibition of Human Prostate Carcinoma Cell Growth In Vivo Using Anti-zB7H6 Antibody or Antibody-Drug Conjugate To evaluate anti-tumor activity of an anti-zB7H6 antibody or antibody-drug conjugate against human prostate carcinoma cells in vivo, groups of BALB/c nude mice are injected with either PC-3 or DU-145 prostate carcinoma cells on Day 0. Groups (n=10/group) of tumor bearing mice receive 5-75 µg of anti-zB7H6 antibody or anti-zB7H6 antibody-drug conjugate by i.p. or peritumoral injection every other day (EOD) from Days 5-33. Tumor volume is monitored 3×/week for 6 weeks. Inhibition of tumor growth (volume or weight) by an anti-zB7H6 antibody or antibody-drug conjugate indicates that the respective protein has inhibitory effects on human prostate carcinoma in vivo.

Study design: Eight-week old female BALB/c nude mice (Charles River Laboratories) are injected s.c. on the right flank or orthotopically in the prostate lobe with 10×10⁶ PC-3 or 6×10⁶ DU-145 cells on Day 0. Groups of mice (n=10/ group) are injected i.p. or peritumorally (s.c model only) with 5-75 μg of anti-zB7H6 antibody or anti-zB7H6 antibody-drug conjugate from days 5-33. Injections are given in a total volume of 200 μl. For s.c tumors, tumor growth is monitored 3×/week for 6 weeks using caliper measurements. Tumor volume is calculated using the formula $½*(B)^2*L$ (mm$^3$). For orthotopic tumors, mice are terminated at the end of the study and tumor weighed to enable tumor load assessment.

EXAMPLE 23

Inhibition of Human Colon Carcinoma Cells In Vivo Using Anti-zB7H6 Antibody or Antibody-Drug Conjugate To evaluate anti-tumor activity of an anti-zB7H6 antibody or antibody-drug conjugate against human colon carcinoma cells in vivo, groups of BALB/c nude mice are injected with either DLD-1 or HCT-116 colon carcinoma cells on Day 0. Groups (n=10/group) of tumor bearing mice receive 5-75 μg of anti-zB7H6 antibody or anti-zB7H6 antibody-drug conjugate by i.p. or peritumoral injection every other day (EOD) from Days 5-33. Tumor volume is monitored 3×/week for 6 weeks. Inhibition of tumor growth (volume or weight) by anti-zB7H6 antibody or antibody-drug conjugate suggests that the respective protein has inhibitory effects on human colon carcinoma in vivo.

Study design: Eight-week old female BALB/c nude mice (Charles River Laboratories) are injected s.c. on the right flank or orthotopically in the colonic wall with 6×10$^6$ DLD-1 or HCT-116 cells on Day 0. Groups of mice (n=10/group) are injected i.p. or peritumorally (for s.c model only) with 5-75 μg of anti-zB7H6 antibody or anti-zB7H6 antibody-drug conjugate from days 5-33. Injections are given in a total volume of 200 μl. For s.c tumors, tumor growth is monitored 3×/week for 6 weeks using caliper measurements. Tumor volume is calculated using the formula $½*(B)^2*L$ (mm$^3$). For orthotopic tumors, mice are terminated at the end of the study and tumor weighed to enable tumor load assessment.

EXAMPLE 24

Inhibition of Human Pancreatic Carcinoma Cells In Vivo Using Anti-zB7H6 Antibody or Antibody-Drug Conjugate To evaluate anti-tumor activity of an anti-zB7H6 antibody or antibody-drug conjugate against human pancreatic carcinoma cells in vivo, groups of BALB/c nude mice are injected with either BxPC-3 or HPAF-II pancreatic carcinoma cells on Day 0. Groups (n=10/group) of tumor bearing mice receive 5-75 μg of anti-zB7H6 antibody or anti-zB7H6 antibody-drug conjugate by i.p. or peritumoral injection every other day (EOD) from Days 5-33. Tumor volume is monitored 3×/week for 6 weeks. Inhibition of tumor growth (volume or weight) by anti-zB7H6 antibody or antibody-drug conjugate suggests that the respective protein has inhibitory effects on human pancreatic carcinoma in vivo.

Study design: Eight-week old female BALB/c nude mice (Charles River Laboratories) are injected s.c. on the right flank or orthotopically in the pancreatic lobe with 6×10$^6$ BxPC-3 or HPAF-II cells on Day 0. Groups of mice (n=10/group) are injected i.p. or peritumorally (for s.c model only) with 5-75 μg of anti-zB7H6 antibody or anti-zB7H6 antibody-drug conjugate from days 5-33. Injections are given in a total volume of 200 μl. For s.c tumors, tumor growth is monitored 3×/week for 6 weeks using caliper measurements. Tumor volume was calculated using the formula $½*(B)^2*L$ (mm$^3$). For orthotopic tumors, mice are terminated at the end of the study and tumor weighed to enable tumor load assessment.

EXAMPLE 25

Inhibition of B-Cell Lymphoma In Vivo Using Anti-zB7H6 Antibody or Antibody-Drug Conjugate Human B-lymphoma cell lines are maintained in vitro by passage in growth medium. The cells are washed thoroughly in PBS to remove culture components.

SCID Mice are injected with (typically) 1×10$^6$ human lymphoma cells via the tail vein in a 100 microliter volume. The optimal number of cell injected is determined empirically in a pilot study to yield tumor take consistently with desired kinetics. Anti-zB7H6 antibody or antibody-drug conjugate treatment is begun the next day by either subcutaneous implantation of an ALZET® osmotic mini-pump (ALZET, Cupertino, Calif.) or by daily i.p. injection of anti-zB7H6 antibody or antibody-drug conjugate or vehicle. Mice are monitored for survival and significant morbidity. Mice that lose greater than 20% of their initial body weight are sacrificed, as well as mice that exhibit substantial morbidity such as hind limb paralysis. Depending on the lymphoma cell line employed, the untreated mice typically die in 3 to 6 weeks. For B cell lymphomas that secrete IgG or IgM, the disease progression can also be monitored by weekly blood sampling and measuring serum human immunoglobulin levels by ELISA.

Anti-zB7H6 Antibody or Antibody-Drug Conjugate Dose Response/IM-9 Model

Mice are injected with 1×10$^6$ IM-9 cells, and 28 day osmotic mini pumps implanted the following day. The pumps are loaded with the following concentrations of zB7H6 antibody or antibody-drug conjugate to deliver: 0, 0.12, 1.2, or 12 micrograms per day with 8 mice per dose group. Increased protection of mice from the tumor cell line with increased dose of antibody or antibody-drug conjugate indicates that the effects of the anti-zB7H6 antibody or antibody-drug conjugate are dose dependent. Surviving mice at the end of the experiment have no signs of disease and no detectable human IgG in their serum.

These data demonstrate that the efficacy of anti-zB7H6 antibody or anti-zB7H6 antibody-drug conjugate in SCID mouse lymphoma models correlates with the ability to inhibit the growth of the lymphoma cell lines in vivo.

EXAMPLE 26

Inhibition of B-Cell Derived Tumors In Vivo Using Anti-zB7H6 Antibody or Antibody-Drug Conjugate Administration of anti-zB7H6 antibody or anti-zB7H6 antibody-drug conjugate by constant infusion via mini-osmotic pumps results in steady state serum concentrations proportional to the concentration of the antibody or antibody-drug conjugate contained in the pump. 0.22 ml of anti-zB7H6 antibody or antibody-drug conjugate contained in phosphate buffered saline (pH 6.0) at a concentration of 2 mg/ml or 0.2 mg/ml is loaded under sterile conditions into Alzet mini-osmotic pumps (model 2004; Alza corporation Palo Alto, Calif.). Pumps are implanted subcutaneously in mice through a 1 cm incision in the dorsal skin, and the skin is closed with sterile wound closures. These pumps are designed to deliver their contents at a rate of 0.25 μl per hour over a period of 28 days. This method of administration results in significant increase in survival in mice injected with tumor cells (below). Effect of Anti-zB7H6 Antibody or Antibody Drug Conjugate on B-Cell Derived Tumors In Vivo The effects of anti-zB7H6 antibody or antibody-drug conjugate are tested in vivo using a mouse tumor xenograft model described herein. The xenograft model to be tested is human lymphoblastoid cell line IM-9 (ATCC No. CRL159). C.B-17 SCID mice (female C.B-17/IcrHsd-scid; Harlan, Indianapolis, Ind.) are divided into 4 groups. On day 0, IM-9 cells (ATCC No. CRL159) are harvested from culture and injected intravenously, via the tail vein, to all mice (about 1,000,000 cells per mouse). On day 1, mini-osmotic pumps containing test article or control article are implanted subcutaneously in the mice. Mice in groups 1-3 (n=9 per group) are delivered anti-zB7H6 antibody or antibody-drug conjugate: group 1 contains 2.0 mg/mL of antibody or antibody-drug conjugate and is delivered 12 µg per day; group 2 contains 0.20 mg/mL and is delivered 1.2 µg per day; group 3 contained 0.02 mg/mL and is delivered 0.12 µg per day. Mice in group 4 (n=9) are a control and are treated with vehicle (PBS pH 6.0).

Increased survival of treatment groups (e.g., either 12 µg/day or 1.2 µg/day) compared to vehicle treated mice shows that anti-zB7H6 antibody or antibody-drug conjugate reduces the effects of the B-cell tumor cells in vivo.

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. An isolated, soluble fusion protein comprising a polypeptide segment that has at least 90% sequence identity with the amino acid sequence set forth in residues 25-266 of SEQ ID NO:2, wherein said polypeptide is capable of specifically binding to human natural killer cell receptor NKp30, and wherein said fusion protein further comprises a vasodilator-stimulated phosphoprotein (VASP) domain.

2. The fusion protein of claim 1, wherein the polypeptide segment consists of the amino acid sequence set forth in residues 25-266 of SEQ ID NO:2.

* * * * *